(12) United States Patent
Pan et al.

(10) Patent No.: US 10,480,021 B2
(45) Date of Patent: Nov. 19, 2019

(54) METHODS FOR CLOSED CHROMATIN MAPPING AND DNA METHYLATION ANALYSIS FOR SINGLE CELLS

(71) Applicant: Yale University, New Haven, CT (US)

(72) Inventors: Xinghua Pan, Hamden, CT (US); Sherman M. Weissman, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 464 days.

(21) Appl. No.: 14/747,796

(22) Filed: Jun. 23, 2015

(65) Prior Publication Data

US 2015/0368694 A1     Dec. 24, 2015

Related U.S. Application Data

(60) Provisional application No. 62/015,965, filed on Jun. 23, 2014.

(51) Int. Cl.
*C12P 19/34* (2006.01)
*C12Q 1/6827* (2018.01)

(52) U.S. Cl.
CPC .................................. *C12Q 1/6827* (2013.01)

(58) Field of Classification Search
USPC ............ 435/6.1, 6.11, 6.12, 91.1, 91.2, 183; 436/94, 501; 536/23.1, 24.3, 24.33, 25.3
See application file for complete search history.

(56) References Cited

U.S. PATENT DOCUMENTS

| | | | |
|---|---|---|---|
| 5,001,050 A | 3/1991 | Blanco | |
| 5,198,543 A | 3/1993 | Blanco | |
| 6,287,825 B1 | 9/2001 | Weissman | |
| 6,346,399 B1 | 2/2002 | Weissman | |
| 6,372,434 B1 | 4/2002 | Weissman | |
| 6,924,104 B2 | 8/2005 | Weissman | |
| 2003/0129602 A1* | 7/2003 | Huang ................. | C12Q 1/6855 435/6.12 |
| 2006/0057595 A1* | 3/2006 | Lao ...................... | C12Q 1/6851 435/6.12 |
| 2006/0134650 A1* | 6/2006 | Gunderson .......... | C12Q 1/6827 435/6.12 |
| 2007/0054295 A1* | 3/2007 | Spivack ................ | C12Q 1/686 435/6.12 |
| 2008/0081338 A1* | 4/2008 | Lo ........................ | C12Q 1/6886 435/6.12 |
| 2009/0042196 A1* | 2/2009 | Guo ...................... | C12Q 1/6858 435/6.11 |
| 2014/0213485 A1 | 7/2014 | Weissman | |

OTHER PUBLICATIONS

Adli, et al., "Genome-wide chromatin maps derived from limited numbers of hematopoietic progenitors," Nat Methods, 7:615-8 (2010).
Adli, et al., "Whole-genome chromatin profiling from limited numbers of cells using nano-ChIP-seq," Nat Protoc., 6:1656-68 (2011).
Adzhubei, et al., "A method and server for predicting damaging missense mutations," Nat Methods, 7:248-9 (2010).
Aktipis, et al., "Overlooking Evolution: A Systematic Analysis of Cancer Relapse and Therapeutic Resistance Research," PloS One, 6(11):e26100 (2011).
Alelu-Paz, et al., "DNA methylation, histone modifications, and signal transduction pathways: a close relationship in malignant gliomas pathophysiology," J Signal Transduct, 2012:956-8 (2012).
Almendro, et al., "Cellular heterogeneity and molecular evolution in cancer," Annual Review of Pathology, 8:277-302 (2013).
Anderson, et al., "Genetic variegation of clonal architecture and propagating cells in leukaemia," Nature, 469:356-61 (2011).
Apodtolou, et al., "Chromatin dynamics during cellular reprogramming," Nature, 502:462-71 (2013).
Ashkenazi, et al., "Pathways to tumorigenesis—modeling mutation acquisition in stem cells and their progeny," Neoplasia, 10:1170-82 (2008).
Attolini, et al., "Evolutionary theory of cancer," Ann N Y Acad Sci, 1168:23-51 (2009).
Auerbach, et al., "Mapping accessible chromatin regions using Sono-Seq," PNAS, 106:14926-31 (2009).
Avner, et al., "Overcoming drug resistance in multi-drug resistant cancers and microorganisms: a conceptual framework ," Bioengineered, 3:262-70 (2012).
Banerji, et al., "Sequence analysis of mutations and translocations across breast cancer subtypes," Nature, 486:405-9 (2012).
Barretina, et al., "The Cancer Cell Line Encyclopedia enables predictive modelling of anticancer drug sensitivity," Nature, 483(7391):603-7 (2012).
Bedard, et al., "Decoding the evolution of a breast cancer genome," EMBO Mol Med., 2:3-5 (2010).
Beerman, et al., "Proliferation—dependent alterations of the DNA methylation landscape underlie hematopoietic stem cell aging," Cell Stem Cell, 12:413-25 (2013).
Bell, et al., "Determinants and dynamics of genome accessibility," Nat Rev Genet, 12:554-64 (2011).

(Continued)

*Primary Examiner* — Frank W Lu
(74) *Attorney, Agent, or Firm* — Pabst Patent Group LLP

(57) ABSTRACT

Methods of identifying DNase I Hyper-Resistant Sites (DHRS), or in board sense, highly compact chromatin and characterizing the DNA methylation status of DMRs such as CpG islands and CpG island shores are provided. The methods are particularly useful for analysis of genomic DNA from low quantities of cells, for example, less than 1,000 cells, less than 100 cells, less than 10 cells, or even one cell, and can be used to generate chromatin and methylation profiles. The downstream analyses include in parallel massive sequencing, microarray, PCR and Sanger sequencing, hybridization and other platforms. These methods can be used to generate chromatin and DNA methylation profiles in drug development, diagnostics, and therapeutic applications are also provided.

19 Claims, 16 Drawing Sheets
Specification includes a Sequence Listing.

(56) References Cited

OTHER PUBLICATIONS

Bellamy, et al., "Development and characterization of a melphalan-resistant human multiple myeloma cell line," Cancer Research, 51: 995-1002 (1991).
Benjamini, et al., "Summarizing and correcting the GC content bias in high-throughput sequencing," Nucleic Acids Res., 40:e72 (2012).
Berger, "The complex language of chromatin regulation during transcription," Nature, 447:407-12 (2007).
Binder, et al., "Silver-Russell syndrome," Best Pract Res Clin Endocrinol Metab., 25(1):153-60 (2011).
Bocker, et al., "Genome-wide promoter DNA methylation dynamics of human hematopoietic progenitor cells during differentiation and aging," Blood 117, e182-9 (2011).
Bouabdallah, et al., "True histiocytic lymphoma following B-acute lymphoblastic leukemia: case report with evidence for a common clonal origin in both neoplasms," Br J Haematol, 113:1047-50 (2001).
Boyd, et al., "Measurement and clinical monitoring of human lymphocyte clonality by massively parallel VDJ pyrosequencing," Sci Translational Med., 1:12ra23 (2009).
Brukner, et al., "Self-priming arrest by modified random oligonucleotides facilitates the quality control of whole genome amplification," Anal Biochem., 39:3457 (2005).
Buenrostro, et al., "Transposition of native chromatin for fast and sensitive epigenomic profiling of open chromatin, DNA-binding proteins and nucleosome position," Nat Methods, 10:1213-8 (2013).
Burgess-Beusse, et al., "The insulation of genes from exteTtlal enhancers and silencing chromatin," PNAS, 99(4):16433-7 (2002).
Cahan, et al., "Origins and implications of pluripotent stem cell variability and heterogeneity," Nature reviews. Molecular cell biology, 14:357-68 (2013).
Cairns, "Mutation selection and the natural history of cancer," Sci Aging Knowledge Environ, 2006: 10:cp1 (2006).
Campbell, et al., "Subclonal phylogenetic structures in cancer revealed by ultra-deep sequencing," PNAS, 105:13081-6 (2008).
Campbell, et al., "The patterns and dynamics of genomic instability in metastatic pancreatic cancer," Nature, 467:1109-13 (2010).
Chen, et al., "A restricted cell population propagates glioblastoma growth after chemotherapy," Nature, 488:522-6 (2012).
Chen, et al., "Building mixture trees from binary sequence data," Biometrika, 93:843-60 (2006).
Chen, et al., "Clustering-based identification of clonally-related immunoglobulin gene sequence sets," Immunome Res., 6(1):84 (2010).
Chen, et al., "DNA methylation and demethylation in mammals," The Journal of Biological Chemistry, 286:18347-53 (2011).
Choi, "Combinatorial patterns of somatic gene mutations in cancer," Proceedings of the ACM Conference on Bioinformatics, Computational Biology and Biomedicine, 414-7 (2012).
Clapier, et al., "The biology of chromatin remodeling complexes". Annual Review of Biochemistry, 78:273-304 (2009).
Clement, et al., "TCS: a computer program to estimate gene genealogies," Mol Ecol, 9:1657-9 (2000).
Costello, et al., "Aberrant CpG-island methylation has non-random and tumour-type-specific patterns," Nat Genet, 24:132-8 (2000).
Crawford, et al., "Genome- wide mapping of DNase hypersensitive sites using massively parallel signature sequencing (MPSS)," Genome Res., 16:123-31 (2006).
Crawford, et al., "Identifying gene regulatory elements by genome-wide recovery of DNase hypersensitive sites," PNAS, 101:992-7 (2004).
Crespi, et al., "Evolutionary biology of cancer," Trends in Ecology & Evolution, 20:545-52 (2005).
Dalton, et al., "Characterization of a new drug-resistant human myeloma cell-line that expresses P-glycoprotein," Cancer Res., 46:5125-30 (1986).
Degner, et al., "DNase 1 sensitivity QTLs are a major determinant of human expression variation," Nature, 482:390-4 (2012).
Desper, et al., "Distances based reconstruction of tree models for oncogenesis," Journal of Computational Biology: J Comput Biol., 7:789-803 (2000).
Diaz-Cano, "Tumor heterogeneity: mechanisms and bases for a reliable application of molecular marker design," International Journal of Molecular Sciences, 13:1951-2011 (2012).
Dietterich, "Ensemble methods in machine learning," Multiple Classifier Systems, vol. 1857: 1-15 (2000).
Ding, et al., "Clonal evolution in relapsed acute myeloid leukaemia revealed by whole-genome sequencing," Nature, 481:506-10 (2012).
Dobbs, et al., "Dynamics of DNA methylation during early development of the preimplantation bovine embryo," PloS one 8, e66230 (2013).
Doyon, et al., "Models, algorithms and programs for phylogeny reconciliation," Briefings in Bioinformatics, 12:392-400 (2011).
Driessens, et al., "Defining the mode of tumor growth by clonal analysis," Nature, 488:527-30 (2012).
Durrett, et al., "Evolution of resistance and progression to disease during clonal expansion of cancer," Theor Popul Biol., 77:42-8 (2009).
Eroglu, et al., "Role of ART in imprinting disorders," Semin Reprod Med., 30:92-104 (2012).
Estecio, et al., "High-throughput methylation profiling by MCA coupled to CpG island microarray," Genome Res., 17:1529-36 (2007).
Farlik, et al., "Single-cell DNA methylome sequencing and bioinformatic inference of epigenomic cell-state dynamics," Cell Rep., 10(8):1386-97 (2015).
Fearon, et al., "A genetic model for colorectal tumorigenesis," Cell, 61:759-67 (1990).
Feldman, et al., "Clonally related follicular lymphomas and histIocytic/dendritic cell sarcomas: evidence for transdifferentiation of the follicular lymphoma clone," Blood, 111:5433-9 (2008).
Feldman, et al.,"Clonal relationship between precursor T-lymphoblastic leukaemia/lymphoma and Langerhans-cell histiocytosis," Lancet Oncol, 6:435-7 (2005).
Fidler, et al., "Genomic analysis of primary tumors does not address the prevalence of metastatic cells in the population," Nature Genetics, 34:23 (2003).
Fidler, et al.,"Clonal relationship between precursor T-lymphoblastic leukaemia/lymphoma and Langerhans-cell histiocytosis," Science, 197:893-5 (1977).
Francastel, et al, "Nuclear compartmentalization and gene activity. future reviews," Mole Cell Biol., 1(2)137-43 (2000).
Fuks, et al., "The methyl-CpG-binding protein MeCP2 links DNA methylation to histone methylation," J Biol Chem., 278:4035-40 (2003).
Gafni, et al., "Derivation of novel human ground state naïve pluripotent stem cells," Nature, 504(7479):282-6 (2013).
Gardiner-Garden, et al., "CpG islands in vertebrate genomes," J Molecular Biol., 196(2):261-82 (1987).
Gatenby, et al., "Adaptive therapy," Cancer Research, 69:4894-903 (2009).
Geiman, et al., ,"Chromatin remodeling, histone modifications, and DNA methylation-how does it all fit together ," J Cell Biochem, 87:117-25 (2002).
Gerlinger, et al., "How Darwinian models inform therapeutic failure initiated by clonal heterogeneity in cancer medicine," Br J Cancer, 103:1139-43 (2010).
Gerlinger, et al., "Parallel progression of primary tumours and metastases," N Eng J Med., 366:883-92 (2012).
Gibbs, et al., "Single-cell phospho-specific flow cytometric analysis demonstrates biochemical and functional heterogeneity in human hematopoietic stem and progenitor compartments," Blood, 117:4226-33 (2011).
Gilbert, et al., "CRISPR-mediated modular RNA-guided regulation of transcription in eukaryotes," Cell, 154:442-51 (2013).
Gonzalez, et al., "DNA replication, RNAi and epigenetic inheritance," Epigenetics:, 7(1):14-9 (2012).
Greaves, et al., "Clonal e\solution in cancer," Nature, 481:306-13 (2012).
Greenman, et al., "Estimation of rearrangement phylogeny for cancer genomes," Genome Res, 22:346-61 (2012).

(56) References Cited

OTHER PUBLICATIONS

Greulich, et al., "Mutational Pathway Determines Whether Drug Gradients Accelerate EVOlution of Drug-Resistant Cells," Physical Rev Letters, 109 (2012).
Grindberg, et al., "RNA-sequencing from single nuclei," Pros Natl Acad Sci U A, 110:19802-7 (2013).
Gu, et al., "Preparation of reduced representation bisulfite sequencing libraries for genome-scale DNA methylation profiling," Nat Protoc., 6:468-81 (2011).
Guo, et al., "Nonstochastic Reprogramming from a Privileged Somatic Cell State," Cell, 156:649-62 (2014).
Guo, et al., "Single-cell methylome landscapes of mouse embryonic stem cells and early embryos analyzed using reduced representation bisulfite sequencing," Genome Res., 23 (12):2126-35 (2013).
Hahn, et al., "Relationship between gene body DNA methylation and intragenic H3K9me3 and H3K36me3 chromatin marks," PloS One 6, e18844 (2011).
Hainaut, et al., Targeting the hallmarks of cancer: towards a rational approach to next- generation cancer therapy:, Curr Opin Oncol., 25:50-1 (2013).
Halaban, et al., "PLX4082, a selective BRAF(V600E) kinase inhibitor, activates the ERK pathway and enhances cell migration and proliferation of BRAF melanoma cells," Pigment Cell Melanoma Res., 23:190-200 (2010).
Hampton, et al., "A sequence-level map of chromosomal breakpoints in the MCF-7 breast cancer cell line yields insights into the evolution of a cancer genome," Genome Res, 19:167-77 (2009).
Hanahan, et al., "Hallmarks of cancer: the next generation," Cell, 144:646-74 (2011).
Hashimshony, et al., ,"CEL-Seq: single-cell RNA-Seq by multiplexed linear amplifi- cation," Cell Rep, 2:666-73 (2012).
Henikoff, et al., "Genome-wide profiling of salt fractions maps physical properties of chromatin," Genome Res, 19:460-469 (2009).
Hjelm, et al., "New probabilistic network models and algorithms for oncogenesis," J Comput Biol., 13:853-5 (2006).
Hnisz, et al., "Super-enhancers in the control of cell identity and disease," Cell, 155:934-47 (2013).
Hodges, et al., "Directional DNA methylation changes and complex intermediate states accompany lineage specificity in the adult hematopoletic compartment," Mol Cell, 44:17-28 (2011).
Hogart, et al., "Genome-wide DNA methylation profiles in hematopoietic stem and progenitor cells reveal overrepresentation of ETS transcription factor binding sites," Genome Res., 22:1407-18 (2012).
Hou, et al., "Single-Cell Exome Sequencing and Monoclonal Evolution of a \textitJAK2-Negative Myeloproliferative Neoplasm," Cell, 148:873-85 (2012).
Huang, et al., "MED12 controls the response to multiple cancer drugs through regulation of TGF-beta receptor signaling," Cell, 151: 937-50 (2012).
Huelsenbeck, et al., "Bayesian inference of phylogeny and its impact on evolutionary biology," Science, 294:2310-4 (2001).
Hutchison, et al., "Cell-free cloning using phi29 DNA polymerase," PNAS, 102:17332-6 (2005).
Hutchison, et al., "Single-cell genomics," Nat Biotechnol., 24:657-8 (2006).
Iacobuzio-Donahue, "Genetic evolution of pancreatic cancer: lessons learnt from the pancreatic cancer genome sequencing project," Gut, 61:1085-94 (2012).
Inoue, et al., "Improvements of rolling circle amplification (RCA) efficiency and accuracy using Thermus thermophilus SSB mutant protein," Nucleic Acids Res., 34:e69 (2006).
Irish, et al., "Single Cell Profiling of Potentiated Phospho-Protein Networks in Cancer hells," Cell, 118:217-28 (2004).
Irizarry, et al., "The human colon cancer methylome shows similar hypo- and hypermethylation at conserved tissue-specific CpG island shores," Nat Genet, 41 (2):178-86 (2009).
Islam, et al., "Characterization of the single-cell transcriptional landscape by highly multiplex RNA-seq," Genome Research, 21:1160-7 (2011).
Iwasa, et al., "Evolution of resistance during clonal expansion," Genetics 172:2557-66 (2006).
Jaffe, et al., "Bump hunting to identify differentially methylated regions in epigenetic epidemiology studies," Int J Epidemiol., 41:200-9 (2012).
Jones, et al., "The role of DNA methylation in mammalian epigenetics," Science, 293:1068-70 (2001).
Jursch, et al., "Regulation of DNA transposition by CpG methylation and chromatin structure in human cells," Mob DNA, 4:15 (2013).
Kangaspeska, et al., "Transient cyclical methylation of promoter DNA," Nature, 452:112-5 (2008).
Kannan, et al., "Maximum parsimony on phylogenetic networks," Algorithms Mol Biol, 7:9 (2012).
Kashiwagi, et al., "DNA methyltransferase 3b preferentially associates with condensed chromatin," Nucleic Acids Research, 39:874-88 (2011).
Klein, "Parallel progression of primary tumors and metastases," Cancer, 9:302-12 (2009).
Kluger, et al., "Relationship between gene co-expression and probe localization on microarray slides," BMC Genomics, 4:42-9 (2003).
Koga, et al., "Genome-wide screen of promoter methylation identifies novel markers in melanoma," Genome Res., 19:1462-70 (2009).
Korbel, et al., "Paired-end mapping reveals extensive structural variation in the human genome," Science, 318:420-6 (2007).
Krauthammer, et al., "Exome sequencing identifies recurrent somatic RAC I mutations in melanoma," Nature Genetics, 44:1006-14 (2012).
Ku, et al., "Studying the epigenome using next generation sequencing," J MedGene, 48:721-30 (2011).
Kumar, et al., Predicting the effects of coding non-synonymous variants on protein function using the SIFT algorithm, Nature Protocols, 4:1073-81 (2009).
Kuribayashi, et al., "Chromatin structure and endonuclease sensitivity in human leukemic cell lines," Anticancer Res., 16(3A):1225-30 (1996).
Lage, et al., "Whole genome analysis of genetic alterations in small DNA samples using hyperbranched strand displacement amplification and array-CGH," Genome Res., 13:294-307 (2003).
Lambert, et al., "An analogy between the e\solution of drug resistance in bacterial communities and malignant tissues," Nat Rev Cancer, 11: 375-82 (2011).
Lasken, "Single-cell sequencing in its prime," Nature Biotech, 31:211-2 (2013).
Lee, et al., "Sequential application of anticancer drugs enhances cell death by rewiring apoptotic signaling networks," Cell, 149:780-94 (2012b).
Lee, et al., "Tumour heterogeneity and drug resistance: Personalising cancer medicine through functional genomics," Biochemical Pharmacology, 83:1013-20 (2012a).
Leek, et al., "Capturing heterogeneity in gene expression studies by surrogate variable Analysis," PLoS Genetics, 3:1724-35 (2007).
Leek, et al., "Tackling the widespread and critical impact of batch effects in high-throughput data," Genetics, 11:733-9 (2010).
Leiserson, et al., "Simultaneous identification of multiple driver pathways in cancer," PLoS Computational Biology, 9:e1003054 (2013).
Lessard, et al., "Chromatin regulatory mechanisms in pluripotency," Annu Rev Cell Dev Biol., 26:503-32 (2010).
Lieb, et al., "Promoter-specific binding of Rap1 revealed by genome-wide maps of protein-DNA association," Nat Genet., 28:327-34 (2001).
Ling, et al., "Isolation of nuclei for use in genome-wide DNase hypersensitivity assays to probe chromatin structure ," Methods Mole Biol, 977:13-9 (2013).
Loeb, "Human cancers express mutator phenotypes: origin, consequences and targeting," Cancer, 11: 450-7 (2011).
Loven, "Selective inhibition of tumor oncogenes by disruption of super-enhancers," Cell, 153:320-34 (2013).
Marcy, et al., "Nanoliter reactors improve multiple displacement amplification of genomes from single cells," PLoS Genet., 3:1702-8 (2007).

(56) References Cited

OTHER PUBLICATIONS

Martin, et al., "Chromatin condensation modulates access and binding of nuclear proteins ," FASEB, J 24:1066-72 (2010).
Marusyk, et al., "intra-tumour heterogeneity: a looking glass for cancer," Cancer, 12: 323-34 (2012).
Matsushita, et al. "Cancer exome analysis re\leafs a T-cell-dependent mechanism of cancer immunoediting,", Nature, 482:400-4, (2012).
Mercer, et al.,"DNase I-hypersensitive exons colocalize with promoters and distal regulatory elements," Nat Genet, 45:852-9 (2013).
Merlo, et al., "A comprehensive survey of clonal diversity measures in Barrett's esophagus as biomarkers of progression to esophageal adenocarcinoma," Cancer Prev Res., 3:1388-97 (2010).
Michor, et al., "Dynamics of colorectal cancer," Seminars in Cancer Biology, 15:484-93 (2005).
Mills, et al., "Clonal genetic and hematopoietic heterogeneity among human induced pluripotent stem cell lines.," Blood, 122:2047-51 (2013).
Moreira-Pinto, et al., "Beckwith-Wiedemann syndrome, delayed abdominal wall closure, and neonatal intussusception—case report and literature review," Fetal Pediatr Pathol., 31(6):448-52 (2012).
Mullighan, et al., "Genomic analysis of the clonal origins of relapsed acute lymphoblastic leukemia," Science, 322:1377-80 (2008).
Nagano, "Single" cell Hi-C reveals cell-to-cell variability in chromosome structure , Lubling, et al., Nature, 502:59-64 (2013).
Navin, et al., "Future medical applications of single-cell sequencing in cancer," Genome Med, 3:31 (2011a).
Navin, et al., "Inferring tumor progression from genomic heterogeneity," Genome Research, 20:68-80 (2010).
Navin, et al., "Tumor evolution inferred by single-cell sequencing ," Nature, 472:90-4 (2011b).
Negrotto, et al., "CpG methylation patterns and decitabine treatment response in acute myeloid leukemia cells and normal hematopoietic precursors," Leukemia, 26:244-54 (2012).
Nguyen, et al., "Altered chPomatin structure associated with methylation- induced gene silencing in canCeT Cells: cOrrelation of accessibility, methylation, MeCP2 binding and acetylation," Nucleic Acids Res, 29:4598-606 (2001).
Nik-Zainal, et al., "The Life History of 21 Breast Cancers," Cell, 149:994-1007 (2012).
Notta, et al., "Evolution of human BCR-ABL1 lymphoblastic leukaemia-initiating cells," Nature, 469:362-7 (2011).
Nowell, "The clonal evolution of tumor cell populations," Science, 194:23-8 (1976).
Nueda, et al., "ARSyN: a method for the identification and removal of systematic noise in multifactorial time course microarray experiments," Biostatistics, 13(3):553-66 (2011).
Pan and Weissman, "An approach for global scanning of single mucleotide variations," PNAS, 99(14):9346-51 (2002).
Pan, et al., "A procedure for highly specific, sensitive, and unbiased whole-genome amplification," PNAS, 105:15499-504 (2008).
Pan, et al., "Two methods for full-length RNAsequencing for low quantities of cells and single cells," PNAS, 110:594-9 (2013).
Parisi, et al., "Detecting copy number status and uncovering subclonal markers in heterogeneous tumor biopsies," BMC Genomics, 12:230 (2011).
Parisi, et al., "Integrated analysis of tumor samples sheds light on tumor heterogeneity," The Yale Journal of Biology and Medicine, 85:347-61 (2012).
Park, et al., "Cellular and genetic diversity in the progression of in situ human breast carcinomas to an invasive phenotype," The Journal of Clinical Investigation, 120:636-44 (2010).
Parker, et al., "Chromatin stretch enhancer states drive cell-specific gene regulation and harbor human disease risk variants," PNAS, 110:17921-6 (2013).
Pelizzola, et al., "MEDME: an experimental and analytical methodology for the estimation of DNA methylation levels based on microarray derived MeDIP-enrichment," Genome Res., 18:1652-9 (2008).

Podlaha, et al., "Evolution of the cancer genome," Trends in Genetics:TIG, 28:155-63 (2012).
Prioleau, et al., "An insulator element and condensed chromatin region separate the chicken beta" globin locus from an independently regulated erythroid" specifl c folate receptor gene," EMBO J, 18:4035-48 (1999).
Qi, "Repurposing CRISPR as an RNA-guided platform for sequence-specific control of gene expression," Cell, 152:1173-83 (2013).
Qian, et al., "Identification and correction of spurious spatial correlations in microarray data," Biotechniques, 35(1):42-4, 46,48 (2003).
Qiu, et al., "Differentiation of human embryonic stem cells into hematopoietic cells by coculture with human fetal liver cells recapitulates the globin switch that occurs early in development," Exp Hematol, 33:1450-8 (2005).
Qiu, et al., Globin switches in yolk sac-like primitive and fetal-like definitive red blood cells produced from human embryonic stem cells, Blood, 111:2400-8 (2008).
Radmacher, et al., "Graph models of oncogenesis with an application to melanoma," J Theor Biol, 212:535-48 (2001).
Rais, et al., "Deterministic direct reprogramming of somatic cells to pluripotency," Nature, 502:65-70 (2013).
Ran, et al., "Double nicking by RNA-guided CRISPR Cas9 for enhanced genome editing specificity," Cell, 154:1380-9 (2013).
Read, et al.,"The evolution of drug resistance and the curious orthodoxy of aggressive chemotherapy," PNAS, 108 Suppl 2:10871-7 (2011).
Rodriguez-Brenes, et al., "Evolutionary dynamics of feedback escape and the development of stem-cell-driven cancers," PNAS, 108:18983-8 (2011).
Roesch, et al., "A Temporarily Distinct Subpopulation of Slow-Cycling Melanoma Cells 1s Required for Continuous Tumor Growth," Cell, 141:583-94 (2010).
Sasagawa, et al., "Quartz-Seq: a highly reproducible and sensitive single-cell RNA sequencing method, reveals non-genetic gene-expression heterogeneity," Genome Biol, 14:R31 (2013).
Saunders, et al., "Role of intratumoural heterogeneity in cancer drug resistance: molecular and clinical perspectives," EMBO Molecular Medicine, 4:675-84 (2012).
Schepers, et al., "Lineage tracing reveals Lgr5+ stem cell activity in mouse intestinal adenomas," Science, 337:730-5 (2012).
Schimmenti, et al., "Evaluation of newborn screening bloodspot-based genetic testing as second tier screen for bedside newborn hearing screening," GenetMed., 13:1006-10 (2011).
Shah, et al., "Mutational evolution in a lobular breast tumour profiled at single nucleotide resolution," Nature, 461:809-13 (2009).
Shah, et al., "The clonal and mutational evolution spectrum of primary triple-negative breast cancers," Nature, 486:395-9 (2012).
Shalek, et al., "Single-cell transcriptomics reveals bimodality in expression and splicing in immune cells ," Nature, 498:236-40 (2013).
Shann, et al., "Genome-wide mapping and characterization of hypomethylated sites in human tissues and breast cancer cell lines," Genome Res., 18:791-801 (2008).
Sheridan, et al., "Epigenetic characterization of the FMR1 gene and aberrant neurodevelopment in human induced pluripotent stem cell models of fragile X syndrome," PLoS One, 6(10):e2620 (2011).
Silva, et al., "A theoretical quantitative model for evolution of cancer chemotherapy resistance," Biology Direct, 5:25 (2010).
Sjö, et al., "Profiling of diffuse large B-cell lymphoma by immunohistochemistry: identification of prognostic subgroups," Eur J Haematol, 79:501-7 (2007).
Smallwood, et al., "Dynamic CpG island methylation landscape in oocytes and preimplantation embryos," Nat Genet, 43:811-4 (2011).
Smith, et al., "A unique regulatory phase of DNA methylation in the early mammalian embryo," Nature, 484:339-44 (2012).
Smith, et al., "DNA methylation: roles in mammalian development," Nat Rev Genet, 14:204-20 (2013).
Song, et al., "Open chromatin defined by DNaseI and FAIRE identifies regulatory elements that shape cell-type identity," Genome Research, 21:1757-67 (2011).
Spits, et al., "Whole-genome multiple displacement amplification from single cells," Nat Protoc., 1:1965-70 (2006).

(56) References Cited

OTHER PUBLICATIONS

Sprouffske, et al., "Accurate reconstruction of the temporal order of mutations in neoplastic progression," Cancer Prev Res, 4:1135-44 (2011).
Stauffer, et al., "CHMP1 is a novel nuclear matrix protein affecting chromatin structure and cell-cycle progression," J Cell Sci, 114:2383-93 (2001).
Strino, et al., "TrAp: a tree approach for fingerprinting subclonal tumor composition," Nucleic Acids Research (2013).
Szakacs, et al., "Targeting multidrug resistance in cancer," Drug Discovery, 5:219-34 (2006).
Tanaka, et al. "Transcriptional regulation in pluripotent stem cells vy methyl CpG-binding protein 2 (MeCP2)," Hum Mol Genet., 23(4):1045-55 (2014).
Tang, et al., "RNA-Seq analysis to capture the transcriptome landscape of a single cell," Nature Protocols, 5:516-35 (2010).
Teif, et al., "Predicting nucleosome positions on the DNA: combining intrinsic sequence preferences and remodeler activities," Nucleic Acids Research, 37:5641-55 (2009).
Travers, "DNA dynamics: bubble 'n' flip for DNA cyclisation," Curr Biology, 15 (10):R377-9 (2005).
Vaccarino, et al., "Induced pluripotent stem cells: a new tool to confront the challenge of neuropsychiatric disorders," Neuropharmacology, 60:1355-1363 (2011).
Van Berkum, et al., "Hi-C: a method to study the three-dimensional architecture of genomes," J Vis Exp., JoVE 39, pii: 1869 (2010).
Vandin, et al., "De novo discovery of mutated driver pathways in cancer," Genome Research, 22: 375-85 (2012).
Varela, et al., "Exome sequencing identifies frequent mutation of the SWI/SNF complex gene PBRM1 in renal carcinoma" . Nature, 469:539-42 (2011).
Varma, et al., "Diagnostic utility of immunohistochemistry in morphologically difficult prostate cancer: review of current literature," Histopathology, 47:1-16 (2005).
Vogelstein, et al., "Cancer genes and the pathways they control," Nature Medicine, 10:789-99, (2004).
von Heydebreck, et al., "Maximum likelihood estimation of oncogenetic tree models," Biostatistics, 5:545-56 (2004).
Walter, et al., "Clonal architecture of secondary acute myeloid leukemia," N Eng J Med, 366:1090-8 (2012).
Wang, et al., "The hTERT gene is embedded in a nuclease-resistant chromatin domain ," The Journal of Biological Chemistry, 279:55401-10 (2004a).
Wang, et al., "Balanced-PCR amplification allows unbiased identification of genomic copy changes in minute cell and tissue samples," Nucleic Acids Res., 32:e76 (2004).
Wang, et al., "Chromatin remodeling and cancer, Part I: Covalent histone modifications," Trends Mol Med, 13:363-72 (2007).
Wang, et al., "Robust measurement of telomere length in single cells," PNAS, 110:E1906-12 (2013).
Weber, et al., "Distribution, silencing potential and evolutionary impact of promoter DNA methylation in the human genome," Nature Genetics, 39:457-66 (2007).
Weintraub, et al., Chromosomal subunits in active genes have an altered conformation, Science, 193:848-56 (1976).
Whyte, et al. Master transcription factors and mediator establish super-enhancers at key cell identity genes, Cell, 153:307-19 (2013).
Wu, et al, "Chromatin remodeling and the control of gene expression," J Biol Chem., 272:28171-4 (1997).
Wu, et al., "Dynamic transcriptomes during neural differentiation of human embryonic stem cells revealed by short, long, and paired-end sequencing," PNAS, 107:5254-9 (2010).
Xia, et al., "Stable re'versal of multidrug resistance in colon cancer cells by RNA interference targeting the MDR1 gene," Mol Med Rep., 2:579-84 (2009).
Xu, et al., "Single-Cell Exome Sequencing Reveals Single-Nucleotide Mutation Characteristics of a Kidney Tumor," Cell, 148: 886-95 (2012).
Yamamoto, et al., "Determination of Clonality of Metastasis by Cell-Specific Color-Coded Fluorescent-Protein Imaging," .Cancer Res., 63: 7785-90 (2003).
Yan, et al., "Single-cell RNA-Seq profiling of human preimplantation embryos anal embryonic stem cells ," Nature Struct Mol Biol., 20:1131-9 (2013).
Yasukochi, et al., "X chromosome-wide analyses of genomic DNA methylation states and gene expression n male and female neutrophis," PNAS, 107 (8):3704-9 (2010).
Yates, et al., "Evolution of the cancer genome," Genetics, 13:795-806 (2012).
Yeang, et al., "Combinatorial patterns of somatic gene mutations in cancer," FASEB, 22:2605-22 (2008).
Zhang, et al., "Physics of Cancer: The Impact of Heterogeneity," Ann Rev Condensed Matter Physics, 3(3):363-82 (2012).
Zhang, et al., "Functional genomic screen of human stem cell differentiation reveals pathways involved in neurodevelopment and neurodegeneration" PNAS, 110:12361-6 (2013).
Zhang, et al., "Sequencing genomes from single cells by polymerase cloning," Nature Biotechnol., 24:680-6 (2006).
Zhu, et al., "Genome-wide chromatin state transitions associated with developmental an6 environmental cues," Cell, 152:642-54 (2013).
Zong, et al., "Genome" wide detection of single-nucleotide and copy- number variations of a single human cell, Science, 338:1622-6 (2012).
Zullo, "DNA sequence-dependent compartmentalization and silencing of chromatin at the nuclear lamina," Cell 149:1474-87 (2012).

\* cited by examiner

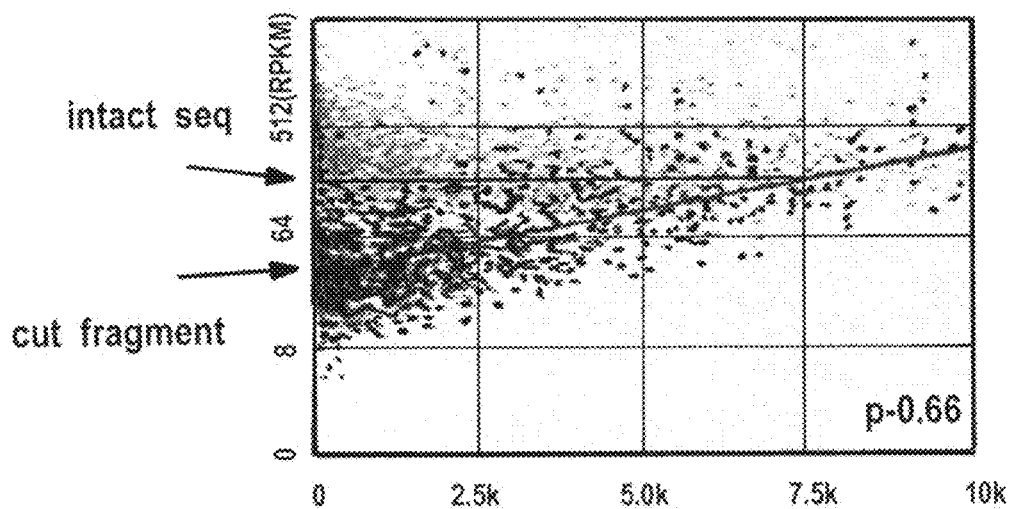
FIG. 1A
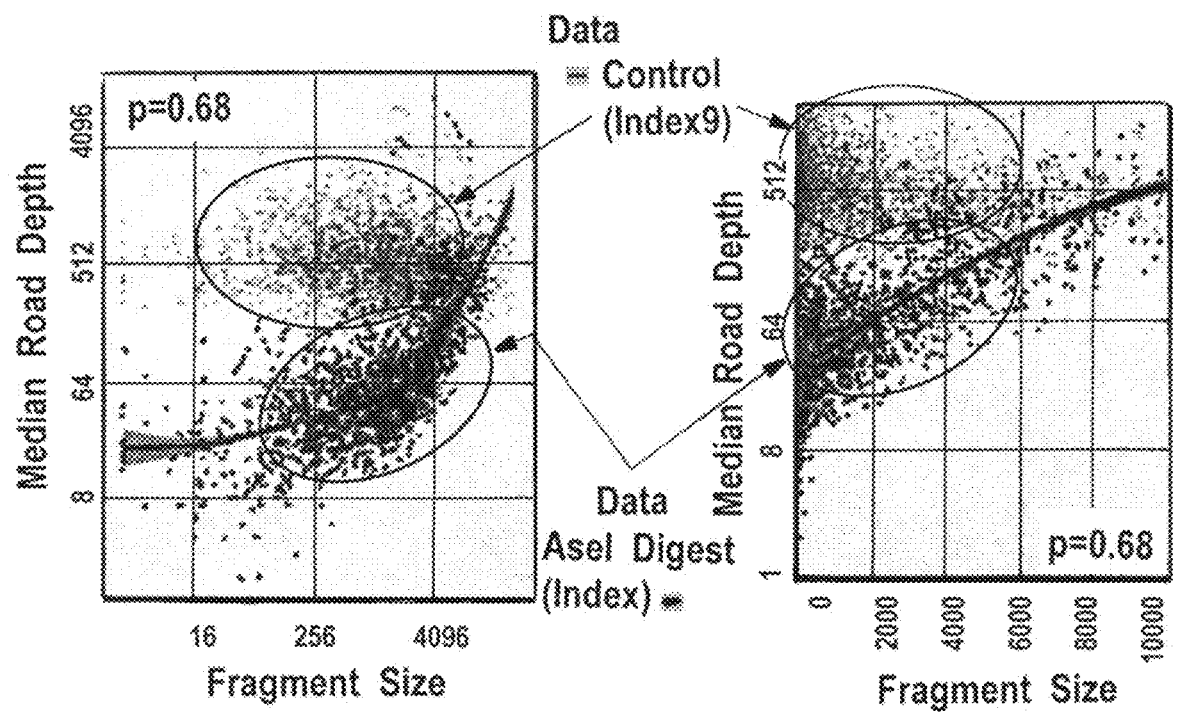
FIG. 1B
FIG. 1C

FIG. 3A
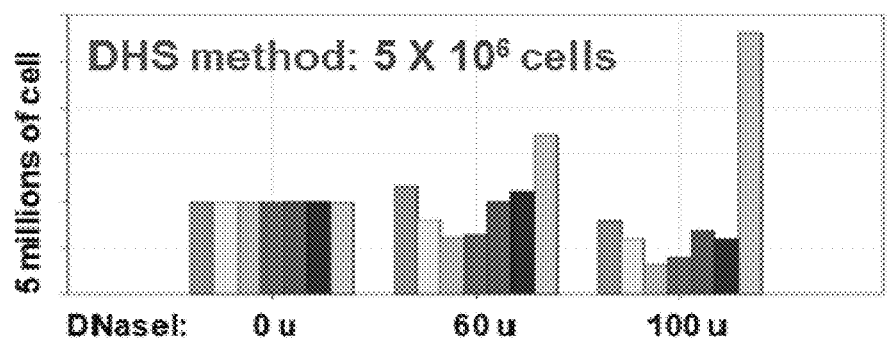
FIG 3B
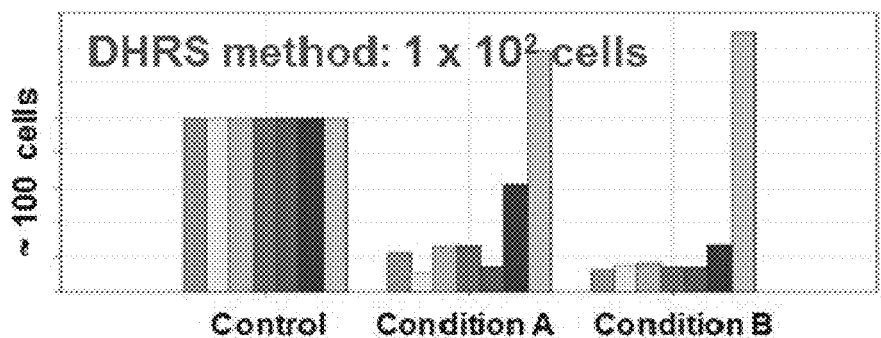
FIGS. 3A-3B
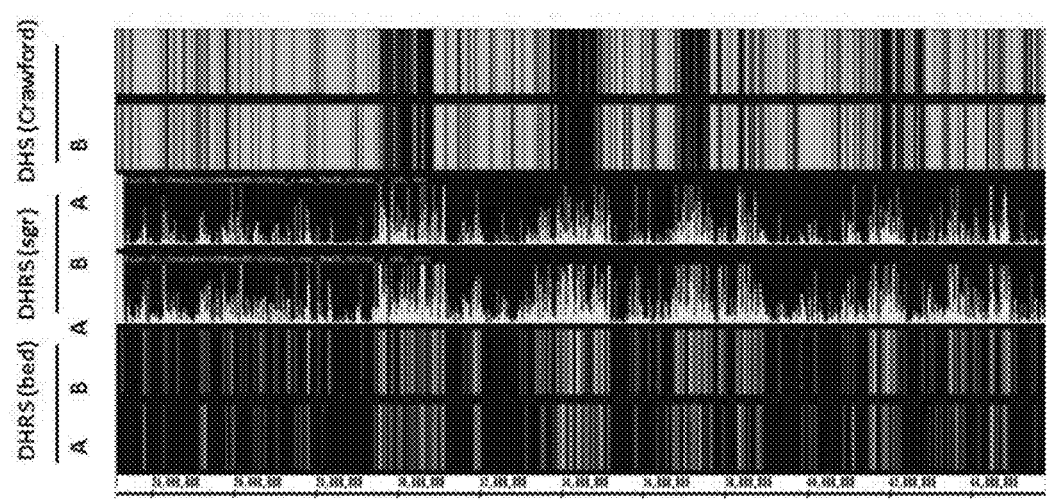
FIG. 4

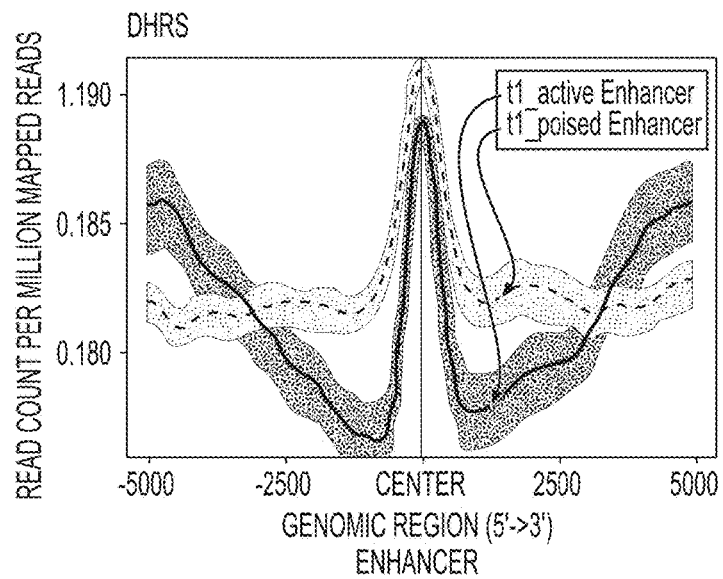
FIG. 8A
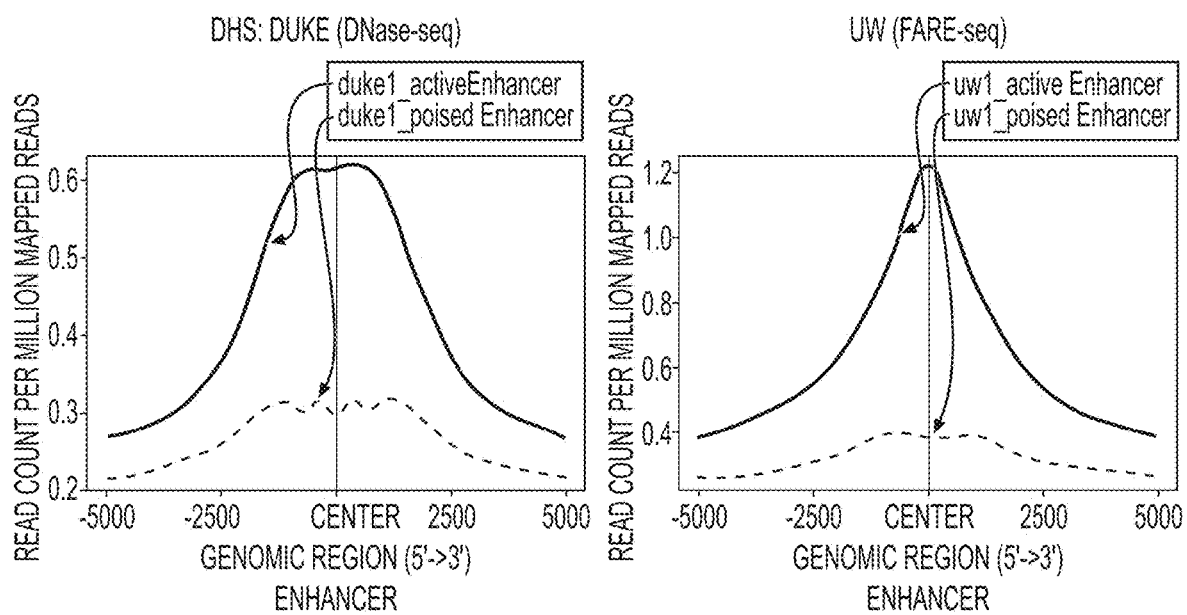
FIG. 8B
FIG. 8C

Insulator

Histone Modifications

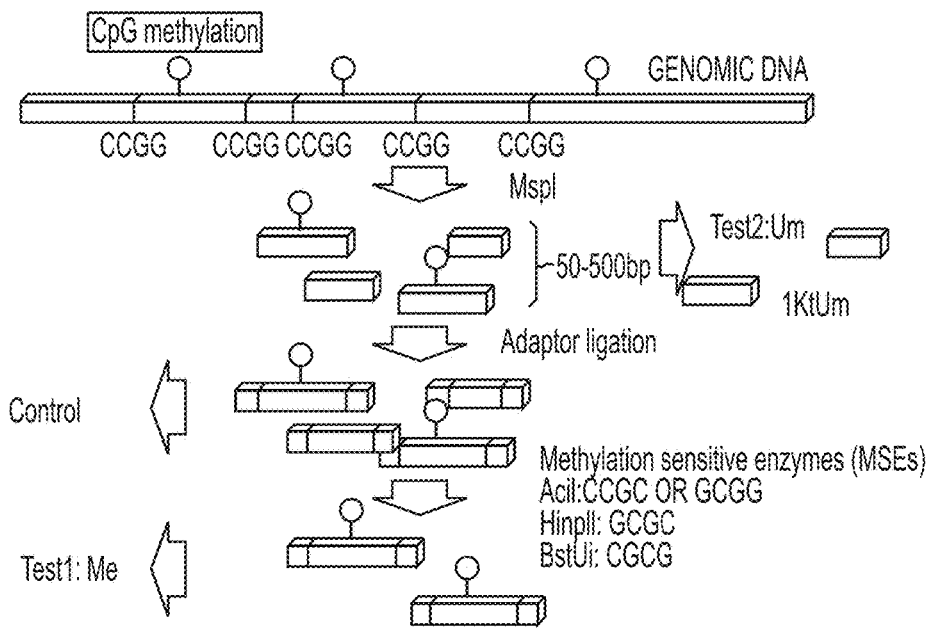
FIG. 17B
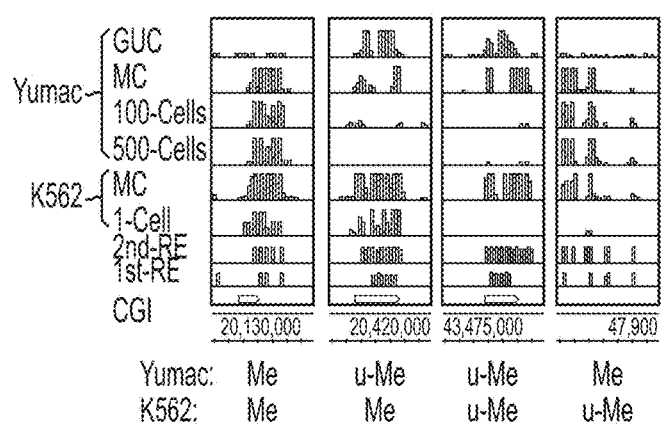 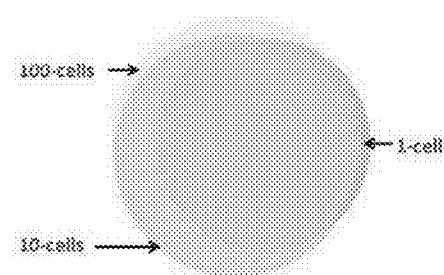
FIG. 18A      FIG. 18B

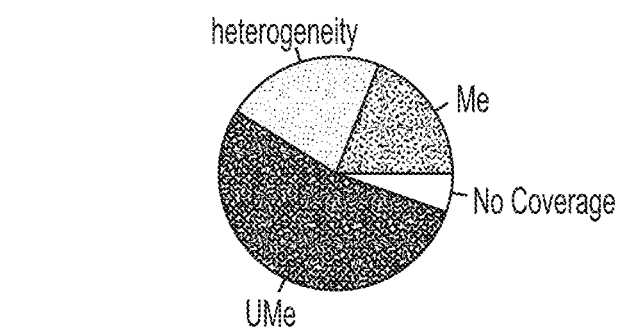
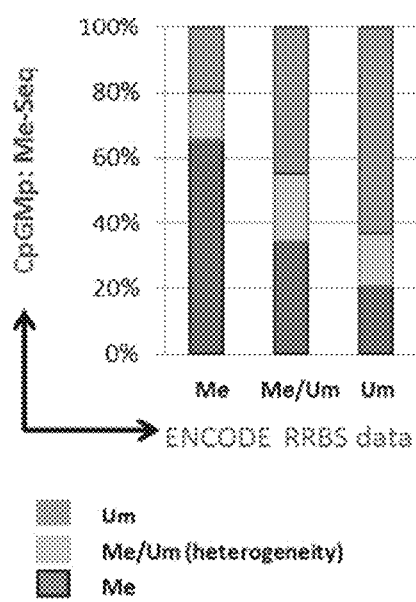
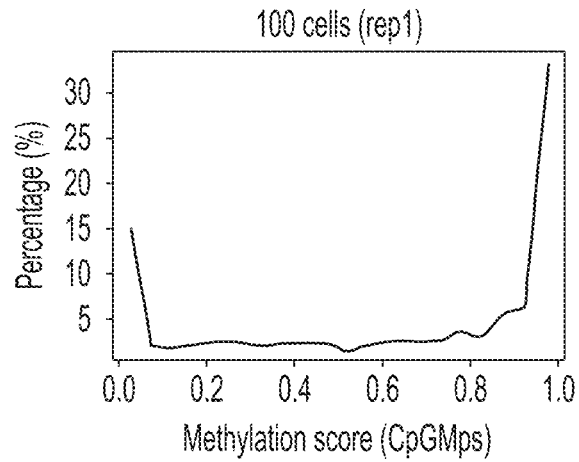
FIG. 19A  FIG. 19B  FIG. 19C

METHODS FOR CLOSED CHROMATIN MAPPING AND DNA METHYLATION ANALYSIS FOR SINGLE CELLS

STATEMENT REGARDING FEDERALLY SPONSORED RESEARCH

This invention was made with government support under 1R21HD066457-01, 1P01GM099130-01 and R01DK100858 awarded by the National Institutes of Health. The government has certain rights in the invention.

CROSS REFERENCE TO RELATED APPLICATIONS

This application claims benefit of and priority to U.S. Provisional Patent Application No. 62/015,965 filed on Jun. 23, 2014, and is specifically incorporated by reference in its entirety.

REFERENCE TO SEQUENCE LISTING

The Sequence Listing submitted as a text file named "YU 6377_ST25," created on Jun. 23, 2015, and having a size of 18,258 bytes is hereby incorporated by reference.

FIELD OF THE INVENTION

The field of the invention is generally related to compositions and methods for preparing genomic materials from cells for profiling chromatin architecture and DNA (i.e. CpG) methylation status, particularly when the cells are at very limited quantities, or even single cells.

BACKGROUND OF THE INVENTION

A large body of information has been obtained about the state of the transcriptome, chromatin modifications, and CpG methylation in various cell types (Nguyen, et al., *Nucleic Acids Research*, 29:4598-4606 (2001), Hahn, et al., *PloS One* 6, e18844 (2011), Smallwood, et al., *Nat Genet*, 43:811-814 (2011), Negrotto, et al., *Leukemia*, 26:244-254 (2012), Alelu-Paz, et al., *J Signal Transduct*, 2012:956958 (2012)). However, better technologies for analysis of single cell (and a low number of cells) are still desired.

Chromatin

The maintenance of chromatin architecture is a dynamic and complex process. Broadly speaking, chromatin can be present in either an open state (accessible to transcription factors and other proteins), or in a compacted state. Compact chromatins are often associated with silencing of genes and resistance to DNase I digestion (Francastel, et al., *Molecular Cell Biology*, 1:137-143 (2000), Teif, et al., *Nucleic Acids Research*, 37:5641-5655 (2009)). Chromatin remodeling plays a role in regulating gene expression and in several biological processes, such as DNA replication and repair, apoptosis, development and pluripotency (Wu, et al, *The Journal of Biological Chemistry*, 272:28171-28174 (1997), Clapier, et al., *Annual Review of Biochemistry*, 78:273-304 (2009)). Genome wide chromosome conformation studies (HiC) indicate that, at the megabase level, cellular chromatin can be partitioned into large blocks of relatively open or closed chromatin (van Berkum, et al., *Journal of Visualized Experiments*, JoVE 39, pii: 1869 (2010), Nagano, T., Lubling, et al., *Nature*, 502:59-64 (2013)). At a finer scale level, nuclear lamin associated chromatin may be in a closed configuration (Zullo, *Cell* 149:1474-1487 (2012)).

Studies of the distribution of histone modifications with regard to chromatin architectures on a genome wide scale have led to several generalizations (Wang, et al., *Trends Mol Med*, 13:363-372 (2007), Bell, et al., *Nat Rev Genet*, 12:554-564 (2011), Zhu, et al., *Cell*, 152:642-654 (2013), Song, et al., *Genome Research*, 21:1757-1767 (2011), Geiman, et al., *J Cell Biochem*, 87:117-125 (2002)). Methylation of specific lysine residues such as K9 and K27 in H3 is associated with compaction of chromatin thereby preventing binding of transcription factors to the DNA and gene repression. On the contrary, histone acetylation relaxes chromatin condensation and exposes DNA for TF binding, leading to increase gene expression, and trimethylation of other lysine residues on histone H3 (K4 and K36 trimethylations are associated with actively transcribed genes). The distribution of these patterns of histone modifications is partly cell type-specific with marked differences between, for example, freshly isolated cells and cells maintained in tissue culture, or between ES cells and differentiated somatic cells, etc. There are also regions of DNA devoid of commonly studied histone modifications.

DNase I hypersensitive sites (DHS) in chromatin represent open chromatin sites where canonical nucleosomes are displaced, particularly by other sequence specific DNA binding proteins. They were first mapped over 30 years ago and identified as stable marks of cell differentiation (Weintraub, et al., *Science*, 193:848-856 (1976)). In addition to transcriptome, methylome and chromatin immunoprecipitation (ChIP) studies, with the advent of next generation sequencing (NGS), DHS analysis has been revitalized, refined, and expanded to a whole genome scale (Crawford, et al., *Genome Research*, 16:123-131 (2006), Ling, et al., *Methods in Molecular Biology*, 977:13-19 (2013)). The results of the current generation of DHS studies have helped map promoters and enhancers acting in particular cell types as well as reveal a plethora of potential regulatory regions of unknown function (Degner, et al., *Nature*, 482:390-394 (2012); Mercer, et al., *Nat Genet*, 45:852-859 (2013); Apostolou, et al., *Nature*, 502:462-71 (2013)). A single cell type may have hundreds of thousands of DHS and there is a considerable degree of cell type specificity in the location of these DHS.

Previous efforts to reveal chromatin structure (or chromatin conformation) based on different properties of chromatin have been performed on relatively large populations of cells (Auerbach, et al., *PNAS*, 106:14926-14931 (2009); Henikoff, et al., *Genome Research*, 19:460-469 (2009)). The data was obtained by averaging sites heterogeneously distributed in many different cells, which confounds interpretation of the results.

Nuclease resistant DNA sequences, referred to herein as DHRS (DNase I Hyper-Resistant Sites), reflect chromatin maintained in an inactive state. Individual segments of condensed DNA have been isolated and characterized physically (Wang, et al., *The Journal of Biological Chemistry*, 279:55401-55410 (2004)). DHRS may be involved in active processes for suppressing a gene (Stauffer, et al., *J Cell Sci*, 114:2383-2393 (2001); Martin, et al., *FASEB*, J 24:1066-1072 (2010); Burgess-Beusse, et al., *PNAS*, 99(4):16433-16437 (2002)). Some DHRSes overlap sites of CpG hypermethylation and gene silencing, although DNA methylation in the body of a gene may be associated with active expression rather than silencing (Prioleau, et al., *The EMBO Journal*, 18:4035-4048 (1999), Costello, et al., *Nat Genet*, 24:132-138 (2000), Kashiwagi, et al., *Nucleic Acids Research*, 39:874-888 (2011), Jursch, et al., *Mob DNA*, 4:15 (2013)).

Not all parts of the genome can be simply categorized as DHS or DHRS. More specifically, DHRSes are not just an absence of DNase I hypersensitivity, but are sites of DNase I hyper-resistance that exhibit specific characteristics. Accordingly, previous efforts to map chromatin sites based on DHS analysis alone are generally insufficient. No genome wide-based high resolution study of the distribution of condensed nuclease resistant chromatin regions has been reported, and the direct study of the genomic distribution of compacted chromatin is a relatively unexplored field. Therefore, there remains a need for improved methods of identifying site of closed chromatin and DHRS.

Methylation

Methylation of cytosine in CpG sequences is an important epigenomic modification, which is involved in regulating many cellular processes (Jones, et al., Science, 293: 1068-1070 (2001)). The promoters of more than half of all genes are embedded in CpG islands, and methylation of the islands correlates strongly with gene silencing. Aberrant methylation has been shown to correlate with a number of disease processes affecting embryonic and later development. Examples include uniparental disomy for chromosomes 6 and 7 (Russell Silver syndrome), chromosome 11 (Beckwith-Wiedemann syndrome), chromosome 14, 15 (Prader-Willi and Angelman syndromes (Schimmenti, et al., Genetics in Medicine, 13: 1006-1010 (2011)), chromosome 16, and 20 (Eroglu, et al., Seminars in reproductive medicine, 30: 92-104 (2012); Binder, et al., Clinical endocrinology & metabolism, 25(1):153-60 (2011); Moreira-Pinto, et al., Fetal Pediatr Pathol., 31(6):448-52 (2012)). Methylation screening in newborns may also detect environmental exposure of the fetus in utero to harmful elements such as smoking, stress, and toxic chemicals (arsenic, polycyclic aromatic hydrocarbons).

Abnormal methylation is a marker for mutations that silence genes. Trinucleotide expansions, which are not well detected by short-read, high-throughput sequencing often result in gene silencing through promoter methylation. For example, examining the CpG islands of the Fragile X gene and others may be an alternative method of identifying this type of mutation (Sheridan, et al., PLoS One, 6(10):e26203 (2011)). As an exploratory study, cataloguing global methylation in phenotypically characterized newborns could identify aberrant patterns that reflect additional genetic or epigenetic disorders currently unrecognized.

Several methods have been applied to analysis of global cytosine methylation in the human genome. Methylation-sensitive restriction enzymes (MSREs) have been used to map the methylation status of an informative subset of CpG cluster (Estecio, et al., Genome Res, 17, 1529-1536 (2007); Shann, et al., Genome Res, 18, 791-801 (2008)). DNA immunoprecipitation with methyl C binding proteins (MceP2 or MBD) (Fuks, et al., The Journal of Biological Chemistry, 278, 4035-4040 (2003); Kangaspeska, et al., Nature, 452, 112-115 (2008)), and antibody capture of the methylated-C containing DNA fragments or methylated DNA immunoprecipitation (MeDIP) (Weber, Nature Genetics, 39: 457-466 (2007); Koga, et al., Genome Res, 19, 1462-1470 (2009)) have also been widely applied. Other studies utilizing MeDIP (Pelizzola, et al., Genome Res, 18, 1652-1659 (2008)), MSRE (Yasukochi, Y. 2010, PNAS, 107, 3704-3709) and MBD to analyze CpG methylation patterns indicate that none of these methods confidently determines if a given CpG site is methylated or not. Furthermore, each of these methods requires relatively large amounts of DNA.

A popular method for genome wide DNA methylation (methylC) analysis is to deaminate unmethylated cytosines, then compare the DNA sequence with that of the untreated DNA, which is achieved by using bisulfite treatment and sequencing. Genome wide methylC-seq covers all Cs in a genome but requires several lanes on HiSeq2000 to evaluate one sample with sufficient depth. It is not financially practical as a clinical test using current technology.

Alternatively, reduced representative bisulfate sequencing (RRBS) detects most of the CpGs in the CpG islands and promoters with a cost of about 2% of full methylC-seq (Gu, et al., Nat Protoc, 6, 468-48 (2011)). The drawback is that conventional RRBS, like methyl-seq, requires not only a high quantity but also high quality genomic DNA. Deamination must be done on the input DNA rather than on amplified samples, so as not to lose methylation marks during amplification. This procedure involves too many steps with too much potential for DNA loss to be applicable to single cells using current methodology.

Because conventional methods rely on large quantities of genomic DNA, genomic distribution of DNA CpG methylation most typically relies on pooled DNA from many cells. Studies indicate that dramatic changes in DNA methylation occur during germ cell formation and early development of the fertilized egg (Dobbs, et al., PloS one 8, e66230 (2013), Smith, et al., Nature, 484:339-344 (2012)). Differences in methylation patterns of somatic tissues are more restricted (Chen, et al., The Journal of Biological Chemistry, 286: 18347-18353 (2011)). Methylation also increases in aging hematopoietic stem cells, and may contribute to the aging phenotype (Bocker, et al., Blood 117, e182-189 (2011), Hodges, et al., Molecular Cell, 44:17-28 (2011), Hogart, et al., Genome Research, 22:1407-1418 (2012), Beerman, et al., Cell Stem Cell, 12:413-425 (2013)).

However, most of this information is derived from tissues or organs that are composed of a mixture of a variety of cell types. Even when cell lines are examined, it is unusual to separate cells according to the stage of the cell cycle or to take account of potential circadian effects on gene expression. Therefore, the results of the studies are most typically are actually an average of values for a large, heterogeneous cell population, and may not accurately reflect the state of any homogeneous subpopulation or individual single cells. This is especially true for histone modification studies including ChIP-seq or DHS studies that usually require millions of cells. The most sensitive protocol for ChIP-seq (Adli, et al., Nature Methods, 7:615-618 (2010), Adli, et al., Nature Protocols, 6:1656-1668 (2011)) needs no less than 10,000 cells, and has not yet been widely applied.

Recently, efforts have been focused on global transcription analyses of single cells (Tang, et al., Nature Protocols, 5:516-535 (2010); Islam, et al., Genome Research, 21:1160-1167 (2011); Hashimshony, et al., Cell Rep, 2:666-673 (2012); Yan, et al., Nature Structural & Molecular Biology, 20:1131-1139 (2013); Farlik, et al. Cell Reports, 10(8): 1386-97 (2015). These methods have confirmed heterogeneity in the types of cells present in what had been previously presumed to be relatively homogeneous cell preparations (Sasagawa, et al., Genome Biol, 14:R31 (2013)), in the distribution of splice isoforms among cells (Shalek, et al., Nature, 498:236-240 (2013)), and in the response of cells to various stimuli. In some cases, such as hematopoietic multipotential precursors, the heterogeneity is remarkably extensive, requiring a new level of description for lineage differentiation (Gibbs, et al., Blood, 117:4226-4233 (2011), Mills, et al., Blood, 122:2047-2051 (2013)). Despite recent efforts, there remains a lack of suitable methods for determining single cell level DNA methylation (Guo, et al., Genome Res., 23(12):2126-35 (2013)).

Accordingly, improved methods for analyzing chromatin architecture and methylation status, particular in small quantities of cells and in single cells are needed.

Therefore, it is an object of the invention to provide sensitive methods for identifying sites of closed chromatin and/or DNase I Hyper-Resistant Sites (DHRS) in the genome of cells.

It is also an object of the invention to provide sensitive methods for determining if CpG-rich regions such as CpG islands and CpG island shores in the genome of cells are methylated or unmethylated.

It is also an object of the invention to provide methods for identifying differentially methylated regions (DMR) and determining if they are methylated and unmethylated.

It is a further object of the invention to provide methods for improved method of sequencing DNA at single nucleotide resolution after bisulfite conversion.

It is a further object of the invention to provide methods for analysis of chromatin and methylation status that are suitable for use on limited genomic DNA, for example DNA from a few or even a single cell.

It is another objection of the invention to provide methods for reducing or preventing random or non-specific strand breakage or damage or loss of genomic DNA that can occur when genomic DNA is isolated, or accessed or processed from cells, particularly small quantities of cells.

It is a further object to the invention to employ the improved methods of isolating, accessing, and or processing genomic DNA in methods that include amplifying genomic sequences.

It is further object of the invention to provide methods that can be carried out partially or completely in a single tube.

SUMMARY OF THE INVENTION

As discussed in Example 1 and illustrated in FIGS. 1A-1D, it has been discovered that multiple displacement amplification, for example, phi29 DNA polymerase-based amplification, selectively enriches larger fragments in a DNA pool over shorter fragments (e.g., <3-4 kb, or roughly ~3.5 kb). Shorter fragments are depleted and larger fragments can be selectively recovered, even when the total DNA material is very limited. This principle has been utilized to develop a number of methods useful for preparing profiles of chromatin architecture and methylation status of the genome of a single cell or a population of cells. Variations on the methods utilizing PCR-based amplification in place of MDA are also provided.

Methods of identifying site of closed or compact chromatin and/or DNase I Hyper-Resistant Sites (DHRS) are disclosed. The methods typically include digesting genomic DNA with DNase I or other endonucleases (such as micrococcal nuclease or MNase, Kuribayashi, et al., *Anticancer Res.*, 16(3A):1225-30 (1996)), or other biological materials (such as transponsons, (Buenrostro, et al., *Nature Methods*, 10: 1213-1218 (2013)), or by other chemical/physical means of disruption, for example, sonication (Auerbach, et al., *PNAS*, 106(35):14926-31 (2009), nebulization, or hydroshearing process. Next the digested DNA is amplified by MDA to produce amplicons. The amplicons are representative of closed or compact chromatin and/or DHRS because the closed or compact chromatin and/or DHRS DNA are present in relatively intact or long DNA fragments. In some embodiments, the sequences of the amplicons are determined, for example by sequencing the amplicons. The sequenced amplicons (i.e., compact chromatin and/or DHRS) can be mapped to the sequence of the genomic DNA. As discussed above, DHRS regions have important biological significance. In some embodiments, the DHRS are verified by a conventional, molecular biology or cell biology method.

Methods for identifying methylated and unmethylated CpG-rich DNA fragments/sequences, also referred to as differentially methylated regions (DMRs), are also provided. The methods can generally be categorized by an initial amplification step which is mediated by either MDA or polymerase chain reaction (PCR). The amplification allows highly methylation and highly unmethylation DMRs to be distinguished from one another. Therefore, the disclosed methods include a technique or step prior to amplification that allows the amplicons, or sequences thereof to be distinguished as methylated or unmethylated DMRs after amplification.

For example, in some embodiments, methylated DMRs are identified by digesting genomic DNA with one or more MSREs; amplifying the remaining, un-digested DNA (with highly methylated CpG) by MDA to produce amplicons. In preferred embodiments the one or more MSREs make rare or infrequent cuts in the genomic DNA. The sequences of the DMRs can be determined, for example by sequencing the amplicons. The sequences can be mapped to the genome.

A method of identifying unmethylated DMRs can include identifying methylated DMRs; mapping the methylated DMRs to the sequence of the genomic DNA; determining that DMRs that are not identified as methylated are unmethylated DMRs by comparing the identified methylated DMRs to whole collection of candidate DMRs (cDMRs) as a reference. The foregoing methods of CpG methylation analysis can be referred to as MSRE cut-MDA amplification (MSRE-MDA) methods.

Another method of identifying methylated and unmethylated DMRs includes digesting genomic DNA with a MSRE to generate fragments of genomic DNA; ligating the fragments of genomic DNA under conditions that drive intramolecular circularization; amplifying the fragments of genomic DNA by MDA to produce amplicons; and determining the sequences of the amplicons, wherein the sequences of amplicons that are deduced to be representations of contiguous genomic DNA sequences crossing the MSRE sites are identified as methylated DMRs; and wherein the sequences of amplicons that are deduced to be representations of non-contiguous genomic DNA sequences (e.g., non-linear DNA assembly sequences) crossing the original MSRE sites are identified as unmethylated DMRs. Such methods can be referred to MSRE cut-ligation-MDA amplification (ML-MDA) methods. An advantage of this strategy is that not only highly-methylated DNA fragments (e.g., methylated DMRs), but also highly un-methylated DNA fragments (e.g., unmethylated DMRs) can be sequenced and detected. This can be a more stringent method because it can reduce, minimize, and/or prevent the chances of falsely categorizing a fragment as unmethylated simply because it is not identified as methylated as in MSRE-MDA. Another advantage of ML-MDA is that it allows for the detection of both CpG methylation profile and genomic mutation profile (including exome-seq or whole-exome-seq (referred as WES), and whole genome sequencing (referred to as WGS) at high depth sequencing or low depth sequencing or shallow seq) for a single sample, or even a single cell. In this case, after MDA amplification, the amplicon can be divided into 2 or more aliquots: one aliquot is subjected to CpG methylation profiling, while other aliquots can used for whole genome sequencing (WGS), the exome capture and sequencing (WES), and shallow WGS for detection of copy-number variations (CNVs).

Circularization can be performed by double strand DNA (dsDNA) ligation (dsDNA circularization) or single strand DNA (ssDNA) ligation (ssDNA circularization). Conventionally, dsDNA circularization is carried out by variants of T4 DNA ligase, including thermostable T4 DNA ligase. For an efficient T4 DNA ligase, dsDNA fragments should be at least 100 bp (with a low efficiency), or longer, with a preferred size being about 400 bp (Travers, et al., Current Biology, 15(10), R377-R379, May 24, 2005), however smaller and larger fragments can also be used. Fragments that are too long can also be less efficiently ligated. Low concentrations of the DNA template can drive intra-molecular DNA ligation or circularization. To improve the efficiency of ligation, the ligation can be performed at a relatively low temperature (e.g., at 16° C.) for a relatively longer time. PEG (e.g., PEG8000, PEG4000, etc.) or another matrix can also be added to the reaction mixture to improve the ligation efficiency when the template concentration is low. The ssDNA ligase, CircLigase-ssDNA ligase or CircLigase-II ssDNA ligase show an exclusive intra-molecular DNA circularization for the template as short as 10 bases and as long as kilo-bases. However, the template has to be single stranded, and the ligation efficiency varies corresponding to the nucleotide constitution and combination of 5' and 3' terminal, when the reaction is performed at 60° C. The variation in the ligation efficiency, and particularity the low efficiency of ligation for certain terminals of the ssDNA, can be modulated to improve results.

Methods of identifying methylated and unmethylated DMRs using a PCR-based amplification step are also provided. For example, a method of identifying methylated DMRs can include digesting genomic DNA with a methylation insensitive and CpG island-enriched restriction enzyme, such as MspI, or another methylation insensitive biological, chemical or physical fragmentation technique that can generate short fragments of CpG rich sequences that are within a size range suitable for amplification by conventional PCR and sequencing; ligating an amplification adaptor including a PCR primer binding site to the 5' ends of the fragments of genomic DNA; extending the adapter to form full double stranded fragments and remove adapter-dimer-orientated-template; treating the fragments with one or more MSREs, such as BstUI, AciI, Hinp1I, and/or HpaII (if MspI is not used for fragmentation in the early step); amplifying the MSREs uncut fragments by PCR including extension of primer(s) that bind to PCR primer binding site in the amplification adaptors to produce amplicons that are representative of methylated DMR; and determining the sequences of the amplicons. Such methods can be referred to Fragmentation (such as Non-MSRE cut, and particularly such as MspI cut)-Adapter ligation-MSRE-PCR amplification (FAM-PCR) methods. These methods are based on a positive identification of highly methylated CpGs, or Mm-CpG.

Unmethylated DMR can be determined by subtracting the methylated DMR from a control collection of potential DMR. Such methods can include identifying unmethylated DMRs by identifying methylated DMRs; mapping the methylated DMRs to the sequence of the genomic DNA; and identifying DMRs that are not identified as methylated as unmethylated regions using the control collection of cDMRs as the reference.

In another embodiment, a method of directly identifying unmethylated DMRs includes digesting genomic DNA with a MSRE to discriminate DNA sequences with highly methylated and highly unmethylated CpGs and generate fragments of genomic DNA; ligating an amplification adaptor including a PCR primer binding site to the 5' ends of fragments of genomic DNA; extending the adapter to form a fully double stranded adaptor and remove adapter-dimer-orientated-template; amplifying the cut (un-methylated) fragments by PCR including extension of primer(s) that bind to PCR primer binding sites in the amplification adaptors to produce amplicons; and determining the sequences of the amplicons, which are representative of highly un-methylated fragments. Such methods can be referred to MSRE-Adapter/ligation-PCR amplification (MSRE-Adapter-PCR or MA-PCR) methods. These methods are based on positive identification of highly un-methylated CpGs (Um-CpG), and because one less step is involved, can be more robust for single cell CpG methylation profiling than FAM-PCR based methods.

A method of identifying methylated DMRs can therefore include identifying unmethylated DMRs; mapping the unmethylated DMRs to the sequence of the genomic DNA; and identifying DMRs that are not identified as unmethylated as methylated using control collection of cDMRs as the reference.

The adapter used in the PCR-based methods typically contains a longer, full-length oligonucleotide to which a shorter (less than full length) oligonucleotide is hybridized at the 3' end of the full length oligonucleotide. The full-length oligonucleotide is covalently ligated to the 5' ends of the genomic DNA fragments. The short oligonucleotide is melted off before DNA polymerase is used to fill in the strand complementary to the longer oligonucleotide by extending the 3' end of the DNA fragment using the full-length oligonucleotide as the template.

The adaptor ligation step of the PCR-based methods can include a single-strand-covalent-ligation between the adapter and the 5' ends of genomic DNA fragment, follow by Sulfolobus DNA polymerase IV (5'-3' exo, and no strand displacement), Klenow fragment (5'-3' exo−) polymerase or Taq DNA polymerase driven fill-in of single stranded regions in the adapter to form a fully double stranded adapter, before the $1^{st}$ step of denaturation of PCR.

In some embodiments, the methods are coupled to a method of bisulfite sequencing and/or mutation analysis. In a particular embodiment the bisulfite sequencing is RRBS (reduced representative bisulfite sequencing) (FIG. 20). A modified ultra-sensitive (us) RRBS method, also referred as usRRBS, is therefore, provided and can be used to analyze a small number of cells, including single cells. For methods including usRRBS, the cytosines (Cs) in the long oligonucleotide of the adaptor are all methylated. The original short oligonucleotide need not be methylated the C's, because is not part of the final fragment. However, the step of filing-in the region complementary to the long full length is carried out with methylated cytosines in the sequences, for example by providing methylC (dmCTP, sGTP, dATP and dTTP) during the extension process.

An alternative design is that both the longer full length oligonucleotide and the short oligonucleotide are un-methylated at every "C" of all of the "C" sites. And during the extension/filling-in step, 4 conventional nucleotides (dATP, dTTP, dGTP and dCTP) are provided. The sequences of the 2 oligonucleotides are designed such that after bisulfite conversion (when it applies), the PCR primers are exactly matching the bisulfite converted product, and after PCR amplification, the amplicon sequences corresponding to the adapters have a recognition site for a type IIs site, preferably BciVI site.

A multiplex design can be integrated into these PCR-based methods for CpG methylation profiling above, particularly the FAM-PCR, MA-PCR and usRRBS. The key for the multiplex design is a barcoded adapter that with a barcode (a combination of nucleotides) built in that are directly ligated to the initial MSRE digested fragment end. After ligation, and with (FAM-PCR) or without (MA-PCR) additional treatment, the samples can be combined or pooled together like one sample for the downstream processes.

The sequence of amplicons produced by the methods disclosed herein can be determined using any suitable method, for example, Sanger sequencing, next generation sequencing (NGS), or microarray hybridization. NGS is a preferred method for genome-wide mapping of the sequences. The sequence information can be mapped to the genome to prepare a chromatin or methylation profile. However, it will also be appreciated, as discussed in more detail below, that determining the sequence of the amplicons by sequencing is not necessary or required. For example, in some embodiments, the amplicons are analyzed by PCR and Sanger sequencing. The method is particularly useful if only limited pieces of sequences are needed. In some embodiments, sequence information of the amplicons is not obtained by direct sequencing and analysis of the amplicons using an alternative non-sequencing based method is used to generate a profile or otherwise characterize the chromatin or methylation status for a targeted portion of the genome or genome-wide.

Methods of preparing a profile of the chromatin architecture of genomic DNA are also provided. An exemplary method includes identifying DHRS, identifying DHS, or a combination thereof, and mapping the DHRS and/or the DHS to the sequence of the genomic DNA.

Methods of preparing a profile of methylation status of genomic DNA also disclosed. An exemplary method includes identifying highly methylated DMRs, identifying highly unmethylated DMRs, or a combination thereof, and mapping the methylated and/or unmethylated regions to the sequence of the genomic DNA.

For the CpG methylation mapping methods, in a preferred embodiment, particularly when an adapter ligation after RE digestion is required at an early step, lysing of cells to obtain or access genomic DNA is carried out under conditions that reduce, minimize, and/or prevent double strand dissociation (e.g., to single strands). In some preferred embodiments, particularly when selection of RE cut DNA fragments are required (e.g., PCR-based CpGmp method such as FAM-PCR, MA-PCR, and usRRBS), DNA is isolated or accessed or processed under conditions that reduce, minimize, and/or prevent non-specific or random shearing, or damage or loss of the genomic DNA. Accordingly, any of the methods can include accessing or isolating genomic DNA under conditions that maintain double strandedness of the genomic DNA, reduce, minimize, and/or prevent non-specific shearing of the DNA, or a combination thereof. In some embodiments, the methods are carried out in a single tube at least through a first amplification step.

cDMR are typically can be determined independently for each different methodology using a corresponding control assay, which can be carried out in parallel. In some embodiments, the identification of cDMR is carried out on genomic DNA from a control population of cells. The cells can be of the same cell type as the cell or cells being analyzed in the test assay (i.e., the assay that determines if the DMR is methylated or unmethylated). In some embodiments, one or more of the restriction digestions in the control assay is conducted using the same enzyme(s) as is used in one or more steps of the corresponding test assay.

In some embodiments, the candidate DMR (cDMR) should be generated with the same RE set as its counterpart test assay, but the MSRE(s) cannot cut all genomic DNA because some regions are blocked from cutting by methylation. Therefore, in some embodiments, for assay for identifying or preparing cDMR, the genomic DNA is first amplified, for example using MDA. The methylation is lost from the amplified DNA, making all the DNA non-methylated DNA (i.e., substantially diluting the methylated DNA which is only the original template DNA). Therefore, all the recognition sites within the genomic DNA will be cut by the RE or MSREs, because none of the sequences will be blocked by methylation. Accordingly, the same set of RE or MSRE can be used to generate the methylated or unmethylated DMRs and to make them comparable, using subtractive analysis, from candidate DMRs, regardless of which one (methylated DMR or unmethylated DMR) is determined empirically and which is determined by subtraction.

As discussed in more detail below, the disclosed methods can be used to prepare profiles for low quantities of cells, for example 10,000 or fewer cells, 1,000 or fewer cells, 100 or fewer cells, 10 or fewer cells, or even a single cell.

The methods disclosed herein can be used in a wide range of applications including drug discovery and development, diagnostics, and treatment.

BRIEF DESCRIPTION OF THE DRAWINGS

FIGS. 1A-1C are scatter plots showing the MDA efficiencies (reads per kilo base per million (RPKM)) correlated to DNA fragments (size in kb) from the *E. coli* genome with AseI digestion (ATTAAT cut fragments) or without digestion (control, intact seq).

FIGS. 3A and 3B are bar graphs showing DHRS analysis with ~100-cells (3B) versus conventional DHS analysis (3A) with $5\times10^6$ cells K562, evaluated with qPCR with previously known DNase I resistant sites (further right hand bar (bar 7) in each of the three clusters) and DHS sites (first 6 bars from the left in each of the three clusters). Three clusters of bars from left to right represent control and two different experimental conditions for each technique (3A and 3B).

FIG. 4 is chromatin profile of DHRS treated DNA sequenced on an Illumina HiSeq 2000 and compared to DHS data from the UCSC ENCODE database. The sequencing result was converted into sgr files and mapped using Integrated Genome Browser (IGB).

FIG. 8A is a plot showing DHRS regions (read count per million mapped reads) relative to the location of two known enhancer activities (active and poised). FIGS. 8B and 8C are plots showing the controls: DHS regions (read count per million mapped reads) relative to the location of two known enhancer activities (active and poised) for two known data sets: Duke (DNase-seq) (8B) and UW (FARE-seq) (8C). The active enhancers are enhancers linked to the genes that are actively being transcribed into RNA, and the poised enhancers refer to the enhancers showing an inhibited activity.

FIG. 17B is a diagram illustrating exemplary bioinformatic considerations for isolating and amplifying methylated DMRs and unmethylated DMRs and some of the various points at which the assays can be varied to customize the results.

FIG. 18A is a sequencing profile showing the results of a MSRE/digestion-MDA (MSRE-MDA) method used to identify methylated and unmethylated DMRs. FIG. 18B is a Venn diagram showing the correlation between detecting a methylated or unmethylated DMR using 1, 100, or 500 cells starting material.

FIG. 19A is a bar graph showing results for ummethylated regions (Um), heterogeneous regions (Me/Um), and methylated regions (Me) obtain by Me-Seq in comparison to results available in the ENCODE RRBS data for the same cell line K562. FIG. 19B is a pie chart summarized the distribution of methylated, unmethlylated, heterogenous, and no coverage regions as determined by Un-Seq (MA-PCR). FIG. 19C is a line graph showing the percentage (%) as a function of methylation score (CpGMps) as determined by Um-Seq (FAM-PCR).

DETAILED DESCRIPTION OF THE INVENTION

I. Definitions

Figure 1D:
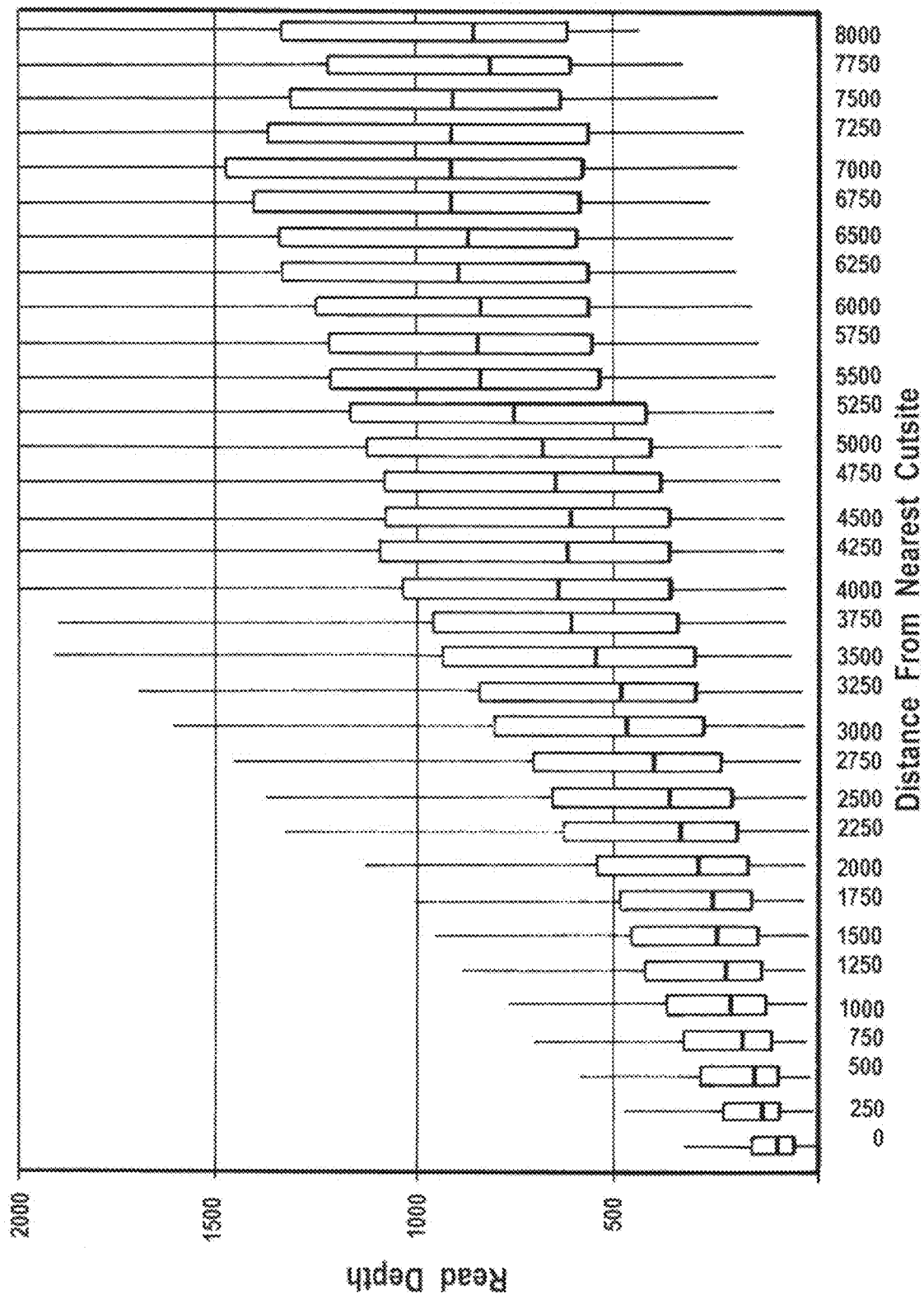
FIG. 1D is a bar graph showing the sequencing read depth of amplicons following MDA as a function of the distance from the near cut site.

"Isolated," "isolating," "purified," "purifying," "enriched," and "enriching," when used with respect to nucleic acids of interest (e.g., DNA such as intact or fragmented genomic DNA, amplicons, etc.), indicate that the nucleic acids of interest at some point in time were separated, enriched, sorted, etc., from or with respect to other cellular material to yield a higher proportion of the nucleic acids of interest compared to the other cellular material, contaminates, or active agents such as enzymes, proteins, detergent, cations or anions. "Highly purified," "highly enriched," and "highly isolated," when used with respect to nucleic acids of interest, indicates that the nucleic acids of interest are at least about 70%, about 75%, about 80%, about 85%, about 90% or more, about 95%, about 99% or 99.9% or more purified or isolated from other cellular materials, contaminates, or active agents such as enzymes, proteins, detergent, cations or anions. "Substantially isolated," "substantially purified," and "substantially enriched," when used with respect to nucleic acids of interest, indicate that the nucleic acids of interest are at least about 70%, about 75%, or about 80%, more usually at least 85% or 90%, and sometimes at least 95% or more, for example, 95%, 96%, and up to 100% purified or isolated from other cellular materials, contaminates, or active agents such as enzymes, proteins, detergent, cations or anions.

As used herein, the term "amplicon" refers to product of amplification, for example, by MDA or polymerase chain reaction (PCR). "Amplicons" can refer to a homogenous plurality of amplicons, for example a specific amplification product, or a heterogenous plurality of amplicons, for example a non-specific or semi-specific amplification product.

As used herein, "CpG site" refers to a narrow region (e.g., a short stretch) of DNA or oligonucleotide sequence that contains a cytosine nucleotide next to a guanine nucleotide in the linear sequence of bases along its length. CpG is the dinucleotide, C followed by G, shorthand for -C-phosphate-G-, that is, cytosine and guanine separated by only one phosphate. Cytosines in CpG dinucleotides can be methylated to form 5-methylcytosine.

As used herein, the term "CpG island" (or CG island, or CGI) is a region with a high frequency of CpG sites. A CpG island is a region with at least 200 bp, and a GC percentage that is greater than 50%, and with an observed-to-expected CpG ratio that is greater than 60%. The "observed-to-expected CpG ratio" is calculated by formula ((Num of CpG/(Num of C×Num of G))×Total number of nucleotides in the sequence) (Gardiner-Garden, et al., *Journal of Molecular Biology*, 196(2):261-82 (1987)). In mammalian genomes, CpG islands are typically about 300-3,000 base pairs in length.

As used herein, the term "CpG island shore" refers to DNA sequence that occur up to about 2 kb distant from a CpG island (Irizarry, et al., *Nature Genetics*, 41(2): 178-186 (2009)). "CpG island" and "CpG island shore" are usually CpG rich sequences.

As used herein, the term "differential methylated region" or "DMR" refers to a genomic region (e.g., a stretch of gDNA) that can have different methylation statuses among multiple samples (tissues, cells, individuals or others). The regions can be, or can include, functional regions involved in gene transcriptional regulation. The region typically is or includes a CpG rich sequence, and is often within a "CpG island" or/and "CpG island shore" or/and other CpG rich sequences such as a promoter. Methylated-DMR may be referred to as Me-DMR, Me-CpG, or Me, and the unmethylated-DMR may be labeled as Um-DMR, Um-CpG, or Um or U-Me. CpG typically refers to CpG-rich DNA stretch (CpG-rich DNA fragment), or CpG island or CpG island shore, or sometimes it may refer to a "CpG" dinucleotide.

With respect to the disclosed polynucleotide sequences, "N" can be any nucleotide (e.g., A or G or C or T); "R" is a purine (e.g., A or G); "Y" is a pyrimidine (e.g., C or T); "W" is an A or T.

II. Methods for Mapping Chromatin Structures

Within cells, chromosomal DNA associates with histones, forming an organized complex known as chromatin. Chromatin enables DNA to be packaged into a smaller volume so that it fits compactly within a cell's nucleus, and it also helps regulate gene expression. Specifically, compaction of the genome in the form of chromatin limits genes' accessibility to transcription factors (and therefore also to DNase, transponson, or even physical shearing of the DNA).

In order for gene expression to occur, changes in chromatin structure, called chromatin remodeling, must take place. These changes are brought about primarily by biochemical modifications to histones, including methylation, acetylation, and phosphorylation. Remodeling ultimately results in altered accessibility of transcription factors to regulatory DNA. During this process, the open (euchromatic) regions are rich in Histone H3 acetylated nucleosomes, and the DNAs are looser and more accessible, and are more easily digested by DNase Deoxyribonucleases (DNase) that cleave phosphodiester bonds in the DNA. Regions of closed chromatin (heterochromatic regions) typically have few or no H3 acetylated histones, and the DNA of the region is protected by specifically modified histone(s). In some embodiments, regions of closed chromatin are resistant to digestion by DNase. Such regions can be referred to as DNase hyper-resistant sites (DHRS).

Typically, after treatment with DNase, regions of highly closed chromatin regions, and particularly DHRS, relatively long DNA fragments, while open regions including DNase sensitive regions (DSR) are sensitive to DNase and therefore cut into small fragment. It has been discovered that MDA selectively amplifies long DNA fragments, while when the DNA is <3-4 kb, the amplification efficiency is reduced, and negatively correlates with reducing fragment length (FIG. 1). As discussed in more detail below, the longer segments of DNA typically representative of DHRS are relatively highly amplifiable by MDA compared to shorter fragments typically representative of open chromatin and DHS and which are depleted during MDA amplification. When RCA is applied (e.g., where the DNA is circularized), the size typically will show no effect on amplification.

Figure 2:
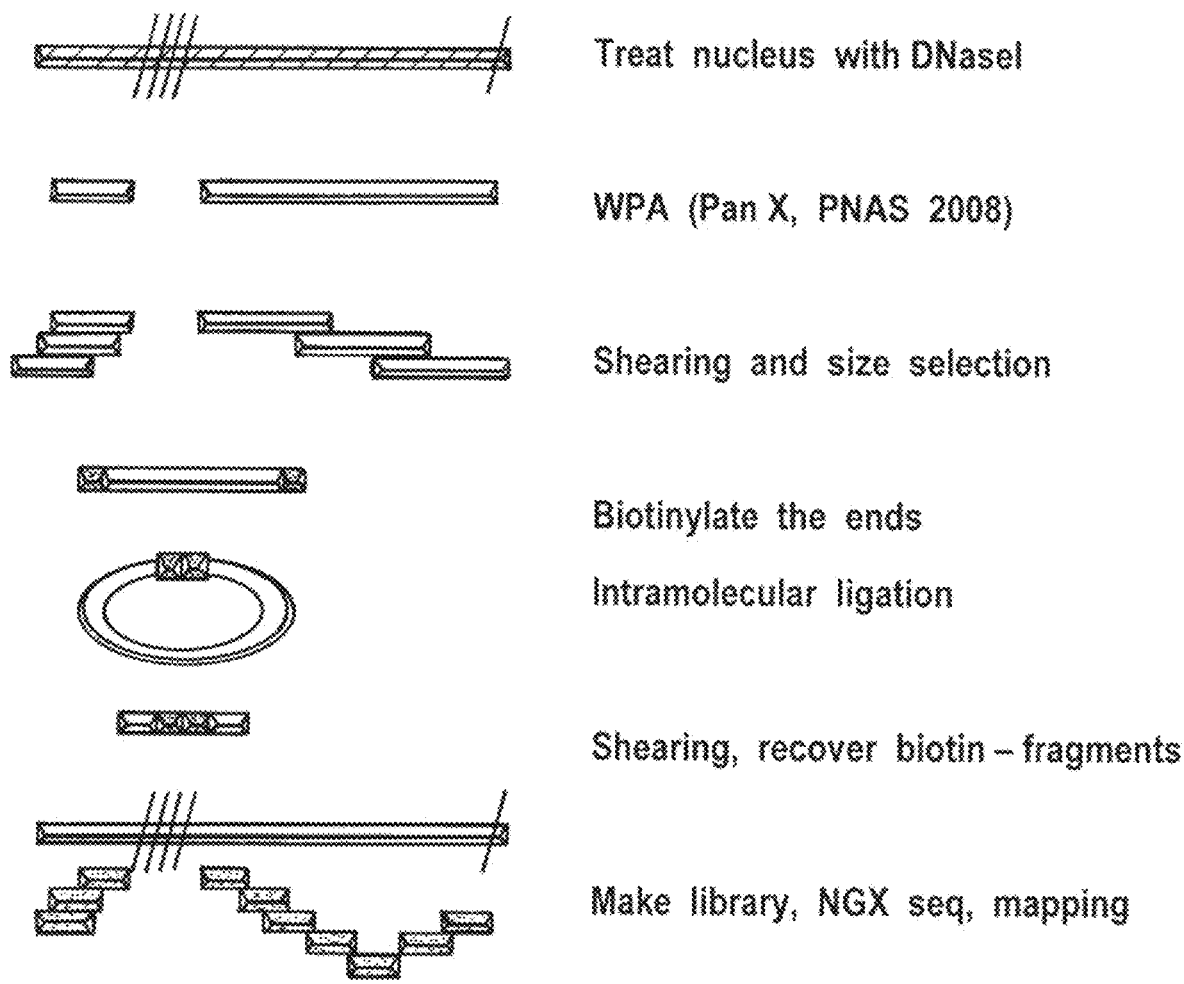
FIG. 2 is a diagram showing a method of preparing a DNase I hyper-resistant site (DHRS) profile that includes steps of treating a nucleus with DNase I, Phi29 polymerase-based MDA (exemplified as WPA), shearing and size selection, biotinylating fragment ends, circularizing fragments, shearing and recovering biotin-fragments, making a library, sequencing the library, and mapping the sequences.

Compositions and methods for preparing chromatin architecture profiles utilizing the foregoing principles are provided. The profiles are typically prepared by identifying DNase I Hyper-Resistant Sites (DHRS), DNase I Hypersensitive Sites (DHS), or a combination thereof in the genome of one or more cells. The methods typically include the steps of accessing open chromatin DNA from one or more cells, digesting the accessible genomic DNA with DNase I or other enzymatic, chemical, and/or physical strategies, amplifying the DNA by MDA to make amplicons, and preparing a chromatin profile by analyzing the amplicons. An exemplary assay is shown in FIG. 2.

A. Preparation of Closed Chromatin—Corresponding DNA Pool

1. Isolation/Access/Separation of Nucleus (or Nuclei) from Cytoplasm

Typically, when working with low quantities of cells, and therefore low quantities of genomic DNA, it can be important to access the genomic DNA under mild or gentle conditions to preserve as much of the desired DNA as possible, and avoid or minimize its loss. In addition, for analysis of closed chromatin and DHRS, it is important to maintain the original native chromatin architecture that is related to nuclear protein binding, while also ensuring that the open chromatin is accessible to the specific treatment that acts on the open chromatin only.

Therefore, typically, the nucleus or nuclei are first isolated from the cytoplasm. In some embodiments, the cell(s) are lysed in 0.1% non-ionic detergent IGEPAL CA-630. The nuclei can be recovered by centrifugation (Crawford, et al, *PNAS*, 101:992-997 (2004)). Following centrifugation, the nucleus (nuclei) can be directly processed accordingly to the following methods of identifying DHRS. It is possible that anchorage to the nuclear membrane might affect susceptibility to nuclease digestion. Therefore, in some embodiments, urea, for example, 1M urea is used to disrupt the nuclear membrane.

Successful DHRS can depend on isolation of the intact nucleus (nuclei), and subsequently enrichment of relative intact and long fragments of closed chromatin and DHRS for amplification. It can be important to avoid disturbing the nuclear structure (e.g., protect the native structure of the nucleus) and to prevent random DNA shearing, particularly when working with low number of cells, for example, single cells. To accomplish this, intact cell(s) can be embedded in a 1.0% InCert (BioWhittaker) low-melt gel agarose. The following steps such as removing protein, DNA purification, DNase I digestion, and MDA can be performed by diffusion into the agarose.

2. Discrimination of Closed Chromatin from Open Chromatin

Next, closed chromatin is discriminated from open chromatin in the genomic DNA by nucleus digestion, or another enzymatic, chemical, and/or physical process.

In some embodiments, the nucleus or nuclei are treated with a DNase. A preferred DNase is DNaseI. Other suitable DNases include, but are not limited to, NMase (DNase micrococcal) and DNase II. DNase I, II and NMase digest DNA of open chromatin regions, but the frequency and specificity of the cutting varies from one enzyme to the next. The concentration of the enzyme can also be varied to customize the cutting. The reaction can be stopped by the addition of EDTA.

Next, the mixture is treated with a denaturing agent, for example, NaOH (pH 14) to denature DNA and proteins, and to remove associated proteins from DNA. Denaturation with NaOH can be neutralized, for example, using TrisHCl, pH7.4.

In some embodiments, the genomic DNA is contacted with a transposon, for example, the Tn5 transposon. Tn5 transposon, which has been used for DHS mapping by ATAC-seq (Buenrostro, et al., *Nature Methods*, 10, 1213-1218, (2013)) by direct in vitro transposition of sequencing adaptors into native chromatin. ATAC-seq can be used to capture open chromatin sites and identify their genomic locations as well as DNA-binding proteins, individual nucleosomes and chromatin compaction at nucleotide resolution. When combined with MDA, Tn5 transposon can be used to identify closed chromatin in accordance with the disclosed methods.

Other chemical and physical treatments, such as sonication of cross-linked chromatin (Auerbach, et al., *PNAS*, 1; 106(35):14926-31 (2009)), can also be used for distinguish closed from open chromatin, and used for closed chromatin mapping when combined with MDA. The sonication plus sequencing (Sono-Seq) has been used to map the open chromatins. The pattern of breakage by Sono-Seq overlaps with, but is distinct from, that observed for FAIRE and DNase I hypersensitive sites. However, none of any of these processes, including DNase I, II, NMase, Tn5 transposon or sonication, has been applied for DHRS or highly closed chromatin regions.

Different enzymatic, chemical, biological, and/or physical methods of disrupting the accessible DNA and thereafter distinguishing open (accessible) and closed chromatin may yield completely or partially overlapping or different chromatin profiles. Although the pattern resulting from DNase digestion may not be exactly the same as the pattern resulting from one of the other methods, the method steps and the output nature are similar: highly closed or compact chromatin is amplified by MDA while open chromatin is not. Therefore, when using non-DNAase based reagents for distinguishing open and closed chromatin (e.g., Tn5 transposon or sonication-based mapping) it may be more appropriate to refer to the closed chromatin regions simply as closed chromatin rather than "DHRS" because the site may or may not be a site hyper-resistant to DNAase. It will therefore be appreciated that "closed chromatin" can be substituted for DHRS in methods that parallel DNase-based methods, but in which a non-DNase reagent or technique is used to shear open chromatin (e.g., into small fragments that are not amplifiable by MDA).

Furthermore, two or more of these can be used in tandem or parallel, and/or in combination with conventional methods of identifying DHS or DHRS sites to customize the chromatin profiles.

B. Selective Amplification of Closed Chromatin-Covered DNA

Next, the large DNA fragments protected by closed chromatin, are selectively amplified and/or physically separated and recovered, for example, by gel size selection, bead-based size selection, or density gradient centrifuge.

Typically, the DNA fragments are amplified by MDA to produce amplicons. MDA-based amplification techniques are discussed in more detail below. This method can be very sensitive and therefore can be used with the starting genomic DNA is very limited.

In a preferred embodiment, MDA is carried out using Phi29 DNA polymerase. In a particularly preferred embodiment, the MDA includes the use of trehalose and other components (which can be pre-mixed) which are added to initiate amplification from about 28° to about 40° C., for example 29° C. or 30° C., for between about 31-16 hours, most preferably about 12 hours (Pan, et al., *PNAS*, 105(40): 15499-504 (2008)). This produces high molecular weight amplified DNA (about 12-kb).

The difference in rates of DNA cleavage at hypersensitive sites and bulk chromatin has been estimated to be one hundred fold. This means that there is an equal likelihood of having one cleavage per 4,000 bases of average chromatin and one cleavage per 40 bases of hypersensitive DNA. Empirical data indicates that the DNase I resistant regions are at least one to two orders of magnitude more resistant to DNase I than open, non-hypersensitive chromatin. Nevertheless some cuts could occur in DNase I resistant regions when excessive DNase I is applied to a relatively small number of cells.

To increase the discrimination of these regions the method can be modified to increase amplification of intermediate size fragments (>1 kb and <4 kb). In a particular embodiment, MDA amplification is followed by a random PCR amplification method as the 2nd round of amplification, so that signals from intermediate size fragments are not be reduced so extensively in the final amplicon. Suitable methods of random PCR amplification are known in the art and described in, for example, Pan, et al; *PNAS*, 110, 594-599 (2013) and U.S. Ser. No. 14/139,612, which is specifically incorporated by reference herein in its entirety. Exemplary methods are also described below.

As illustrated in Example 1 below, it has been discovered that, overall, when a fragment size is > or =4 kb, the amplification efficiency by MDA is maximally independent of the size. However, when the fragment is <3.5 kb, the level of amplification is exponentially correlated to the fragment size. DNase I digested hypersensitive fragments and MSRE generated fragments in unmethylated CpG islands/shores usually are <1 kb, and in the highly opened chromatin, the DNA fragment sizes may be corresponding to single, double or tri-nucleosomes, approximately 100 bp to a few hundreds base pairs. In addition, because the mechanism of amplification requires random primer binding sites upstream of a sequence, there will be a tapering off of the representation of DNA sequences adjacent to the ends of fragments. The precise level of amplification of each fragment may be determined by multiple factors besides fragment size, but no relationship between CG content and amplification efficiency has been found empirically.

When a nucleus (chromatin) is digested with DNase I, the open chromatin associated hypersensitive DNA sites (DHS) derived short DNA fragments will be depleted while the very long fragments/sites protected by compact or closed chromatin, which are usually DNaseI resistant sites (DHRS) will be selectively amplified. The resulting pool of amplicons is then used to prepare a closed chromatin profile. As described in more detail below amplicons can be analyzed and profiles prepared by PCR, microarray analysis, sequencing, etc. When the chromatins are treated with DNase (DNaseI, II, NMase), the detected amplicons are representative of the DHRS sites. When the DNA fragments are generated with methods other than DNase processed chromatin, for example, transponson and sonication, the recovered long DNA pool represents highly closed chromatin, a profile similar to, but not necessarily identical to, DHRS.

DHRS (and closed chromatin) is not typically a simple inverse of DHS (and open chromatin). DHRS are hyper-resistance sites and DHS are the most sensitive sites. There are many sequences that are neither DHS nor DHRS. Therefore, DHRS cannot typically be determined by direct analysis of the DHS regions (e.g., by subtracting DHS regions from the whole genome to identify DHRS). In prepared embodiments, a more complete chromatin profile can include analysis of both DHS and DHRS.

C. Highly Sensitive Selection of Compact and Closed Chromatin

The disclosed methods do not necessarily require physically recovery of short or long DNA, which allows for analysis of DNA isolated from very low number of cells or single cells. However, some methods, particularly those in which the starting DNA is not limiting, can include a physical isolation of the long DNA covered by the highly closed chromatin. In such cases, in addition to or in alternative to MDA, the long DNA fragments can be physically isolated and recovered. The large DNA can be isolated by gel size selection, bead-based size selection, or density gradient centrifuge. This step offers the advantage of isolating different sizes fragments of DNA (such as >10 kb, 10-4 kb, 4-1 kb, 1 kb to 250 bp, 250 to 150 bp, 150 bp to 80 bp etc.,) corresponding to different portions of chromatin, e.g., very highly compact chromatins, highly compact chromatins, compact chromatins, open chromatins, highly open chromatins, chromatins with multiple nucleosomes, chromatins with triple nucleosomes, chromatins with bio-nucleosomes, chromatins with single nucleosomes, and so on.

D. Exemplary Methods

A method of identifying closed chromatins and/or DNase I Hyper-Resistant Sites (DHRS), comprising isolating nucleus (or nuclei) from an intact whole cell or cells to access genomic DNA with compact chromatin structure; fragmenting the genomic DNA associated with certain chromatin conformation or conformations under conditions in which closed chromatins and/or DNase I Hyper-Resistant Sites (DHRS) are represented by fragments that are relatively larger than the fragments that represent open chromatins; selectively recovering the larger fragments; and determining the sequence of the larger fragments and identifying them as closed chromatin and/or DNase I Hyper-Resistant Sites (DHRS). The genomic DNA can be fragmented by contacting it with one or more DNA endonuclease, restriction endonucleases, and other endonucleases. DNA endonucleases include, but are not limited to DNase I, DNase II, NMase (micrococcal nucleases), dsDNA fragmentase, mutant *Vibrio vulnificus* nuclease, and mutant T7 endonuclease. Other endonucleases include, but are not limited to, Mung Bean Nuclease, BAL-31 Nuclease, T7 Nucleases. The genomic DNA can be fragmented by contacting it with a transposon, such as Tn5 transposon or Transposase; physical shearing; sonication; nebulization; acoustic shearing; hydroshearing; cyclical hydrodynamic shearing; by a change in pH (e.g., alkaline or acidic conditions) or temperature (e.g., heating in the presence of a divalent metal cation).

In preferred embodiments, selective amplification of the large fragments is carried out by multiple strand displacement amplification (MDA) to produce amplicons. Suitable polymerases used in the MDA include, but are not limited to, phi29 DNA polymerase, Bst large fragment DNA polymerase (Exo(−), exo(−) Bca DNA polymerase, phage M2 DNA polymerase, phage Bacteriophage PRD1 DNA polymerase, exo(−)VENT® DNA polymerase, Klenow fragment of DNA polymerase I, T5 DNA polymerase, Sequenase, PRD1 DNA polymerase, and T4 DNA polymerase holoenzyme.

The methods typically include sequencing the amplicons and can include mapping the sequences of the amplicons to the genome of the cell or type of cells. Size selection can include gel electrophoresis, gel filtration, and other methods of selective chromatography, and density gradient centrifugation. Some embodiments also include selectively recovering the fragments that represent open chromatins.

III. Methods for Mapping CpG Methylation Status

Compositions and methods of analyzing CpG methylation patterns in genomic DNA of cells are also disclosed. The methods most typically include steps of accessing genomic DNA from one or more cells, digesting the genomic DNA with one or more restriction enzymes, amplifying the DNA to make amplicons, and preparing a methylation status profile by analyzing the amplicons. As discussed in more detail below, the amplification step can be carried out by MDA (e.g., Phi29 amplification), or by PCR. The combination of digestion and amplification allows one to determine if the DMRs are methylated or unmethylated DMRs. Exemplary methods, including additional steps that increase the scope of the data that can be collected and types of subsequent analyses that can be performed are also provided.

In addition to determining methylation and unmethylation patterns/profiles, two methods that allow the profiling of CpG methylation status at single nucleotide resolution are also provided. One method, termed ultra-sensitive MethylC-seq (usMethylC-seq), is an improvement over a current, widely applied genome-wide shotgun bisulfite sequencing (MethylC-seq) method that requires micrograms of gDNA. usMethylC-seq typically includes a very sensitive gDNA purification step, followed by a highly unbiased amplification using semi-random priming with Sequenase and PCR. Another method, referred to as ultra-sensitive RRBS (us-RRBS), is suitable for use with a single cell. The method is based on a PCR step, similar to the step in CpG methylation pattern analysis, which utilizes an adapter designed to minimize sample treatments. The usRRBS method includes an additional step of bisulfide treatment.

It can be important for gDNA to be recovered for CpG methylation analysis using a gentle procedure to avoid non-specific gDNA shearing and to maintain double-strandedness. Therefore, genomic DNA is typically accessed under conditions that retain the double strandness of the DNA, and which also enables a restriction endonuclease (RE) digestion, followed by adapter ligation (except for the usMethylC-seq). An exemplary procedure includes DNA extraction directly from intact cell(s) in the same tube with a lysis buffer, such as guanidine hydrochloride (GndCl)-containing buffer, or a protease (such as the QIAGEN protease, or even Protease K). Empirical results show that guanidine hydrochloride (GndCl) can be used to destroy the DNA-bound proteins and other proteins of a cell, and that with appropriate further dilution, a low concentration of GndCl does not interfere with the complete digestion of the genomic DNA by a high concentration of restriction endonuclease (RE). The guanidine can also be substantially removed by ethanol precipitation by a procedure using a DNA carrier and without phenol-chloroform extraction, which retains the DNA. In addition or alternative, guanidinium thiocyanate (GuTC) or other chaotropes such as urea, thiourea, sufactants or detergent (NP-40TritonX-100, IGEPAL CA-630, CHAPS and Zwittergent) can be used.

Alternatively, DNA can deproteinized by treatment with a heat sensitive protease (e.g., QIAGEN protease) that can be inactivated at temperatures and salt concentrations that do not melt DNA. Under such conditions, no additional physical purification is necessary. This enzyme shows sufficient activity with a low concentration of non-ionic detergents that do not interfere with the downstream enzymatic reactions, and can be efficiently deactivated by moderate heating (70° C. for 15 minutes) without melting DNA.

Proteinase-K, which is hard to deactivate without loss of DNA integrity or double strandedness, is not preferred, but can be used if it is deactivated or removed after the digestion. Data shows that if the DNA is significantly randomly sheared or becomes single stranded, the output sequencing reads may not have satisfactory sequence coverage because short DNA will be lost or depleted, and single strands may not be cut even when the DNA sequence is unmethylated. To further mitigate loss and/or deterioration of DNA, the methods can be carried out using a "single tube procedure" to minimize treatment before amplification and to avoid conventional purification of naked DNA.

Additionally, or alternatively, the assays can be carried out in an agarose gel block (as discussed above for DHRS) to localize the intact cell for treatment. Protease K can be added to in the block to digest the DNA-binding protein and then extracted, before proceeding to amplification (in the agarose). As an additional option, a synthetic RNA carrier such as one used for DNA participation with ethanol (e.g., Terminal Nucleotidyl Transferase synthesized polyA), can be added to the reaction. Most commercially available extracted RNAs contain trace amount of gDNA, which can interfere with or contaminate the result, but synthetic RNAs do not interfere with MSRE digestion or amplification, and reduce, minimize, and/or prevent the chance of DNA loss during DNA extraction.

A. Multiple Displacement Amplification (MDA)-Based Methods

1. MSRE-MDA (MSRE cut-MDA amplification) Method

The MSRE cut-MDA amplification (MSRE-MDA) methods include a step of digesting genomic DNA with one or more MSRE followed by an amplification step using MDA, for example, by using Phi29 polymerase (also referred to herein as MSRE-MDA method). An exemplary method is diagramed in FIG. 11. The MDA-based principles regarding size selective amplification are also utilized in this method. Stretches of fully methylated DNA will be intact (long) and will be amplified efficiently, while the DNA stretches with nucleotides frequently de-methylated will be cut by the one or more of the MSREs.

In some embodiments only a single MSRE is used. In other embodiments, two or more (i.e., multiple) MSREs are used. Exemplary MSRE are provided below. In some embodiments, a mixture of MSREs are used which cut every CpG island (CGI), CGI Shore and other CG rich sequence block more than 2 times, but rarely cut in non-CGI sequences such that the non-CGI as well as the highly methylated CGI sequence blocks are efficiently amplified by MDA. A particular embodiment, most or all of the MSREs are CpG island-specific MSRE, with 5-6 nucleotides (5 to 6-Nt) recognition sites.

Exemplary MSREs and mixtures thereof can include one or more of, but not limited to 6-Nt MSRE: BssHII (GCGCGC (SEQ ID NO:1)), EagI (CGGCCG (SEQ ID NO:2)), FseI (GGCCGGCC (SEQ ID NO:3)), KasI (GGCGCC (SEQ ID NO:22)), NaeI (GCCGGC (SEQ ID NO:4)), Nan (GGCGCC (SEQ ID NO:5)), NgoMIV (GCCGGC (SEQ ID NO:6)), PspOMI (GGGCCC (SEQ ID NO:7)), SacII (CCGCGG (SEQ ID NO:8)), SfoI (GGCGCC (SEQ ID NO:9)), SmaI (CCCGGG (SEQ ID NO:10)), and TspMI (CCCGGG (SEQ ID NO:10)), and 5-Nt MSRE: FauI ((CCCGCNNNN) (SEQ ID NO:12)/(GCGGG) (SEQ ID NO:52)) (4/6). Such MSREs can be referred to as "5 to 6-Nt MSREs". Some MSREs with degenerative nucleotide recognition site may also be used for this method, including, but not limited to HaeII (RGCGCY (SEQ ID NO:13)), BsrFI (RCCGGY (SEQ ID NO:14)), EaeI (YGGCCR (SEQ ID NO:15)), BsiEI (CGRYCG (SEQ ID NO:16)), and Hpy99I (GGWCG (SEQ ID NO:17)).

In a particular embodiment the 4 MSREs, EagI (CGGCCG (SEQ ID NO:2)), NaeI (GCCGGC (SEQ ID NO:4)), BssHII (GCGCGC (SEQ ID NO:1)) and SacII (CCGCGG (SEQ ID NO:8)) are used in combination. In this way, methylated DMRs are left intact and significantly larger (usually >3-4 kb) than non-methylated fragments and will be preferentially amplified during MDA (e.g., Phi29) amplification. This procedure that can discriminate highly methylated CGI sequence blocks (methylated DMRs) and unmethylated CGI sequences of blocks (unmethylated DMRs).

The fragments resulting from amplification can be analyzed using a number of methods, as discussed in more detail below. In preferred embodiments, the fragments are sequenced. The sequence reads can be mapped to the genome. Because, only large DNA fragments (e.g., sequences not frequently cut by the MSRE during the initial digestion step) are amplified during the amplification step, these regions can be identified as methylated DMRs. The DMRs of the genome that are not methylated are cut into small fragments by the MSRE during the initial digestion and are depleted from the amplified fragments that are ultimately sequenced. Therefore, in some embodiments, a region of the genome (e.g., a CpG island) can be determined to be unmethylated when a sequence corresponding to the region is absent from the test assay sequencing reads. As described in more detail below, in some embodiments, only the DMRs or CpG-rich sequences are enriched for library construction and sequencing. This can reduce sequencing efforts.

Figure 11:
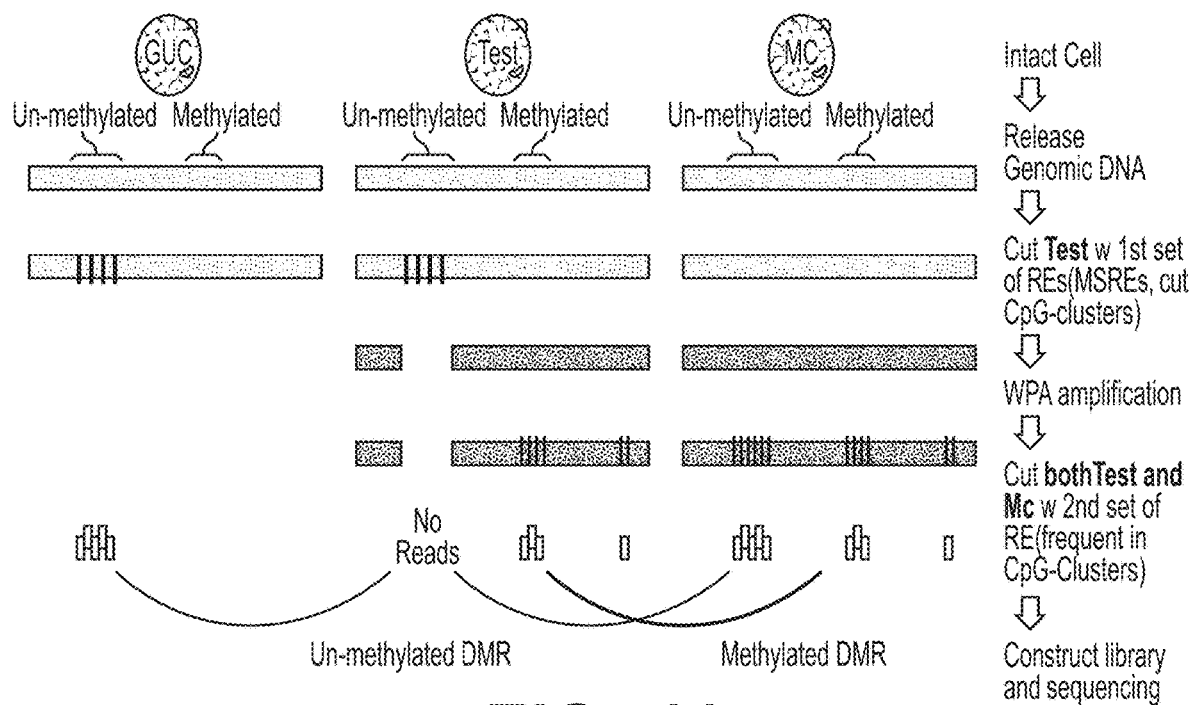
FIG. 11 is a diagram showing an exemplary MDA-based MSRE-MDA method of CpG methylation analysis (MSRE-MDA). The test sample (Test) gDNA is digested with the $1^{st}$ set MSREs (called the 1st set of restriction enzymes or $1^{st}$ RE; for example, a combination of 4 MSREs each with 6-nucleotide (6-Nt) recognizing sites). The methylation control (MC) is not digested with the $1^{st}$ set MSREs. Both test fragments and MC DNA are amplified by MDA. Optionally, the general unmethylation control (GUC), usually composed of a significant number of cells or a relatively greater amount of gDNA, is also digested with MSRE (preferably is a single MSRE with 4-nucleotide (4 nt) recognizing sites (ex. HpaII, BsrUI, Hinp1I, AciI), but it can also the same set of multiple 6-Nt MSREs as the Test). The amplicons in the test and MC assays are then digested in a second restriction digestion with one or more restriction enzymes (e.g, 2nd set of restriction enzymes, or $2^{nd}$ RE), separately each acts on an aliquot of the amplicon, and the fragments may be pooled in combination, to enrich CpG-rich DNA sequences (CpG islands and shores) for library construction and enhance efficient coverage even with reduced sequencing depth. MC is not cut in the 1st restriction digestion and is therefore representative of all potential, candidate DMRs (candidate Differentially Methylated Regions, (cDMRs)). GUC (General Unmethylated Control) is an optional control with bulk DNA from the same type of cells and represents the unmethylated DMRs in the cell population. "Me" refers to methylated DMR (or CpG-rich DNA stretch); "U-Me" refers to unmethylated DMR (or CpG-rich DNA stretch). The MSRE (1st RE) applied to digest the original gDNA is to distinguish Me-DMRs as long and intact fragments, which are amplified efficiently, from Um-DMRs, which are frequently cut into short fragments, and depleted during amplification. After sequencing and comparison to MC, the DMR with significant reads in test are identified as Me (methylated DMR), and the DMR without reads in the tests are identified as U-Me (unmethylated DMR). Generally, most U-Me DMRs should be included in the Un-Me list of the GUC. As discussed above, MDA amplification is correlated to the size of the template DNA fragment (FIG. 1). The short fragments are not efficiently amplified and therefore depleted. When a frequently cutting RE is applied, the whole genomic DNA and particularly the non-CpG islands/shores can be too short to be amplified. Therefore, the $1^{st}$ RE is typically one or more 6-Nt REs that make rare cuts and/or CpG island/shore orientated MSREs.

As shown in FIG. 11, a "test" assay using a MSRE-MDA method is most typically carried out in parallel or combination with one or more control assays which help improve the accuracy of determining if a DMR is methylated or unmethylated. A control referred to in FIG. 11 as a general unmethylated control (GUC) is an assay carried out in parallel with the test assay in which the genomic DNA purified in bulk (typically from a significant starting quantity of cells e.g., a population of cells) is treated with the one or more MSREs. The MSREs can be, for example, a four nucleotide recognizing MSRE such that not only the CGI blocks are enriched in digestion, but also the pieces of cut (unmethylated) DNA sequence are short enough (preferably from about 50 bp to about 500 bp) to be included in a library construction. This library is sequenced directly without phi29 amplification and before library construction or further fragmentation.

GUC is a positive control for candidate unmethylated DMRs (cDMRs). However, it will be appreciated that all cDMRs may not be fully covered if some unmethylated regions are rare in upset of cells of population, and can be missed in a population-based process. Generally, in a population of cells, once there is a sufficient ratio (not necessary to be close to 100%) of DNA for any particular piece of DNA sequence that is unmethylated, a GUC sequence will be detected and identified. Because the fragments in the GUC are not amplified, the small, cut DMRs are not depleted from the pool of fragments that are sequenced. GUC is an optional control.

Therefore, in some embodiments, a region of the genome (e.g., a CpG island) can be determined to be unmethylated when a sequence corresponding to the region is absent from the test assay sequence reads, and is typically present, but not required to be present, in the GUC sequence reads. For example, the region may not be present in the GUC sequence reads when the unmethylated DMR (i.e., the ratio of this type of cells) in the population of cells is very low.

Another control, referred to in FIG. 11 as a methylation control (MC), is an assay in which the genomic DNA is not initially treated with any of the MSRE used for the test assay, but is amplified and sequenced in parallel with the test assay. The MC is a positive control for methylated and unmethylated DMRs, and it is representative of the complete collection of cDMRs that the method can detect in the particular genome. Because the fragments in the MC are not initially cut, small fragments are not deleted during amplification, and amplicons of both methylated or unmethylated DMRs are represented in the pool of fragments that are sequenced.

Therefore, in some embodiments, a region of the genome (e.g., a DMR) can be determined to be unmethylated when a sequence corresponding to the region is absent from the test assay sequence reads and present in the MC sequence reads. In preferred embodiment, the reads are also present in sequence reads in the GUC control. A region of the genome can be determined to be methylated when a sequence corresponding to the region is present in the test assay sequence reads and present in the MC sequence reads. In preferred embodiments, the reads are also absent in sequence reads in the GUC control.

As shown in FIG. 11, optionally, but preferably, both the test fragments and MC fragments are treated with a second digestion using of one or more restrictions enzymes, sonication, or another method of DNA fragmentation after amplification and prior to library construction and sequencing (e.g., as discussed above the MSRE-MDA method). Preferably restrictions enzyme(s) used in the second restriction digestion cuts DNA in DMRs. An exemplary enzyme is BstUI (CGCG). This enriches the DMR (e.g., CpG islands and other CpG-rich DNA stretches or CpG shores) sequences and improves efficient coverage even with reduced sequencing depth. Furthermore, the enzyme can be selected such that the digestion product gives a blunt, phosphorylated end, which affords an additional advantage that an end-blunting step (that could bring in non-specifically sheared short fragments) can be omitted during the preparation of a sequencing library.

For example, as illustrated in FIG. 11, a $2^{nd}$ restriction endonuclease (RE) digestion is applied. This $2^{nd}$ RE can recognize CG rich sequence tags. Suitable enzymes include, but are not limited to, HpaII, BstUI, AciI, and HinP1I etc. The REs are typically MSRE although the methylation-sensitive properties are not utilized, and non-MSRE (such as MspI) are also useful as long as they enrich MDR or CpG-rich sequences. Instead, the MSRE is selected primarily because it cuts frequently in CGI sequences, thus enriching the CGI sequence in sequencing library. This technique can minimize sequencing cost, while retaining the CGI methylation detection power (coverage). When the $2^{nd}$ RE is applied for CGI enrichment, two or more REs (HpaII, BstUI, AciI, and HinP1I, etc) may be applied separately, and in combination to improve the coverage of CGI.

Additionally, or alternatively other methods can be employed to enhance CGI detection with minimal sequencing. For example, in some embodiments, CpG rich sequence binding protein-based beads can also be utilized. In a particular embodiment for improving CGI enrichment, the amplicon is sheared randomly by some physical or chemical methods. The sheared amplicon (e.g., short fragments) are captured with a commercial DNA binding protein (Methyl-Collector™ Ultra, MBD, or Un-methyCollector), which binds to DNA fragments with more methylated CpG sites (the amplicon should be artificially methylated with CpG methyltransferase, when MethylCollector™ Ultra or MBD kit is applied), or unmethylated CpG sites (it can be directly applied to the amplicon without methylation) with high affinity. By optimizing the washing condition, one can efficiently and specifically enrich the desired CpG-rich fragments. It will be appreciated that this and other methods of CpG enrichment can also be used as an optional step in other methods disclosed herein.

As illustrated in FIG. 11, in particularly preferred embodiments, a DMR is determined to be methylated when a sequence corresponding to the region is present in the test assay sequence reads and present in the MC sequence reads after two rounds of restriction digestions, library construction and sequencing, as discussed above. The methylated DMR are most often present in the sequencing reads from the GUC. In the most preferred embodiments, a DMR is determined to be unmethylated when a sequence corresponding to the region is absent from the test assay sequence reads and present in the MC sequence reads, preferably after two restriction digestions, library construction and sequencing, as discussed above. The unmethylated DMR are most often present in the sequencing reads of the GUC.

2. ML-MDA (MSRE Digestion-Ligation-MDA-Amplification) Method

It will be appreciated that in some embodiments of the MSRE-MDA method discussed above, non-recovered DMRs may be unmethylated regions or alternatively, are fragments that were randomly lost during the assay, not due to MDA-based short-fragment-depletion, but rather, for example, due to using too little input, etc. When the cut DNA is directly amplified as in the MSRE-MDA method, the amplicons do not contain sequences crossing MSRE sites that were originally unmethylated and thus enzyme sensitive. The DNA is cut off at the unmethylated sites, which tends to generate short DNA fragments that will be depleted during amplification, and is also relatively depleted for sequences adjacent to the MSRE cutting sites because MDA amplification tends to eliminate the fragment terminals (FIGS. 1A-1D). Accordingly, there may be confusion between MSRE sites that were cut and sequences that were randomly lost due to an artifact of the assay. Therefore, in some embodiments, some DMRs determined to be unmethylated by their absence from sequencing reads in the test assay may not actually be unmethylated regions, but due to random loss.

It has been empirically determined that when the starting material is at least 100-cells, most non-covered sequence reads from a test assay compared to MC sequence reads correspond to unmethylated regions. 10-cells processing and sequencing showed a similar result. However, increasing the amount of starting material can reduce the rate of false positive identification of unmethylated regions using the MSRE-MDA method.

A related method, referred to herein as ML-MDA (MSRE-Ligation-MDA), is also disclosed that further reduces the chance of falsely categorizing a region as unmethylated. The ML-MDA method recovers sequences for both methylated and unmethylated regions, and therefore does not require absence/subtractive analysis as in the MDA-based MSRE-MDA method described above. An exemplary method is diagrammed in FIG. 13.

The ML-MDA method includes a step of cutting genomic DNA with one or more methylation sensitive restriction endonuclease (MSRE). A different MSRE(s) may be applied compared to those discussed above for the MSRE-MDA method, because for ML-MDA, a more frequent cut on CGI is desired such that the methylation status of CGI sequences will have a greater chance of being detected with suitable coverage. The 4 nucleotide-recognizing (4-Nt) MSREs, such as HpaII, BstUI, AciI, and HinP1I are preferred REs, usually applied as single enzymes. In other embodiments, 1 or more of the 5 to 6-Nt MSREs are used. For 5-Nt MSRE, 1 MSRE may be enough. Examples include, but are not limited to, HaeII or RsuRI (RGCGCY, R=A or G, Y=T or C). In some embodiments, including 6-Nt enzymes, MSRE are combined together which give the same cohesive ends that allow an efficient ligation after digestion. An example with 6-Nt enzymes is the combination of NgoMIV ((GCCGGC) (SEQ ID NO:6)) and TspM1 ((CCCGGG) (SEQ ID NO:10)). More exemplary enzymes include, but not limited, to the BssHII, NaeI, SacII, NarI, EagI, FauI, FseI, KasI, NgoMIV, PspOMI, SfoI, SmaI, and TspMI and can also be used alone or in combinations of two or more. With 5 to 6-Nt MSREs, the cut site will not be too frequent, such that fragments will be long enough to allow efficient circularization. This can be better for downstream MDA amplification and overall improves the CGI and/or DMR coverage. Short dsDNA fragments (e.g., <125 bp), even with cohesive end, are not efficiently internally circularized. In some embodiments, 4 or more of this type of MSREs are used in combination to give sufficient potential fragments for each CpG islands or DMRs, so as to get thorough coverage.

The mismatching ends generated by different MSREs are not a problem because an internal circularization between two ends of the same MSRE cut of a fragment is preferred. To simplify the process, a compatible reaction buffer and choosing MSREs with diversified recognizing sites are preferred.

In addition or alternatively, some MSREs with degenerative nucleotide recognition site may also be used for this method, including but not limited to HaeII (RGCGCY (SEQ ID NO:13)), BsrFI (RCCGGY (SEQ ID NO:14)), EaeI (YGGCCR (SEQ ID NO:15)), BsiEI (CGRYCG (SEQ ID NO:16)), and Hpy99I (GGWCG (SEQ ID NO:17)).

Next, the fragments are subjected to a ligation reaction. The ligation reaction is preferably carried out under conditions that drive internal circularization of the fragment. Because the circularization is an intramolecular reaction, its efficiency is typically independent of the concentration of DNA molecules unless the concentration of DNA becomes much higher than would be the case for single cells. This favors low number of cells, especially single cell analysis.

Figure 13:
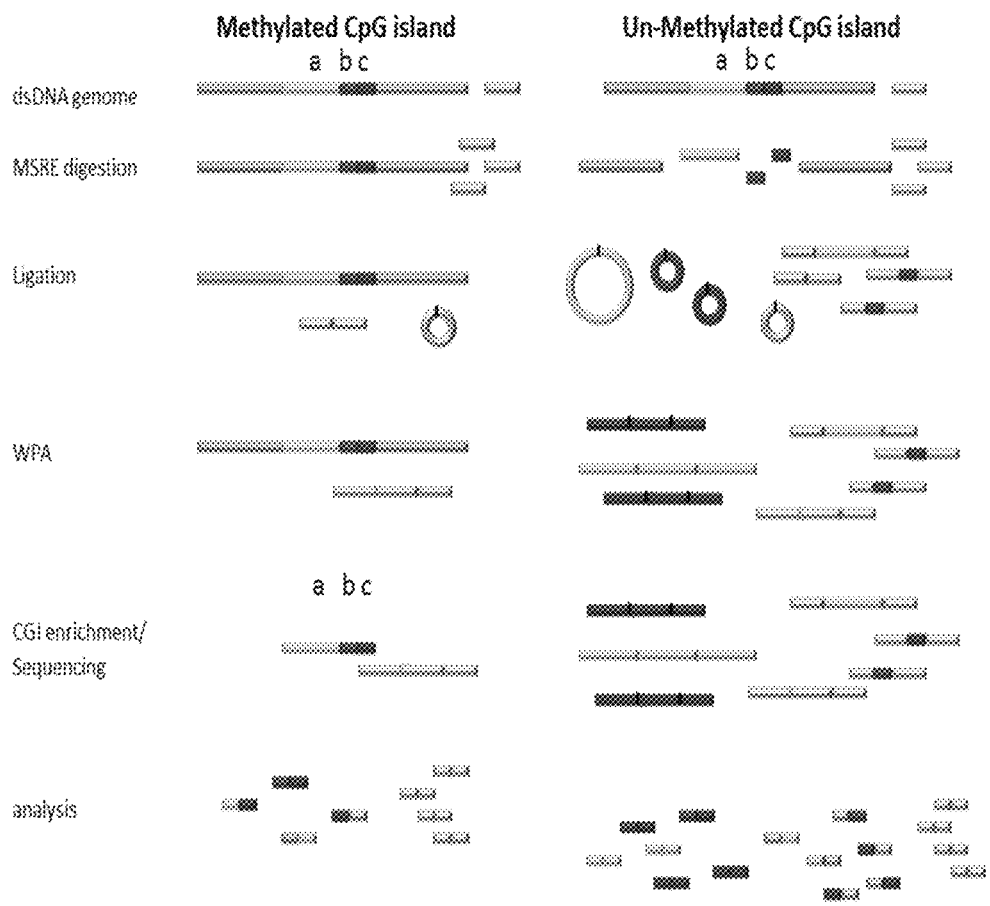
FIG. 13 is a diagram showing an alternative strategy for MDA-based CpG methylation pattern profiling referred to as MSRE-ligation-MDA (ML-MDA). ML-MDA potentially reduce, minimize, and/or prevent any possible false identification of un-methylated regions that may exist in MSRE-MDA based CpG methylation analysis methods, and can be used to directly detect both CpG methylated and unmethylated regions, and to create a genomic mutation profile. For CpG methylation profiling, methylated sites are retained in the amplicon in the original sequence order of the genomic DNA (left panel). The unmethylated sites are cut during MSRE digestion, and the cut sites are re-ligated, and in some cases re-organized, from originally non-continuous sequences. Most of ligation is internal circularization, but some fragments may be ligated to DNA fragment from elsewhere of the genome (right panel). Subsequent sequencing and bioinformatics analysis can be used to elucidate if the sites are cut or not cut, i.e. the original sequences are unmethylated or methylated.

With MSRE digestion, methylated sites are not cut. Therefore, the methylated regions retain their original sequence order from gDNA with no intervening sequences (FIG. 13, left panel). With MSRE digestion, unmethylated sites are cut. Cut, unmethylated sites can be re-ligated to incorporate intervening fragments that were not originally sequential with respect to the MSRE sites. Some of the unmethylated fragments will incorporate DNA fragment(s) from elsewhere in the genome to form linear or circular fragments with sequences that were originally non-continuous in the genome (FIG. 13, right panel).

Subsequently, the cut and ligated fragments are amplified by MDA to produce amplicons. In preferred embodiments, the amplicons are sequenced. With sequencing reads, bioinformatics can elucidate if sites are cut or not cut, i.e. the original sequences are unmethylated or methylated. If the amplicons contain both original sequences flanking the specific MSRE site (when aligning to the genome sequence embedding this site), the recovery of such continuous genomic sequences will indicate that the MSRE site is methylated in the original gDNA. Conversely, if a MSRE site was unmethylated and cut, ligation would then generate a circle joining the two ends of an original fragment together and form a new MSRE site. After amplification, this circle will result in a long fragment containing concatamers of the original circle. The sequences of both sides of each MSRE site will be derived from non-contiguous regions of genomic DNA, i.e. the two ends of a DNA fragment flanked by unmethylated MSRE sites (FIG. 13).

Similar to the MSRE-MDA method discussed above, these methods can include a CGI-orientated RE digestion for the enrichment of the CGI sequences for library construction and sequencing. However, in preferred embodiments, in contrast to a preferred option in the MSRE-MDA, the $1^{st}$ RE used for as the $1^{st}$ MSRE digestion in these methods will not be the same as applied again for the $2^{nd}$ RE such that the $1^{st}$ cut site will be flanked with the $2^{nd}$ RE sites.

Additionally or alternatively, as discussed above with respect to MSRE-MDA, CpG site number-dependent DNA sequence enrichment can be accomplished using DNA binding protein beads (ex. MethylCollector™ Ultra, MBD beads, or Un-methyCollector, etc., as discussed above). Enriching CpG rich fragments can reduce the number of sequencing runs needed to generate sufficient coverage, thereby reducing the expense of the assay.

An potential advantage of ML-MDA based methods over MSRE-MDA based methods is that the ML-MDA based methods allows one to detect both CpG methylation pattern and DNA sequencing mutation for the same sample, in a genome-wide or exome-only sequencing (e.g., WGS or WES) fashion. By adding this optional step, one can simultaneously analyze any possible mutation with the same sample that is analyzed for CpG methylation pattern. This is can very useful, particularly, when analyzing a single cell. For example, knowing the mutation can provide information about the cause of a potential differential methylation pattern between two different sources of cells, and even be correlated to activities of the cells. An example of sequencing data is displayed on IGB (integrate genome browser), as shown on FIG. 16.

For embodiments that include mutational analysis at single nucleotide resolution, the amplicons is typically divided into 2 aliquots: one for CpGmp and the other one for mutation profiling (e.g., WES). In some embodiments, the MSRE is HpaII. If the mutation occurs in the HapII site (CCGG), the site will not be cut with HpaII even if the C nucleotide in the CpG is not mutated and unmethylated. This can be easily identified by inspection of the sequencing reads. In some embodiments, 2 or more of the 5 to 6 Nt MSREs are utilized. IN a preferred embodiment, 4 or more of MSREs are used selected from the group consisting of AscI, BssHII, NaeI, SacII, NaeI, AscI, EagI, FauI, FseI, KasI, NgoMIV, PspOMI, SfoI, SmaI, and TspMI.

B. PCR Amplification Based Methods

PCR-based methods of determining CpG methylation status are also provided. Two embodiments, one each for directly identifying methylated DMRs (Me-CpG) and unmethylated DMRs (Um-CpG) are outlined below. It will be appreciated that these embodiments can be performed alone or together, and/or including variations to customize the profile or analysis that is desired. Also provided below are methods of coupling the embodiments and variations thereof, to genomic analysis including reduced representative bisulfite sequencing and genome bisulfite sequencing which can be used to determine "C" (beyond CpG) methylation status at single nucleotide resolution.

Two PCR-based variations are based on similar principles. The methods utilize oligonucleotides suitable for initial and direct (without further modification on the DNA fragment) ligation of the cut DNA after a restriction enzyme digesting and enriching the CpG rich sequences.

1. FAM-PCR

Fragmentation-Adapter ligation-MSRE digestion-PCR (FAM-PCR for Me-Seq) based methods for identifying methylated and unmethylated DMRs (Me-DMRs and Um-DMRs, or Me-CpG and Um-CpG) and for us-RRBS (Ultrasensitive RRBS) are provided.

Methods of recovering and amplifying methylated DMRs (Me-CpG) can include recovering genomic DNA under mild conditions which prevent or limit non-specific shearing of the genomic DNA and maintain its double-strandedness. Such methods are discussed in more detail above for DHRS analysis, and can also be used to access gDNA for FAM-PCR based methods.

After accessing genomic DNA, the gDNA is digested with one or more non-MSRE. In preferred embodiments the restriction enzyme cuts in CG-rich regions. An exemplary restriction enzyme is MspI. Alternative REs (i.e. non-MSRE) include BsaWI ((WCCGGW) (SEQ ID NO:11)), and Taq-alpha-I (TCGA), After the restriction digestion, the fragments are ligated with adaptors that provide binding sites for PCR primers. Preferably, the adapters are designed to enable efficient ligation without pre-modification of the cut DNA, and without significant adapter-dimer. Preferably, the ligation is managed to occur between adapter and the fragments such that RE digested fragments are flanked with the adapter, with little or no fragment-to-fragment ligation and little or no fragment internal circularization. In particular embodiments in which downstream analysis includes bisulfite sequencing (usRRBS), all Cs in the adaptor can be methylatedcytosine, which are stable (inconvertible) during bisulfate treatment.

The original adapter contains a longer, full length oligonucleotide hybridized to which a shorter (less than full length) oligonucleotide at the 3' end of the longer oligonucleotide. The full-length oligonucleotide is covalently ligated to the 5' ends of the genomic DNA fragments, while the short oligonucleotide is melted off after the ligation reaction. DNA polymerase is used to fill in the stand complementary to the longer oligonucleotide by extending the 3' end of the DNA fragment in an extension reaction using the full length oligonucleotide as the template. The adapter ligation typically involves only one of two strands of the adapter being ligated between the adapter and an end of the cut DNA fragment. More specifically, the 3' terminal nucleotide of the longer oligonucleotide of the adaptor is covalently ligated to the 5' terminal nucleotide, which has 5' phosphate group, of the RE digested DNA fragment. The shorter oligonucleotide can vary in length, but is typically short enough such that it will melt off before filling-in step, and sufficiently long such that the doublestranded end of the adaptor can form a relative stable cohesive end for the ligation as described above, under the designed ligation condition (FIGS. 16B and 25C). Preferably, no covalent ligation occurs between adapters (no adapter dimer is ligated with covalent bond). This can be reduced, minimized, or prevented by designing the adaptor such that the 5' terminal nucleotide does not have a 5' phosphate.

The ligation step is a single-strand-covalent-ligation between the adapter and the cut DNA fragment. After ligation the shorter oligonucleotide of the adaptor is heat denatured from the fragment at a temperature (e.g., > or =37° C. but <75° C.) such that the short oligonucleotide is melted off but the double stranded DNA fragment itself remains double stranded. The single stranded portion of the adaptor can be filled-in in an extension reaction (5' to 3' end toward outside of the construct, beginning with the terminal 3' OH of the DNA fragment) using, for example, the conventional 4 nucleotides (e.g., using dCTP, dATP, dGTP and dTTP). The extension reaction can be carried out using any suitable DNA polymerase without strand displacement activity, without 5'-3', and without 3'-5' DNA exonuclease, such as sulfolobus DNA polymerase IV, and also some other enzymes such as Klenow fragment (5'-3' exo−), or any Taq DNA polymerase without 5'-3' exonuclease. The extension reaction can be carried out, for example, before (e.g., immediately before) the denaturation step (>90° C.) of the $1^{st}$ PCR thermal cycle. The reaction generates a DNA fragment including full length double stranded adapters. In a particular embodiment, the extension is carried out with a DNA polymerase with 5'-3' exo- and 5'-3' exo-polymerase when the long/full length adapter oligonucleotide is not blocked at its 5' end, or alternatively with any Taq DNA polymerase when the long/full length adapter oligonucleotide is 5' end blocked from digestion.

In particular embodiments in which downstream analysis includes buisulfite sequencing (usRRBS), a 5-methyldeoxycytidine triphosphate can be used in place of conventional dCTP, and in combination with the other three dNTPs (dGTP, dATP and dGTP) to generate fragments that include double-stranded adapter sequences in which all four strands of the adapter (two double stranded adaptors, one at each end of the original DNA fragment), all include methylated "C's", which are not convertible and ready for bisulfite treatment. In contrast, for non-bisulfite application, all 4 conventional (non-methylated) dNTPs can be applied for the filling.

Next, fragments are treated with one or more MSREs and subsequently subjected to PCR using PCR primers that hybridize to binding sites engineered into the adaptors. Exemplary MSREs include, but are not limited to, AciI (CCGC or GCGG), Hinp1I (GCGC), and BstUI (CGCG). During the digestion step, methylated regions are protected and remain uncut/intact, while unmethylated regions are cut. The methylated fragments are amplifiable by PCR because the adaptors, and therefore primer binding sites within the adaptors, will remain on both ends of the fragment. In contrast, the unmethylated fragments will be cut into two or more fragments, and therefore will have only one or zero adaptors. Accordingly, the unmethylated fragments will not be amplified exponentially, and/or will be depleted relative to the methylated fragments during PCR.

For methods including usRRBS, after the adaptor ligation and filling-in, the fragments are treated with bisulfite treatment. Kits are commercially available, see, for example, Qiagen and Zymo. The kit based procedures are typically modified to accommodate the disclosed methods which can include direct processing of intact cells and without purifying DNA before bisulfite process. For example, an effective amount of short-oligonucleotide carrier (e.g., <50 mer) having a sequence that does not hybridize to or otherwise interfere with the adapter and primers can be added to the DNA before the bisulfite process.

In preferred embodiments, the adaptors are designed so that they can be completely removed from amplicons after PCR, for example, by including a restriction site which can be cleaved during a restriction digestion with the appropriate restriction enzyme. As discussed in more detail below, Amplicons can be subjected to sequencing, for example next-generation sequencing. Removal of the original adaptor sequence can prime the amplified fragments for attachment of sequencing adaptors in a subsequent step. In a particular embodiment, the restriction site is a site that can be cut by a restriction endonuclease (RE) so that the adapter can be completely removed. For example, the sequence of the adaptor can include a Type IIS endonuclease sequence (such as, but not limited to, BciVI), which after digestion will remove the original adapter sequence but leave a dATP at the 3' end of the DNA insert for directly ligating to NGS sequencing adapters. If the downstream analysis is to be sequenced in a platform other than Illumina HiSeq, such as Proton, the corresponding amplicon ends can be designed accordingly. If the downstream analysis is not by NGS sequencing, for example, by microarray or PCR, this adapter-switch step is not needed.

In preferred embodiments, the amplicons are sequenced. The sequenced fragments (DMRs) are determined to be methylated, and can be mapped to the genome by bioinformatics techniques. Unmethylated fragments (DMRs) are generally not amplified, and therefore will generally not be sequenced.

A collection of candidate DMRs (cDMRs) can be built separately with the same genome but from a different starting DNA sample (usually with a population of cells) or a sample that is divided into two aliquots before the second RE digestion. The control sample are typically subjected the method above but wherein the $2^{nd}$ MSRE digestion step is excluded. Therefore, all fragments, methylated and unmethylated, will be amplified. Using this collection, the unmethylated fragments can also be deduced by subtracting methylated DMRs from the complete collection of cDMRs.

2. MA-PCR

MSRE digestion-Adapter ligation-PCR (MA-PCR) based methods for identifying unmethylated DMRs and methylated DMRs are also provided. Methods of recovering and amplifying unmethylated DMRs (UnMe-DMRs) are similar to the methods discussed above with respect to Me-DMR, but with some alterations discussed in more detail below. The Me-DMR based methods include a $2^{nd}$ MSRE cut to discriminate methylated DMR from un-methylated DMR. Methods that do not require a second cut can be even more robust.

In MA-PCR based methods, the Me-DMRs and Um-DMRs are distinguished at the $1^{st}$ step, and therefore only one step is necessary to detect the CpG methylation patterns. The MA-PCR methods directly detect Um-DMRs, while the FAM-PCR directly detects Me-DMRs. The Me-DMRs in MA-PCR procedure and the Um-DMRs in FAM-PCR are determined by subtracting the detected sequencing reads from a control that includes a collection of all cDMRs for the give genome for a population or type of cells. As discussed above, preferably, the control collection of cDMRs are obtained by processing a relative large number of cells, which can be more robust than procedures in which only a single cell is used.

As above, the methods (MA-PCR) for recovering and amplifying UnMe-CpG typically include recovering genomic DNA under mild conditions, which prevent or limit non-specific shearing of the genomic DNA and maintain its double-strandedness.

Next, the genomic DNA is digested with one or more MSREs. The MSER can be 4-Nt MSER. Exemplary 4-Nt MSER include, but are not limited to, Hinp1I, HpaII, BstUI, and AciI. Usually one of the 4-Nt MSRE is sufficient. Such MSRE have the potential (when there is no CpG methylation) to cut quite frequently at candidate DMR sites or CpG-rich sequences. Similar to the description for ML-MDA method, 1 or more of the 5 to 6-Nt MSREs can also be used. Exemplary MSREs include, but are not limited to, BssHII, NaeI, SacII, NarI, EagI, FauI, FseI, KasI, NgoMIV, PspOMI, SfoI, SmaI, and TspMI, each of which can be used alone or in combinations of 2 or more. For both types of MSRE (4-Nt, and 5 to 6-Nt), the chosen MSRE is preferably very specific, with little or no non-specific digestion even with an extremely high ratio of the enzyme-to-DNA or under a non-optimal condition. Hinp1I is a preferred 4-Nt MSRE.

With multiple 5-to-6-Nt MSREs in combination, the cut site will not occur too frequently, such that there will be long enough fragments (preferably 100 bp-500 bp) to allow an efficient PCR amplification, but frequent enough such that most DMRs or CpG-rich sequences are covered with at least 2 cutting sites. One consideration is that when 1 or multiple 5 to 6-Nt MSREs are applied, it is preferably to choose the MSREs with the same cohesive ends (compatible cohesive ends), such that immediately after MSRE digestion, without any end-repair or additional of any nucleotide, a ligation to a universal adapter with the end compatible to the cohesive ends can be applied directly. Alternatively, a mixture of variant cohesive ends for the adapter is designed to match a combination of multiple 5 to 6-Nt MSREs with different cohesive ends. For 5-Nt MSRE such as FauI ((CCCGCNNNN) (SEQ ID NO:12)/(NNNNNNGCGGG) (SEQ ID NO:52) (4/6)), one enzyme could be enough, and the mixture of variant cohesive ends for the adapter is preferred.

During this digestion, only the Um-DMRs are digested. After the restriction digestion, the Um-DMR fragments are ligated with adaptors that provide binding sites for PCR primers as discussed above for the Me-CpG methods. After ligation, the fragments are subjected to polymerase chain reaction using primers that bind to the adaptors. Unmethylated regions will be selectively amplified, and Me-DMR will be depleted. The Me-DMR are resistant to the digestion of the MSRE and remain embedded within much larger fragments of DNA. No ligation occurs around the Me-DMR, therefore no amplification occurs around Me-DMR regions.

In preferred embodiments, the amplicons can be sequenced. The sequenced amplicons are determined to be unmethylated, and can be mapped to the genome by bioinformatics techniques. Methylated fragments are not generally amplified, and therefore will not generally be sequenced, but can be mapped by subtractive analysis.

Control cDMRs are prepared and identified as discussed above for the FAM-PCR based methods. In MA-PCR, the Me-DMR regions can be determined by subtracting the Um-DMRs from the all cDMRs.

C. Bisulfite Sequencing

Bisulfite sequencing methods can be performed alternatively, or incorporated into the PCR-based methods discussed above. Accordingly, the bisulfite-based methods can include one or more of the steps discussed above. The bisulfite analysis can be adapted to be carried out in a single tube. In particular, two improved methods of bisulfite sequencing, referred to as usRRBA and usmethylC-seq as disclosed. Both methods are very sensitive and suitable for use with gDNA accessed or isolated from low quantities of cells or even a single cell. The improved methods enable significant coverage of CpG sites in CGI, and a faithful message, e.g., close to complete bisulfite conversion rate, and minimal nucleotide error.

The methods are linked by conditions in which the DNA is accessed or isolated and handled prior to bisulfite sequencing. DNA purification is achieved under mild condition while maintaining double strandedness of the DNA. To reduce loss of material, there is a minimum of DNA processing before the DNA is subjected to a modified PCR amplification procedure.

Bisulfite sequencing involves the use of bisulfite treatment of DNA to determine its pattern of methylation. In animals, DNA methylation predominantly involves the addition of a methyl group to the carbon-5 position of cytosine residues of the dinucleotide CpG. Treatment of DNA with bisulfite converts cytosine residues to uracil, but leaves 5-methylcytosine residues unaffected. Thus, bisulfite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information.

In some conventional protocols, DNA is isolated and extracted prior to bisulfite conversion. DNA is sensitive to damage and can be lost during DNA extraction leading to incomplete coverage, particularly when the starting genomic DNA material is limited as when it is from a single or low quantity of cells. Therefore, in some of the embodiments disclosed herein, the DNA is treated gently prior to bisulfite conversion. Suitable methods of gently accessing and isolating gDNA are discussed above. For example, any of the bisulfite methods can include DNA extraction directly from intact cell(s) in the same tube with a lysis buffer, such as GndCl and GuTC plus precipitation with DNA carrier, which enable a sufficient protein removal and dsDNA release. Some embodiments include use of QIAGEN protease but not Proteinase-K, as discussed above, which can be deactivated without phenol-chloroform extraction for the DNA by using medium temperature heating.

The DNA subjected to the disclosed bisulfite sequencing methods are also modified by the addition of adaptors including primer binding sites (discussed in more detail above) to facilitate PCR amplification of the DNA. The adapter are designed to enable a direct ligation without a pre-DNA blunting or A-addition, which minimizes the DNA treatments and DNA damage and improves the coverage of the CpG sites and CGI.

Very few DNA polymerases can generate a conventional DNA from the bisulfate product because U is not a usual template for DNA polymerases. It has been empirically determined, that Sequenase, such as the Sequenase Version 2.0 DNA polymerase, can synthesize a new DNA strand with a template DNA strand containing U (pairing U with A) as well as conventional G, A, T and C. Sequenase can faithfully and efficiently synthesize a normal DNA strand (G, A, T, C) based on a bisulfite treated DNA template containing U, particularly when 2 or more cycles, preferably at least 4 cycles, of denaturing/reannealing→adding new enzyme→DNA synthesis are carried out. Sequenase synthesis can be carried out using a semi-random primer as described above and described in the SMA method in the paper Pan, et al., *PNAS,* 110:594-599 (2013) and U.S. Published Application No. 2014/0213485 which is specifically incorporated by reference herein in its entirety.

In some embodiments the bisulfite conversion is usRRBS and is incorporated into one of the PCR-based CpG methylation analysis techniques described above, e.g., the ML-PCR-based method. usRRBS is first described above. In usRRBS the reduced represented sequences are covered with a relative low sequencing cost. However, because a large fraction of DNA methylations of regulatory significance tend to occur in clusters along DNA, so that sampling of a fraction of CpG sites across the genome offers an overview of changes in methylation pattern that can be obtained with methods that are less complex than bisulfite sequencing but provide data about CpG island methylation. This method is adaptable to high throughput sequencing and informatics analysis to measure methylation patterns for single cells as well as for bulk cells. The method can simultaneously provide DNA for mutation analysis and measure methylation status of CpG islands from the same single cell.

In a particular embodiment for coverage of CGI sequences and their related sequences, the conversion is typically carried out after non-MSRE digestion (such as MspI), adapter ligation and filling-in. The adapter oligonucleotide is one in which C's are methylated so the sequence remains un-converted during bisulfite conversion. The PCR procedure utilizes a DNA polymerase that couples uracil (such as the Pfu Turbo Cx hotstart DNA polymerase from Agilent, or EpiTaq HS from Clontech/TakaRa) and a primer that hybridizes to the 3' end the adapter to amplify the bisulfite converted product. This improvements and modifications to RRBS enhances CpG sites coverage compared to known methods such as those described in Guo, et al., *Genome Res.,* 23(12):2126-35 (2013), Epub 2013 Oct. 31.

In some embodiments, a genome wide profile of the bisulfite converted status of the sequences is desired. Such methods can be referred to usMethylC-seq. The methods utilize Sequenase v2 from Affymetrix and employ a protocol similar to the SMA methods described above. The method is effective for comprehensive coverage of the whole genome sequence and faithfully reflects the original methylated and unmethylated cytosines in the tested DNA.

In some embodiments for the PCR-based methods for CpG methylation profiling above, particularly the FAM-PCR, MA-PCR and usRRBS, a multiplex adapter is used to label different original samples, such as individual single cells, at a very early stage, before PCR amplification. In particular embodiments the sequences of this multiplex adapter, except the barcode tag that is usually designed at the end that is directly ligated to the sample fragment, is replaced with the library adapter that fit a NGS sequencing platform.

D. Exemplary Methods

A method of identifying candidate Differentially Methylated Regions (cDMRs) for a genome can include, for example, isolating nucleus (or nuclei) from an intact whole cell or cells to access genomic DNA under conditions that maintain double strandedness and reduces, minimizes, and/or prevents random shearing of the genomic DNA; amplifying the DNA by MDA to produce amplicons; optionally, but preferably, enriching CpG rich sequences of the amplicons comprising CpG islands, CpG shares and other CpG rich sequences; and determining the sequences of the amplicons, wherein the sequence are identified as cDMRs.

A method of identifying a methylated DMR can include, for example, isolating nucleus (or nuclei) from an intact whole cell or cells to access genomic DNA under conditions that maintain double strandedness and reduces, minimizes, and/or prevents random shearing of the genomic DNA; digesting genomic DNA with one or more methylation sensitive restriction endonucleases (MSREs); amplifying the digested DNA by MDA to produce amplicons; and determining the sequences of the amplicons, wherein the sequences of the amplicons are identified as methylated DMRs.

In some embodiments, the MSREs is one or more 4 to 6-nucleotide (4-6 Nt) recognizing CpG island-specific MSREs, preferably 2 or more 6-Nt recognition site MSREs, or a combinations thereof, wherein each unmethylated CpG island or other CpG-rich sequence block of the genomic DNA is cut about 2 or more times with at least one cut fragment being <3 kb, and wherein the cutting of non-CpG-rich sequences only cuts fragments of genomic DNA into fragments of greater than about 4 kb.

The method can include mapping the methylated DMRs to the sequence of the genomic DNA.

In some embodiments, a method of identifying unmethylated DMRs includes, identifying methylated DMRs for example, as discussed above; mapping the methylated DMRs to the sequence of the genomic DNA; identifying DMRs as unmethylated DMRs by subtracting the methylated DMRs from a collection of cDMRs.

In some embodiments, a method of determining if a differentially methylated region (DMR) is methylated or unmethylated includes, isolating nucleus (or nuclei) from an intact whole cell or cells to access genomic DNA under conditions that maintain double strandedness and reduces, minimizes, and/or prevents random shearing of the genomic DNA; digesting genomic DNA with one or more methylation sensitive restriction endonucleases (MSRE); ligating the fragments of genomic DNA under conditions that drive intramolecular circularization; amplifying the fragments of genomic DNA by MDA to produce amplicons; and determining the sequences of the amplicons, wherein the sequences of amplicons that are deduced to be representations of contiguous linear assembly genomic DNA sequences at the MSRE recognizing sites are identified as methylated DMRs; and wherein the sequences of amplicons that are deduced to be representations of non-contiguous non-linear assembly genomic DNA sequences at the MSRE recognizing sites are identified as unmethylated DMRs. The methods can include mapping the methylated DMRs and/or the unmethylated DMRs to the sequence of the genomic DNA.

In some embodiments, the ligating is carried out by double strand DNA ligase such as variants of T4 DNA ligases, or wherein the digested double DNA fragments are converted to be single strands and the ligating is carried out with a single strand DNA ligase such as Circligase (such as CircLigase-ssDBNA ligase or Circligase II-ssDNA ligase from Epicentre).

The MSRE can be chosen such that the unmethylated CpG islands or other CpG-rich sequence blocks (cDMRs) are cut into fragments on average between about 150 bp and 1 kb, preferably using one 4-Nt MSREs, or one or two 5-Nt, or two or more 6-Nt MSREs in combination.

In some embodiments, the amplicons are divided into two aliquots wherein one aliquot is subjected the methods described above, and the second aliquot is subjected to whole exome-capture and exome-seq (WES), or whole genome sequencing (WGS) to identify mutations in the amplicons.

In some embodiments, the CpG rich amplicons are enriched prior to sequencing. Enrichment can include, for example, fragmenting the amplicons followed by size selection of the fragmented amplicons containing CpG rich sequences, preferably in the size range of about 100 bp to about 500 bp. Fragmenting of the amplicon can be accomplished by digesting the amplicons with one or more restriction endonucleases that typically cut unmethylated CpG islands or other CG-rich sequences (cDMRs) into short fragments with the size mostly ranging from about 50 bp to about 500 bp, while the CpG-poor fragments are mostly >>500 bp, wherein the RE are preferably selected from: (1) one of the group consisting of 4-Nt such as HpaII (or MspI), BstUI, AciI, HinP1I (or HhaI), HpyCH4IV, FauI, TaqI, and (2) a combination of multiple 5-Nt RE such as BsaW1 and HaeII, or 6-Nt MSREs, or a combination thereof.

In some embodiments, enriching the CpG rich amplicons includes shearing the amplicons randomly to appropriate size of fragments, preferably between about 50 bp and about 500 bp, by a biological, physical or chemical means. Some embodiments include collecting the CG-rich amplicons by contacting the amplicons with a reagent that binds to methylated or unmethylated CG-rich sequences to enrich the sequence, and eluting the bound DNA fragments. The reagent can be, for example, methylated CpG-rich DNA binding protein, unmethylated CpG-rich DNA binding protein, an antibody that can captures methylated-C containing DNA fragments, wherein if the reagent binds to methylated CpG sequences, the amplicons are first methylated, preferably by HpaII methyltransferase when the first MSRE used in digestion of the genomic DNA is HpaII, or HhaI transferase when the first MSRE used in digestion of the genomic DNA is HhaI, or the universal DNA methyltransferase such as Human DNA (cytosine-5) MTase (Dnmt1) or CpG Methyltransferase (M. SssI).

Some methods of identifying cDMRs for a genome include isolating nucleus (or nuclei) from an intact whole cell or cells to access genomic DNA under conditions that maintain double strandedness and reduce, minimize, or prevent random shearing of the genomic DNA; digesting the genomic DNA with one or more restriction endonucleases (REs) which recognize and cut CpG islands or other CpG rich sequence blocks (cDMRs) predominately into short fragments ranging from about 50 bp to about 500 bp, while CpG-poor sequences or non-cDMRS are less frequently cut, yielding fragments mostly >500 bp; ligating an amplification adaptor comprising a PCR primer binding site to the ends of the fragments of genomic DNA; amplifying the adapter flanked fragments by PCR comprising extension of primer(s) that bind to PCR primer binding site in the amplification adaptors to produce amplicons; and determining the sequences of the amplicons, wherein the sequences of amplicons correspond to cDMRs.

In some embodiments, genomic DNA is digested with one or more non-MSREs which recognize CpG-rich sequences, preferably selected from the group consisting of MspI, Taq-alpha-I, BsaWI, and other non-MSREs that cut the genomic DNA regardless of their CpG methylation status. In some embodiments, the genomic DNA is first amplified by MDA using 4 nucleotides (dATP, dTTP, dCTP, dGTP) prior to digestion, and wherein digesting the non-methylated amplicon includes use of one or more non-MSREs which recognize CpG-rich sequence, preferably selected from the group consisting of MspI, Taq-alpha-I, BsaWI, and other non-MSREs that cut the genomic DNA regardless of their CpG methylation status, or MSRE that enrich CpG-rich sequence, preferably selected from the group of 4-Nt to 6-Nt.

In some embodiments, a method of identifying unmethylated DMRs includes, isolating nucleus (or nuclei) from an intact whole cell or cells to access genomic DNA under conditions that maintain double strandedness and reduce, minimize, or prevent random shearing of the genomic DNA; digesting the genomic DNA with one more MSREs to generate fragments of genomic DNA, wherein MSREs frequently cut unmethylated CpG such that the CpG islands or other CpG-rich sequence blocks (cDMRs) are typically cut into fragments of about 50 bp to about 500 bp, but non-cDMRs are less frequently cut, yielding fragments mostly >500 bp; ligating an amplification adaptor comprising a PCR primer binding site to the ends of fragments of genomic DNA; amplifying the adapter flanked fragments by PCR comprising extension of primer(s) that bind to PCR primer binding sites in the amplification adaptors to produce amplicons; and determining the sequences of the amplicons wherein the sequences of amplicons correspond to unmethylated DMRs. Some methods include mapping the unmethylated DMRs to the sequence of the genomic DNA.

Some methods of identifying methylated DMRs include identifying unmethylated DMRs as discussed above; mapping the unmethylated DMRs the sequence of the genomic DNA; identifying DMRs as methylated DMRs by subtracting the unmethylated DMRs from a collection of cDMRs, wherein the cDMR and unmethylated DMR are prepared using the same REs and/or MSREs.

In some embodiments, a method of identifying methylated DMRs includes isolating nucleus (or nuclei) from an intact whole cell or cells to access genomic DNA under conditions that maintain double strandedness and reduce, minimize, or prevent random shearing of the genomic DNA; digesting genomic DNA with one or more non-MSRE, preferably the same set of REs as is used to prepare cDMR; ligating an amplification adaptor comprising a PCR primer binding site to the fragments of genomic DNA; treating the fragments flanked with adapters with one or more MSREs; amplifying the adapter flanked fragments by PCR comprising extension of primer(s) that bind to PCR primer binding site in the amplification adaptors to produce amplicons; and determining the sequences of the amplicons, wherein the sequences of amplicons correspond to methylated DMRs. The MSREs can be, for example, (1) one or more MSREs, preferably selected from the group consisting of BstUI, HinpII, HhaI, AciI, and HpaII, wherein HpaII can be used if MspI in the first digestion, (2) two or more 6-Nt MSREs, or a combination thereof. In some embodiments, the methylated DMRs are mapped to the sequence of the genomic DNA.

In some embodiments, a method of identifying unmethylated DMRs includes identifying methylated DMRs; mapping the methylated DMRs the sequence of the genomic DNA; and identifying DMRs as unmethylated DMRs by subtracting the methylated DMRs from a collection of cDMRs preferably generated according to the methods described above, and wherein the cDMR and unmethylated DMR are prepared using the same REs and/or MSREs.

In some embodiments, a method of preparing a CpG methylation profile at single nucleotide resolution by reduced representation covering DMRs of CpG islands, CpG shores, and other CpG-rich sequence blocks, includes (a) isolating nucleus (or nuclei) from an intact whole cell or cells to access genomic DNA under conditions that maintain double strandedness and reduce, minimize, or prevent random shearing of the genomic DNA; (b) digesting the genomic DNA with one or more non-MSRE which recognize CpG rich sites, preferably selected from the group consisting of MspI, Taq-alpha-I, BsaWI, and one or more REs that cut CpG islands or other CpG rich sequence blocks (cDMRs) into mostly short fragments ranging from about 50 bp to about 500 bp independent of whether the CpG islands or other CpG rich sequence blocks (cDMRs) are methylated or unmethylated, and wherein CpG-poor sequences or non-cDMRS are less frequently cut, typically into fragments >500 bp; (c) ligating an amplification adaptor comprising a PCR primer binding site to the ends of the fragments of genomic DNA, wherein all cytosines of the adaptor are methylated; (d) subjecting the adaptor ligated fragments to bisulfite conversion; (e) amplifying the adapter flanked, bisulfite converted DNA fragments by PCR comprising extension of primer(s) that bind to PCR primer binding sites in the amplification adaptors to produce amplicons with a nucleotide-U-compatible thermal stable Taq DNA polymerase, preferably EpiTaq HS to produce amplicons; (f) sequencing the amplicons; and (g) determining if each of the cystosines is methylate or unmethylated. Some embodiments include mapping the sequence reads to the genome.

In some embodiments, the amplification adaptors include a short oligonucleotide hybridized to the 3' end of a longer oligonucleotide such that the adaptor forms a cohesive end, wherein the 3' end of the longer oligonucleotide can be covalently ligated to the 5' phosphate of the fragment. In some embodiments, the short or long oligonucleotide of the adapter are sequence variable at one end, such that it constitutes a mixture of multiple cohesive ends compatible to multiple the restriction endonucleases (REs or MSREs) that are used to generate the appropriately short genomic DNA fragments of CpG islands or other CpG-rich sequences (cDMRs).

In some embodiments, the ligation step is followed by heat denaturing/melting off the shorter oligonucleotide from the longer oligonucleotide under conditions in which the fragment remains double stranded; and making the single stranded portion of the adapter double stranded by an extension reaction that extends the 3' end of the fragment along the length of longer oligonucleotide of the adaptor to form a full length double stranded adaptor.

The adapters can be filled by a DNA polymerase that is without strand displacement activity, without 5'-3' exo activity and without 3'-5'exo activity, and preferably is *Sulfolobus* DNA Polymerase IV. Extension can be carried out by a DNA polymerase that has no activity of nick translation, nor strand displacement. In some embodiments, the adaptors include a Type IIs restriction endonuclease site. In some embodiments, the adaptor sequences can be completely removed by digestion with the Type IIs restriction endonuclease. The Type IIs restriction endonuclease can cut and remove the adapter such that the remaining DNA fragments have an addition A-overhand at the 3' end, which can be directly ligated to sequencing adapters. In some embodiments, the endonuclease is BciVI and the sequence recognition site is ((GTATCCNNNNNN (SEQ ID NO:19) GGA-TAC (SEQ ID NO:76) (6/5)) or another sequence that can be cut by BciVI. The adaptor can include or consist of methylcytosine in place of cytosine, and wherein the extension reaction is processed with 3 conventional nucleotides dATP, TTP and dGTP plus nucleotide methylCytosine (dmCTP).

In some embodiments, both the longer full length oligonucleotide as well as the short oligonucleotide are unmethylated at every "C" of all of the "C" sites, wherein during the extension/filling-in step 4 conventional nucleotides (dATP, dTTP, dGTP and dCTP) are provided, wherein the sequences of the 2 oligonucleotides are designed such that after bisulfite conversion, the PCR primers are exactly matching the bisulfite converted product, and after PCR amplification, the amplicon sequences corresponding to the adapters include a desired recognized site for a type IIs site, preferably BciVI.

In some embodiments, the longer oligonucleotide of the adaptor comprises the nucleic acid sequence GAT GCT GTA AAG TTG AAG TAG GTA TCC GTG AG*T (SEQ ID NO:20), wherein * is optionally a nuclease blocking modification, such as phosphorothioate. In some embodiments, the shorter oligonucleotuide includes the sequence CGACT-CACGGAT (SEQ ID NO:21). In some embodiments, the PCR primer for the PCR amplification completely or partially hybridizes to the complement of the longer oligonucleotide.

A method of identifying CpG methylation profile at single nucleotide resolution on the whole genome can include isolating nucleus (or nuclei) from an intact whole cell or cells to access genomic DNA under conditions that maintain double strandedness and reduces, minimizes, or prevents random shearing of the genomic DNA; subjecting the genomic DNA to bisulfite conversion in the presence of a synthetic oligonucleotide carrier; amplifying the output DNA with Sequenase or by random PCR amplification with a DNA polymerase that is compatible with a bisulfite treated DNA template.

IV. Compositions and Techniques for Use in the Disclosed Methods

A. Cells

The methods disclosed herein are capable of preparing representative chromatin and/or methylation status profiles from single and low quantities of cells. Therefore, in some embodiments, the number of starting cells is less than 100,000 cells, less than 10,000 cells, less than 1,000 cells, less than 100 cells, less than 10 cells, or is 1 cell. The cells can be eukaryotic or prokaryotic. 70.

B. Isolation of Nuclei

The accessing or isolation of genomic DNA can be part of any of the methods disclosed herein, or can take place prior to the method. The disclosed methods typically utilize genomic DNA accessed from a single cell or low quantities of cells. Low numbers of cells contain a low quantity of genomic DNA. For assays utilizing one or low quantities of cells, it can be important to prevent loss genomic DNA to ensure sufficient intact genomic DNA is available for analysis. Therefore, in preferred embodiments the genomic DNA is accessed using a mild or gentle cell lysis protocol. Preferably the method does not include phenol-chloroform, column or electrophoresis-based DNA purification. In some embodiments, the reactions are carried out in a single tube. In a particular embodiment, DNA purification through amplification is carried out in a single tube. Agarose blocks, such as those describe above, can be used to package cells and further reduce physical DNA shearing. The DNA is to be isolated or otherwise separated or distanced from the DNA binding proteins and other cellular materials such that these materials do not interfere with the enzymatic reaction(s) and/or other treatments of the DNA.

In preferred embodiments, the genomic DNA is accessed under conditions that maintain the DNA as double stranded DNA at least until after the DNA is treated by a first restriction digestion. For example, alkaline or protein or enzyme (such as protease K) denaturation at high temperature (>90° C.) should be avoided.

In DHRS/chromatin structure analysis methods, DNA binding proteins and the DNA in its original nature form should be maintained at least until DNaseI or anther DNase or physical or chemical means is used to discriminate the condensed from open chromatin. The nucleus or nuclei can be separated from the rest of the cell (e.g., the cell membrane, cytoplasm, etc.), however, in these methods gDNA should not initially be separated from the DNA binding protein.

It will be appreciated that maintaining doublestrandness is particularly preferred for CpG methylation analysis, and less important for chromatin (DHRS) analysis.

In some embodiments, isolating or accessing genomic DNA includes deproteinizing the DNA in a buffer under conditions that reduce, minimize, or prevent DNA loss and DNA denaturation and precipitation of the DNA from the buffer. The precipitation can include contacting or combining the DNA with a carrier, sodium acetate, and ethanol or isopropanol applied and collecting of the DNA as pellet, followed by washing the pellet with 70-80% ethanol, and resuspension of the pellet. The deproteinization can include contacting the genomic DNA with a chaotrope, preferably guanidine hydrochloride (GndCl), Guanidinium thiocyanate (GuTC), urea, thiourea, sufactants, a detergent preferably NP-40, TritonX-100, IGEPAL CA-630, CHAPS, Zwittergent. The deproteinization can include treating the genomic DNA with a heat sensitive protease. The precipitation can include contacting or combining the DNA with a non-nucleic acid DNA carrier preferably selected from the group consisting of GenTLE, glycogen, a synthetic RNA carrier (such as Terminal Nucleotidyl Transferase synthesized polyA) and linear acrylamide, with sodium acetate at a concentration of 10-20%, and then with ethanol (2-3 volumes) or isopropanol (0.5 to 1 volume), followed by centrifugation until the DNA forms a pellet, followed by wash with 70-80% ethanol, and resuspension of the DNA.

In some embodiments, the genomic DNA is obtained or accessed by lysing 1 cell, lysing 1-10 cells, lysing 1-100 cell, lysing 1-1,1000 cells, or lysing 1-10,000 cells.

In some embodiments, the cells are embedded and processed accordingly to the disclosed methods in a low melt agarose, such as 0.5 to 3%, or specifically 1.0% low-melt gel agarose.

In some embodiments, all steps prior to amplification are carried out in a single tube. In some embodiments, all the steps prior to amplification are carried out in a small volume, or with microfluidics.

C. Methylation Sensitive Restriction Enzymes (MSREs)

Many of the disclosed methods include one or more restriction digestions with a MSRE. These restriction enzymes are not able to cleave methylated-cytosine residues, leaving methylated DNA intact. MSREs cleave DNA at specific unmethylated-cytosine residues. MSREs are known in the art and includes variants of recognition sequences, from 4 nucleotide to 8 nucleotides, the preferred MSRE are these: 4 nucleotide recognition site MSRE (4-Nt MSRE): HpaII, BstUI, AciI, HinpII, and 6 nucleotide recognition site MSRE (6-Nt MSRE): SacII, EagI, NaeI, BssHII. Other enzymes include, but are not limited to, AatII, Acc II, AciI, AclI, AfeI, AgeI, Aor13H I, Aor51H I, AscI, AsiSI, AvaI, BceAI, BmgBI, BsaAI, BsaHI, BsiEI, BsiWI, BsmBI, BspT104 I, BspDI, BspEI1, BsrBI1, BsrFI, BssHII, BstBI, BstUI, ClaI, Cfr10 I, Cpo I, EagI, Eco52 I, FauI, FseI, FspI, HaeII, HgaI, HhaI, HinP1I, HpaII, Hpy99I, HpyCH4IV, KasI, MluI, NaeI, NarI, NgoMIV, NotI, NruI, Nsb I, PaeR7I1, PmaC I, Pml I, Psp1406 I, PvuI, RsrII, SacII, SalI, SfoI, SgrAI, SmaI, SnaBI, TillI, XhoI1. In addition, 5-Nt MSRE that can be use include, but are not limited to, FauI ((CCCGCNNNN) (SEQ ID NO:12)/ (GCGGG) (SEQ ID NO:52) (4/6)) and HgaI ((GACGCNNNNN (SEQ ID NO:18)/GCGTC (SEQ ID NO:75) (5/10)). MSREs with degenerate nucleotide recognition sites that can be used for the methods in this invention, include, but are not limited to, HaeII ((RGCGCY) (SEQ ID NO:13)), BsiEI (CGRYCG (SEQ ID NO:16)), BsrFI (RCCGGY (SEQ ID NO:14)), EaeI (YGGCCR (SEQ ID NO:15)), and Hpy99I (CGWCG (SEQ ID NO:17)). Typically, for degenerative sequences, "W" can be "A" or "T", "R" can be "A" or "G", and "Y" can be "C" or "T".

In some embodiments, the methods include one or more 4 to 6-nucleotides (4-Nt to 6-Nt) recognizing CpG island-specific MSREs, preferably selected from the group consisting of (1) one or more 6-Nt recognition site MSREs, preferably selected from the group consisting BssHII (GCGCGC(SEQ ID NO:1)), EagI (CGGCCG (SEQ ID NO:2)), KasI (GGCGCC (SEQ ID NO:22)), NaeI (GCCGGC (SEQ ID NO:4)), NarI (GGCGCC (SEQ ID NO:5)), NgoMIV (GCCGGC (SEQ ID NO:6)), PspOMI (GGGCCC (SEQ ID NO:7)), SacII (CCGCGG (SEQ ID NO:8)), SfoI (GGCGCC (SEQ ID NO:9)), and TspMI (CCCGGG (SEQ ID NO:10)); and (2) one or more 5-Nt recognition site MSREs, preferably selected from the group consisting of FauI ((CCCGCNNNN) (SEQ ID NO:12)/ (NNNNNNGCGGG)) (SEQ ID NO:52) (4/6) and HgaI ((GACGCNNNNN (SEQ ID NO:18)/(GCGTC (SEQ ID NO:75) (5/10)), or with degenerate nucleotide recognition site such as HaeII (RGCGCY (SEQ ID NO:13)), BsiEI (CGRYCG (SEQ ID NO:16)), BsrFI (RCCGGY (SEQ ID NO:14)), EaeI (YGGCCR (SEQ ID NO:15)), and Hpy99I (CGWCG (SEQ ID NO:17)); (3) one 4-Nt recognition site MSREs, preferably selected from the group consisting of Hinp1I (GCGC), HhaI (GCGC), HpaII (CCGG), BstUI (CGCG); or (4) combinations thereof.

D. MDA-Based Amplification

Some of the methods disclosed herein include an amplification step incorporating the principles of MDA. MDA is a non-PCR based, isothermal, high-displacement, random priming DNA amplification technique. This method can rapidly amplify small amounts of DNA to a reasonable quantity for subsequent analysis.

MDA can generally be carried out without purification of DNA and without denaturation of the DNA template. The MDA reaction typically includes the steps of annealing primers, typically 6-9 mer random primer, to a DNA template, for example the genomic DNA or fragments thereof. DNA synthesis is carried out by a high fidelity enzyme, preferentially phi29 DNA polymerase, typically at a constant temperature. Compared to conventional PCR amplification techniques, MDA generates larger sized products with a lower error frequency.

Methods of using MDA for whole genome amplification are known in the art. MDA reactions typically include diluting the DNA template in an appropriate reaction buffer ($Ca_2+$ and $Mg_2+$ free). An MDA reaction with phi29 polymerase is typically carried out at 30° C., plus or minus 1, 2, 3, 4, 5, 6, 7, 8, 9, 10, or more degrees. Preferably, the reaction is carried out a temperature between about 26° C. and 40° C. more preferably between about 28° C. and 35° C.

A typical reaction can be about 1 to about 16 hours. In a particular embodiment MDA amplification of DNA is carried out with trehalose in the reaction mixture are typically longer, for example 3, 4, 5, 6, 7, 8, 9, 10, 12, 13, 14, 15, 16, or more hours. Preferably the reaction is carried out for between about 10 and 16 hours. Longer reactions can increase yield.

At the end of the reaction, the enzymes are typically, but optionally, inactivated by heat (e.g., several minutes at about 65-75° C.) before collection of the amplified DNA products.

Some MDA methods are known in the generate template independent product (TIP). This TIP synthesis is largely oligonucleotide-derived, but exogenous DNA contamination can also contribute. When the input is limited, such as with a subnanogram amount of template DNA or a limited number of cells, TIPs are very abundant, often representing 70-75% of the total yield. TIPs can significantly impair some of the applications of the amplicon. Therefore, in some embodiments, one or more methods of reducing TIP are employed in the MDA-based DNA amplification methods disclosed herein.

Several efforts have been made to eliminate TIP and improve the specificity of MDA (Hutchison, et al., *Nat Biotechnol.*, 24:657-658 (2006), Hutchison, et al., *Proc Natl Acad Sci USA*. 102:17332-17336 (2005), Zhang, et al., *Nature Biotechnol.*, 24:680-686 (2006), Lage, et al, *Genome Res.*, 13:294-307 (2003), Wang, et al., Nucleic Acids Res., 32:e76. (2004), Brukner, et al, *Anal Biochem.*, 39:345-347 (2005), Inoue, et al., *Nucleic Acids Res.*, 34:e69 (2006). The outstanding examples include steps for strict control of experimental procedures to avoid exogenous DNA contamination (Zhang, et al., *Nature Biotechnol.*, 24:680-686 (2006)), and minimization of the reaction volume (600 to 60 nl) (Hutchison, *Proc Natl Acad Sci USA*, 102:17332-17336 (2005), Marcy, et al. *PLoS Genet.*, 3:1702-1708 (2007)) or the reaction time (Spits C, et al., *Nat Protoc.*, 1:1965-1970 (2006)).

Preferably the disclosed MDA-based methods of MDA amplification include one or more of the steps, reagents or principals described in Pan, et al., *Proc Natl Acad Sci USA*, 105(40):15499-15504 (2008) which is specifically incorporated by reference herein in its entirety. Pan, et al., describes an MDA approach, referred to therein and herein as whole-pool amplification (WPA), which provides highly specific, unbiased, and hypersensitive amplification of very small amounts of entire genomes or complex DNA pools. In a particular embodiment, the MDA-based amplification step includes a Tre [d-(+)-trehalose dehydrate] concentration that when combined with other reaction conditions robustly or completely eliminates the production of endogenous TIP.

In a particular embodiment, the MDA-based DNA amplification is based on WPA, however, it will be appreciated that the method can be modified to include alternative or additional reaction buffers or components, higher or low reaction temperatures, short or longer reaction times, modified reaction sequences, alternative reaction volumes, or combinations thereof.

Strand displacement DNA polymerases include φ29 DNA polymerase (U.S. Pat. Nos. 5,198,543 and 5,001,050 to Blanco et al.), Bst large fragment DNA polymerase (Exo(−) Bst; Aliotta et al., *Genet. Anal. (Netherlands)* 12:185-195 (1996)), exo(−)Bca DNA polymerase (Walker and Linn, *Clinical Chemistry* 42:1604-1608 (1996)), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), exo(−)VENT® DNA polymerase (Kong et al., *J. Biol. Chem.* 268:1965-1975 (1993)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), Sequenase (U.S. Biochemicals), PRD1 DNA polymerase (Zhu and Ito, *Biochim*.

*Biophys. Acta.* 1219:267-276 (1994)), and T4 DNA polymerase holoenzyme (Kaboord and Benkovic, *Curr. Biol.* 5:149-157 (1995)).

Primers for the MDA-based amplification disclosed herein generally rely on the principles of random priming. Random primer is a mixture of primers where the sequence is a random mixture of the 4 DNA bases. Random hexamer primer is commonly used in genomic amplification reactions. Random hexamer primer is typically a mixture of oligonucleotides, for example, 4096 different primer sequences. Although hexamers are common, the random primer can be more or less nucleotides in length, or a mixture thereof. For example, the random primer can be 5, 6, 7, 8, 9, 10, 11, or 12 nucleotides in length. In a particular embodiment, the random primer is a 9-mer.

In some embodiments, the 9-mer is 3' of a 5' non-complementary common or universal sequence can be used as a bind site for PCR primers in a subsequent PCR amplification step. In the primers can also include a target site for restriction digestion. In a preferred embodiment, the site allows at least the common or universal primer binding sequence to be cleaved from the amplicon.

Primers can be phosphorylated at the 5' end. Therefore, a preferred primer for the RT step preceding MDA-based whole transcriptome amplification procedures discussed herein includes use of a 5' phosphorylated random primer.

Some of the MDA-based methods include a step of ligated fragmented or digested genomic DNA template to circularize the DNA fragments. The template can be single stranded or double stranded. The ligation reaction can be carried out under conditions that favor circularization. If necessary, the DNA can be treated to phosphorylate the 5' end of the fragments.

The DNA is circularized prior amplification using a ligase. In preferred embodiments where the DNA is double stranded, the double stranded DNA is blunt-ended prior to or during the ligation reaction. In preferred embodiments the 5' end of the DNA is phosphorylated. In a specific embodiment, The END-IT™ DNA End-Repair Kit (Epicentre) plus T4 DNA ligase (Epicentre) are combined for the DNA end blunting, 5'-end phosphorylation, and ligation. This can included END-IT™ buffer 1×, 1 mM dNTPs, 1 mM ATP, 0.8 µL total enzyme mixture, and T4 DNA ligase (0.4 U/µL). Circularization and end-repair (e.g., 5' and 3' end blunting and 5' end phosphorylation) can be employed in the same tube under the same conditions. In preferred embodiments the end is a cohesive (sticky) end. Most, including some MSRE, leave a cohesive end with 5' end phosphorylated. Cohesive ended DNA fragments usually result in higher ligation efficiency.

For the WPA or MDA-based CpGmp methods (MSRE-ligation-MDA), typical ligation is performed under conditions that drive intramolecular circularization and limits or reduces linear concatemers. These conditions lead to a more uniform amplification and more complete representation of the template compared to linear fragments. Amplification of linear fragments by MDA is more likely to amplify the middle sequences and not the end sequences, which can lead to misrepresentations during the post-amplification analysis.

The DNA can be circularized as single stranded DNA using, for example, CIRCLIGASE™ ssDNA Ligase. Alternatively, the DNA can be circularized as double stranded DNA using, for example, T4 or another double stranded DNA ligase.

In some embodiments, the ligase preferentially catalyzes intramolecular ligation. For example, the ligase can be CIRCLIGASE™ ssDNA Ligase, which is a thermostable ATP-dependent ligase that catalyzes intramolecular ligation (i.e. circularization) of ssDNA templates having a 5"-phosphate and a 3"-hydroxyl group. CIRCLIGASE™ ssDNA Ligase ligates ends of ssDNA in the absence of a complementary sequence. The enzyme is therefore useful for making circular ssDNA molecules from linear ssDNA. Therefore in a particular embodiment, the DNA is intra-molecular circularized by CIRCLIGASE™ Experimental evidence shows that it can circularize variants of sizes of single strand DNAs from approximately 10-bases to more than 10,000-bases of single strand DNAs.

In a specific embodiment circularized DNA is combined with an amplification procedure (WPA) premixture (containing buffer, trehalose, dNTPs, primer, based on the WPA procedure described in Pan, *Proc Natl Acad Sci USA*, 105(40):15499-15504 (2008)) plus RepliPHI phi29 DNA polymerase (1,000 U/µL×0.4 4160 µL; Epicentre) and fresh DTT (1 mM; Invitrogen). The MDA reaction can be carried out at between about 30° C., plus or minus up to 10° C., for between about 2 and about 16 hours. After the reactions, DNA can be isolated or separated from the other reaction components. For example, DNA can be purified using the Genomic DNA Clean and Concentrator kit (Zymo) discussed above.

MDA-based amplification of circularized DNA can also be referred to as rolling circle amplification or rolling circle replication.

MDA amplification can be carried out with, or without advanced DNA denaturation, primer annealing, and/or neutralization.

E. Polymerase Chain Reaction (PCR)

Some of the methods disclosed herein include an amplification step that includes polymerase chain reaction (PCR). PCR relies on thermal cycling, and typically includes cycles of repeated heating and cooling of the reaction for DNA melting and enzymatic replication of the template DNA. Short single stranded oligonucleotide primer(s), containing sequences complementary to the target region along with a DNA polymerase are key components to enable and repeated amplification. As PCR progresses, the DNA generated is itself used as a template for replication, setting in motion a chain reaction in which the DNA template is exponentially amplified.

PCR applications typically employ a heat-stable DNA polymerase, such as Taq polymerase. This DNA polymerase enzymatically assembles a new DNA strand from nucleotides (dNTPs), by using single-stranded DNA as a template for primer extension. The majority of PCR methods use thermal cycling, i.e., alternately heating and cooling the PCR sample through a defined series of temperature steps. In a typical PCR reaction, the two strands of a DNA double helix are physically separated at a high temperature in a process called DNA melting. Next, the temperature is lowered and the two DNA strands become templates for primer annealing and extension by DNA polymerase. The cycle can be repeated numerous times to amplify further amplify the template DNA. Numerous variations on PCR-based strategies are known in the art, and can be incorporated into or used to optimize the disclosed methods.

When PCR is used for the initial amplification step, as in the disclosed PCR-based methylation analysis methods, the PCR primer(s) typically bind to a pre-determined primer binding sequence (also referred to herein as a common or universal or adapter sequence). The sequence can be incorporated into amplification adaptors or generated during the filling-in step after the adaptors are ligated to the fragmented genomic DNA following the first restriction digestion. Any suitable primer(s) can be utilized provided it binds to and amplifies the genomic DNA fragment encompassed by the amplification adaptors. Accordingly, the primer(s) is designed in concert with the amplification adaptors. In some embodiments, the common sequence is designed such that the same primer can be used for forward and reverse priming. PCR primers can also be used to incorporate additional non-complementary sequences into the amplicon, for example, bar codes and sequencing primer binding site(s) for downstream analysis. The bar code can be identified by the binding of a bar code probe that hydrides to the bar code (or its reverse complement) and can be detected with a detectable label. Preferably, the bar code is a sequence that can be identified during sequencing of the amplicon.

Methods of selecting a suitable sequence, length, G/C content, etc., of the primer(s) and construction a suitable, associated PCR reaction protocol are known in the art and may incorporate considerations such as sequence frequency in the genome (e.g., it may be desirable to use an infrequent or unique primer binding sequence in the adaptor to avoid non-specific amplification during the PCR step) and melting temperature that can be accommodated by thermocycling.

Other PCR reactions disclose herein can utilize primers designed to amplify a specific genomic sequence. Such methods are most typically used to analyze the amplicons, for example by probing the amplicons for the presence (or absence) of a specific region of the genome as discussed in more detail below and exemplified in the working examples.

Methods of designing such primers are also known in the art and in some cases commercially available.

In some embodiments, the amplification adapter includes a bar code. The bar code can be a combination of a limited, fixed number of nucleotides, as the barcode for each sample, at the adapter end that is directly ligated to the end of the fragments generated from the target DNA. In some embodiments, the barcode nucleotide number is 1, 2, 3, 4, 5, 6, 7, 8, 9, 10, 11, 12, 13, 14, 15, 16, 17, 18, though it is most typically about 6 to about 8 nucleotides. In some embodiments, the individual samples with different barcoded adapters are pooled together for the downstream processing after the adapter ligation and before PCR amplification In some embodiments, the adapters include 2 oligos:

Long-ad1-b (with all C methylated as mC): 5'-GAT GCT GTA AAG TTG AAG TAG GTA TCC GTG AGT NNNNN*N-3'(SEQ ID NO:25) (wherein the * is phosphothiate modification for the last nucleotide); and Short-ad1-b (no mC): 5'MM.nnnnnnCTCACGGAT-3' (SEQ ID NO:26).

"NNNNNN" is a barcode with 6-nucleotide; "nnnnnn" is a reverse complementary sequences for the 6 nucleotide of; MM is the cohesive end that is generated with the RE digestion, e.g., when the RE is MspI, the MM is CG (the Short-ad1-b will be 5'CG.nnnnnn CTCACGGAT-3' (SEQ ID NO:27).

Exemplary bar code sequences pairs below SEQ ID NO:28-49 and (SEQ ID NO:53-74), can be used for "NNNNNN" and ("nnnnnn") respectively in the above adaptor sequences (e.g., SEQ ID NO:25, 26, and 27).

| | | | | |
|---|---|---|---|---|
| b1. | ATCACG | (SEQ ID NO: 28) | (CGTGAT) | (SEQ ID NO: 53) |
| b2. | CGATGT | (SEQ ID NO: 29) | (ACATCG) | (SEQ ID NO: 54) |
| b3. | TTAGGC | (SEQ ID NO: 30) | (GCCTAA) | (SEQ ID NO: 55) |
| b4. | TGACCA | (SEQ ID NO: 31) | (TGGTCA) | (SEQ ID NO: 56) |
| b5. | ACAGTG | (SEQ ID NO: 32) | (CACTGT) | (SEQ ID NO: 57) |
| b6. | GCCAAT | (SEQ ID NO: 33) | (ATTGGC) | (SEQ ID NO: 58) |
| b7. | CAGATC | (SEQ ID NO: 34) | (GATCTG) | (SEQ ID NO: 59) |
| b8. | ACTTGA | (SEQ ID NO: 35) | (TCAAGT) | (SEQ ID NO: 60) |
| b9. | GATCAG | (SEQ ID NO: 36) | (CTGATC) | (SEQ ID NO: 61) |
| b10. | TAGCTT | (SEQ ID NO: 37) | (AAGCTA) | (SEQ ID NO: 62) |
| b11. | GGCTAC | (SEQ ID NO: 38) | (GTAGCC) | (SEQ ID NO: 63) |
| b12. | CTTGTA | (SEQ ID NO: 39) | (TACAAG) | (SEQ ID NO: 64) |
| b13 | AGTCAA | (SEQ ID NO: 40) | (TTGACT) | (SEQ ID NO: 65) |
| b14 | AGTTCC | (SEQ ID NO: 41) | (GGAACT) | (SEQ ID NO: 66) |
| b15. | ATGTCA | (SEQ ID NO: 42) | (TGACAT) | (SEQ ID NO: 67) |
| b16. | CCGTCC | (SEQ ID NO: 43) | (GGACGG) | (SEQ ID NO: 68) |
| b17. | GTAGAG | (SEQ ID NO: 44) | (CTCTAC) | (SEQ ID NO: 69) |
| b18. | GTCCGC | (SEQ ID NO: 45) | (GCGGAC) | (SEQ ID NO: 70) |
| b19. | GTGAAA | (SEQ ID NO: 46) | (TTTCAC) | (SEQ ID NO: 71) |
| b20. | GTGGCC | (SEQ ID NO: 47) | (GGCCAC) | (SEQ ID NO: 72) |
| b21. | CGAAAC | (SEQ ID NO: 48) | (GTTTCG) | (SEQ ID NO: 73) |
| b22. | CGTACG | (SEQ ID NO: 49) | (CGTACG) | (SEQ ID NO: 74) |

F. Fragmentation

MDA-based amplification procedures typically generate products of approximately 10 to 12 kb products, while PCR-based procedures typically generate of about products of greater than about 80 bp up to about 4 kb, however, 3-4 kb products can be compromised by nonspecific primer annealing, suboptimal cycling conditions, and secondary structures in the DNA template. In some embodiments, the products can be longer or shorter. For some uses of the amplicons, for example, sequencing and microarray analysis, it can be preferred to have a DNA library composed of DNAs having lengths predominately between about 100 and 5,000 base pairs, or 100 and 500 base pairs, or between about 1,000 and 3,000 base pairs. In a particular embodiment, the DNA lengths are predominately about 3,000 base pairs.

Therefore, optionally, the amplicon is fragmented. Preferably the amplicon is fragmented such that the majority of the amplicons are a size ranging from about 100 and 5,000 base pairs, or 100 and 500 base pairs, or between about 1,000 and 3,000 base pairs. In a particular embodiment, the amplicon lengths are predominately about 3,000 base pairs. In preferred embodiments, the amplicons are of a length appropriate for library construction and sequencing using Illumina HiSeq equipment.

In some embodiments, DMRs are enriched. Some methods for CpG enrichment are described above. In some embodiments, the original non-amplified, native DNA is digested with some CG-rich RE such as HpaII, AciI, BstUI, Hinp1I. In some embodiments, after amplification and fragmentation (by the REs as described above, or physical or chemical process), the DNA fragments are end-repaired, the 5' end is phosphorylated, and/or A-tailed. Sequencing adapters can be ligated and the shorter DNA fragments (e.g., fragments about 45-400 bp plus the adapter size) can be recovered by PCR. Combined with this, a pre-digestion (either with the original native gDNA, or amplified DNA) will enrich the sequences from CpG islands and CpG shores and other CpG rich sequences such as many promoters, particularly following PCR-based methods. Other CG rich 4-nucleotides-recognizing REs may be separately applied with different aliquots of the same amplicon to further improve the coverage of the desired CpG rich sequences. When no CG-rich 4-nucleotide RE is employed but the amplicon is randomly fragmented with chemical or physical process, a process such as MethylCollector™ Ultra or MBD binding column (combining with a pre-methylation), or unMethylCollector™ Ultra may be utilized to enrich the CG rich sequences.

Suitable sizes can be determined based on the intended use, e.g. sequencing or microarray analysis, which are known in the art. Methods of fragmenting DNA are also known in the art and include enzymatic methods (e.g., endonucleases), and mechanical methods (e.g., sonication). In a preferred embodiment, amplicons are sonicated. In another embodiment amplicons are treated with DNase I. In some embodiments, the fragmented amplicons are separated by size to collect a specific size or size range of fragments for later analysis.

In some embodiments, primer binding sequences (e.g., universal or common sequences) are removed before fragmentation and/or before sequencing library construction. If the typical product size resulting from amplification is beyond the size suitable for sequencing library construction, fragmentation can be applied before conventional sequencing library construction protocols are employed. In a particular embodiment, the amplicons from either MDA-based or PCR-based amplification methods and prepared for sequence directly, without fragmentation, even if the product is very long.

G. Semi-Random Primed PCR-Based Amplification

Semi-random primed PCR-based methods of DNA amplification are also provided for use in the disclosed methods. A similar semi-random primed PCR amplification of Chromatin-Immunoprecipitation generated DNA was also discussed in Adli, et al., *Nat Methods,* 7(8): 615-618 (2010), which is specifically incorporated by reference herein in its entirety and including supplemental materials.

1. Reaction Procedure

Typically, DNA amplification by semi-random primed PCR includes at least two steps. A first step includes 1, 2, 3, 4, 5, 6, or more cycles of denaturing of the DNA, primer annealing to the DNA, and extending of the primer. The primer utilized in the step includes a common or universal sequence, which is incorporated at the end of the cDNA and serves as a site for PCR primer binding. In some embodiments, the universal sequence was also or alternatively incorporated into the cDNA during the RT reaction. Primer extension is preferably carried out with one or more polymerases with strand displacement capability but no 3'→5' exonuclease activity. Other exemplary polymerases include, but are not limited to, exo-Bea polymerase, exo-Vent polymerase, exo-Deep Vent polymerase, exo-Bst polymerase, exo-Pfu polymerase, exo-Bca polymerase, the Klenow fragment of DNA polymerase I, T5 DNA polymerase, Phi29 DNA polymerase, phage M2 DNA polymerase, phage PhiPRD1 DNA polymerase, Sequenase, PRD1 DNA polymerase, 9° Nm™ DNA polymerase, or T4 DNA polymerase homoenzyme. In a particular embodiment, the polymerase is Sequenase V2.0 (see also See, for example, Lieb et al., *Nat Genet.,* 28:327-343 (2001)).

Following the first step, excess semi-random primer can be inactivated, for example, by exonuclease and alkaline phosphatase treatment.

For example, first, four cycles of random priming are carried out by the 3' end of a mixture of semi-random primer, a semi-random oligonucleotide with a 9-mer random nucleotide tag at the 3' end, and a universal sequence at its 5' end, which contained a hairpin structure, and a site for restriction endonuclease recognition. Using these conditions and reagents, each DNA molecule is represented by multiple overlapping DNA constructs, each flanked by the universal sequence. The hairpin in the semi-random primer minimized the formation of primer-dimers during these steps. Excess oligonucleotide semi-random primer can be digested with ExoSAP-IT.

In a particular embodiment, a first cycle includes denaturing cDNA with semi-random primer and reaction buffer at about 98° C. briefly, and then annealed at about 8° C. for about 5 min. Reaction mixture including polymerase, dNTPs, DTT is added. The temperature was gradually increased to about 37° C. and incubated for about 8 min. The whole cycle can be repeated 1, 2, 3, or more time with the addition of 1.2 µl of diluted polymerase (1:4) instead of the enzyme mix.

In a second step, the product from the first step is PCR amplified using a primer that binds to the reverse complement of the universal sequence introduced at the ends of the DNA during the first step. Reaction reagents and conditions for PCR amplification are known in the art. Constructs can be uniformly amplified by PCR using the universal sequence of semi-random primer as the PCR primer. An exemplary PCR step can include 15 cycles of denaturation (98° C. for 30 sec), annealing (40° C. for 30 sec and 50° C. for 30 sec)

and extension (72° C. for 1 min). When the Sequenase v2 is used, the lid is typically set at a low temperature, for examples at 40° C., because this enzyme is very heat-sensitive.

In a preferred embodiment, semi-random primer includes restriction sites that are incorporate into the DNA amplicons. The restriction site are incorporated into the primer design in such a way that treatment with the restriction enzyme can be used to remove most, preferable all of the universal primer sequences from the DNA following PCR amplification. This is typically carried out by treating the DNA with the restriction enzyme that cuts the DNA at the introduced restriction sites. In a particular embodiment, the restriction enzyme is of Type IIs. Type IIs restriction endonucleases include, but are not limited to BmrI, HphI, MboII, and MnlI. In a specific particular embodiment, the primer 1 introduces a BciIV restriction site and the cDNA is contacted with BciIV after PCR amplification.

After the reaction, DNA can be separated from the other reaction components. For example, DNA can purified using the GENOMIC DNA CLEAN AND CONCENTRATOR™ kit (Zymo) or DNA CLEAN AND CONCENTRATOR™ 5 kit (Zymo) discussed above.

Reaction conditions can be adjusted depending on the starting cell number of DNA quantity. In some embodiments, amplicon can be longer (100 bp to 1 kb) than the size range (100-550 bp) allowed for library construction, and fragmentation (by sonication) after removal of the artificial sequence introduced in the amplification improves the representation of the transcriptome. In a particular embodiment, a higher concentration of primers or additional more cycles of reaction in the first step shortens the size of the amplification products from the second step.

2. Primer Design a. Semi-Random Primer

The random primer of semi-random PCR amplification, also referred to herein as semi-random primer and primer 1, is used to introduce common or universal primer sites into the DNA. Semi-random primer is actually a mixture of primers that includes a 3' random sequence and 5' universal primer sequence. The number of primers in the mixture is determined by the number of different sequences need to randomly, but effectively, introduce the universal primer sequence onto the ends of cDNA at fragments lengths (e.g. distance between primer sites) suitable for amplification by PCR. The random sequence is a random mixture of the 4 DNA bases. The length of the random sequence in semi-random primer is typically between about 5 and 12 nucleotides, preferably, between about 6 and 11 nucleotides in length, more preferably between about 7 and 10 nucleotides in length. Random hexamer mixes consisting of 4096 sequences, are commonly used for RT reactions. The random sequence of the semi-random primer used in the Examples below is 9 nucleotides in length. Each of these primers will anneal anywhere the complementary sequence exists within a given cDNA molecule.

The universal primer sequence is of a length and sequence that is suitable for amplification of the cDNA by PCR during step 2 of the semi-random PCR amplification produced discussed above. Parameters for designing primer sequences are known in the art. For example, the universal primer sequence can be 5, 6, 7, 8, 9, 10, 11, 12, 13, 14, 15, 17, 18, 19, 20, or more nucleotides in length. Preferably, the universal primer sequence is between about 10 and about 15 nucleotides in length.

Preferably, semi-random primer includes a sequence that allows the formation of a 5' hairpin or hairpin loop to reduce or prevent primer-dimer formation. Methods of designing such a sequence are known in the art and can include, for example, a palindromic sequence. The hairpin or hairpin loop should not prevent binding and extension of the random primer sequence to the DNA.

Preferably, semi-random primer also includes a restriction site that allows part, or preferably all, of the universal sequence to be removed from the cDNA following PCR amplification by treatment with a restriction enzyme, for example a type IIs enzyme. Suitable restriction sites are known in the art. An exemplary sequence is the restriction site for BciVI, which is ((GTATCCNNNNNN (SEQ ID NO:19) GGATAC (SEQ ID NO:76) (6/5)).

An exemplary primer 1 is 5'-GACATGTATCCGGAT-GTNNNNNNNNN-3', wherein "N" is (A, T, G, or C) (SEQ ID NO:50).

b. Primer 2—Universal Primer

The sequence of a universal primer, also referred to as the common primer, or primer 2, is determined by the sequence of the 5' universal primer sequence of primer 1. The universal primer should be able to hybridize by complementary base pairing with the reverse complementary sequence generated by the universal sequence of primer 1 during the first step, and which can be extended by PCR. Therefore, the universal primer sequence typically includes a sequence that is substantially the same as the universal sequence of primer 1, or is the same as the universal sequence of primer 1.

A universal primer can that used with the exemplary primer 1 is 5'-GACATGTATCCGGATGT-3' (SEQ ID NO:51).

V. Generating Profiles and Downstream Analysis

The amplicons produced using the chromatin and methylation analysis methods discussed above can be coupled with a number of known techniques to generate a profile based on the produced amplicons and/or to analyze the data encompassed by the amplicons. The test assays between two or more different cell types, cell states, etc., are typically compared to determine if the two different cell types, cell states, etc., have differentially methylated regions or regions of differential chromatin structure. In some embodiments, test assays are compared to a control or standard.

Figure 7A:
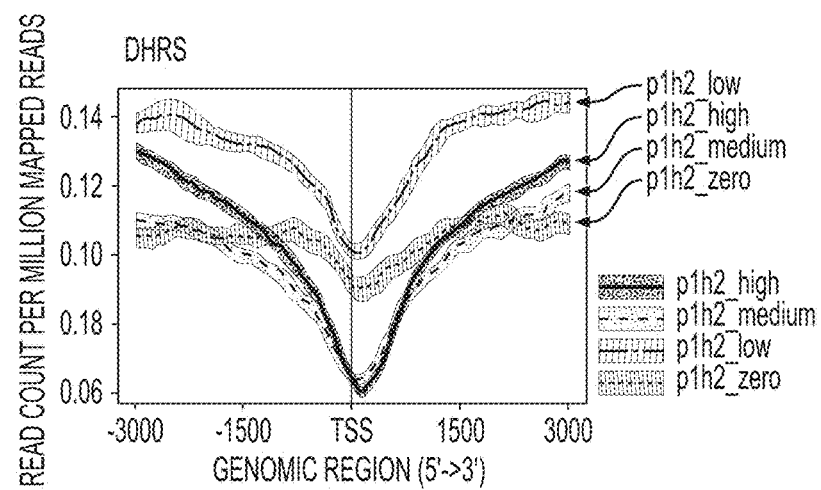
FIG. 7A is a plot showing DHRS regions (read count per million mapped reads) relative to the location of 4 known gene expression levels (high, medium, low, and zero) centered on a transcription start site (TSS).
Figure 7B:
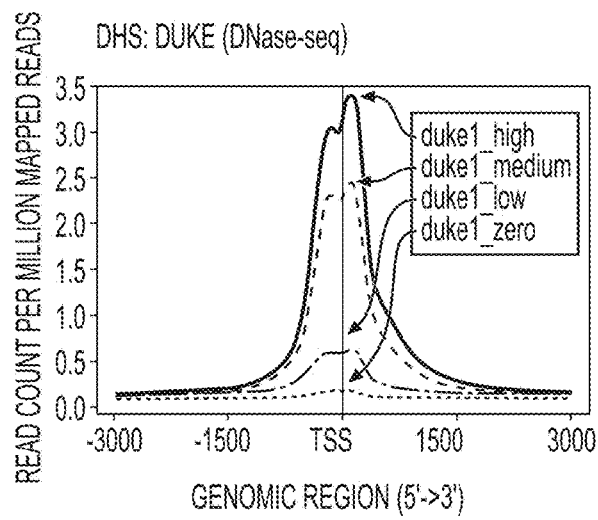
FIGS. 7B and 7C are plots showing the controls, DHS regions (read count per million mapped reads) relative to the location of 4 known gene expression levels (high, medium, low, and zero) centered on a transcription start site (TSS) for two known data sets of DHS: Duke (DNase-seq) (7B) and UW (FARE-seq) (7C). Refseq genes with 0 RPKM (3,110 genes) are categorized as "no" expressed genes. Refseq genes with more than 0 RPKM are classified into 3 classes ("high", "medium" and "low").
Figure 7C:
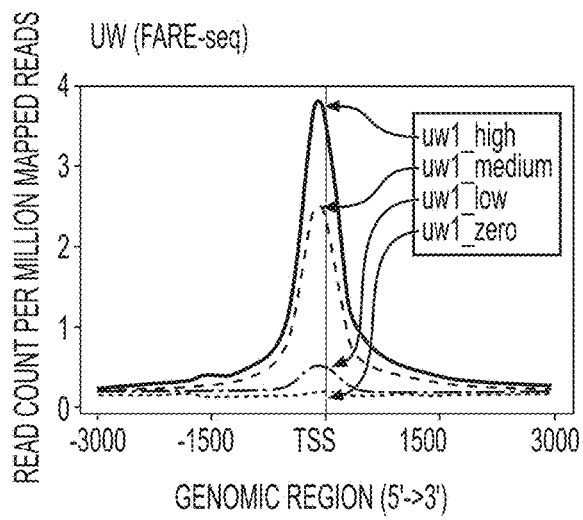

For example, in some embodiments, one or more regions identified as methylated in one cell type or state is unmethylated in a second cell type or state. In some embodiments, one or more regions identified as unmethylated in one cell type or state is methylated in a second cell type or state. Likewise, in some embodiments, one or more regions identified as DHRS in one cell type or state are absent in a second cell type or state. In some embodiments, one or more regions identified as DHS in one cell type or state are absent in a second cell type or state. Therefore, in some embodiments, methylated and unmethylated regions are mapped by empirically determining the methylated regions or unmethylated regions and determining the other by subtractive analysis. Likewise, in some embodiments, DHS and DHRS regions are mapped by empirically determining the DHS or DHRS regions and determining the other by subtractive analysis. It will be appreciated, as discussed in more detail above, that DHS and DHRS are at two ends of sliding scale of a chromatin structure's sensitivity to DNaseI. As shown in FIG. 7, they are generally reverse correlated to each other. However, there are also many sequence blocks that are neither of DHS or DHRS.

As discussed in more detail below, downstream analysis can be carried out by next generation sequencing (NGS), PCR (e.g., qPCR), Sanger sequencing, microarray (for CpG methylation pattern), or other platforms. Therefore, in some embodiments the amplicons are sequenced. In some embodiments, the amplicons are not sequenced. Genome wide and reduced representative sequence CpG methylation patterns and profiles can be obtained. In some embodiments, the profile is at the single nucleotide level (e.g., specific nucleotides within the genome are determined to be methylated or not methylated, and can be compared to known samples to identify polymorphorphic methylation sites). Such methods most typically include bisulfite sequencing. In some embodiments, the profile is not at the single nucleotide resolution, but rather at a sequence block or DMR (differentiation methylation pattern) resolution, which gives a general pattern of CpG methylation status.

In a simple embodiment, amplicons generated according to the disclosed methods are separated by size using, for example, gel electrophoresis, or density gradient centrifugation, to prepare a profile. The profile can be compared to a control or standard, or to control DNA assayed in parallel. In this way, a profile from an experimental or unknown cell type and be compared to a control cell type to identify gross changes in chromatin architecture and/or methylation status.

In some embodiments, the amplicons are subjected to PCR. For example, in particular embodiments, primers are prepared based on a known sequence and the presence of the sequence (or its absence) among the amplicons can be determined by PCR. In this way a particular known site of chromatin modification or methylation status can be probed. In some embodiments, the PCR is qPCR.

The amplicons can also be used in microarray analysis. In some embodiments, the amplicons are used as a substrate for microarray analysis. Amplicons or fragments thereof can be used to prepare single strand oligonucleotides that can be spotted onto a microarray to create a microarray library. In other embodiments, the amplicons or fragments thereof can be used to prepare single stranded oligonucleotides that can be hybridized to a known library.

In preferred embodiments the amplicons are sequenced. Amplicons can be sequenced using any suitable method known in the art. For example, amplicons can be sequenced by Sanger sequencing. In a preferred embodiment, amplicons are sequenced by next-generation sequencing (NGS). In some embodiments, sequencing is used to generate information about the chromatic architecture or methylation status at the genomic or a reduced representative level. In some embodiments, sequence is used to generate differential profiles at the single nucleotide level. Therefore, in some embodiments, the analysis includes identification or one or more nucleotides that alter the profile of a test sample compared to a control or a standard. In some embodiments, the alternated nucleotide(s) is a polymorphism.

In some embodiment, the amplicons are used to prepare a sequencing library and/or are modified in another way to facilitate sequencing or microarray analysis, particularly NGS. In a particular embodiment, the amplicons are modified to include sequencing adaptors for high throughput sequencing. Exemplary adaptors that can be used are well known in the art and include, for example, ILLUMINA® adaptors.

In some embodiments, particularly after fragmentation, the amplicons may require end repair and/or 3'-A addition. Methods of repairing 5' and 3' ends are known in art. Some of the PCR-based methods discussed above include modifying amplicons to include an adaptor that can include PCR primer binding sites, etc. In some embodiments, these sequences are removed prior to sequencing. In a preferred embodiment, this is accomplished using a restriction digestion using a restriction enzyme that cuts at a restriction site incorporated into the amplification adaptor. The removal of amplification adaptor (e.g., primer binding sequences) by a type IIs RE (such as BciVI) can, in some embodiment, generate an overhang A at 3' end and phorphorylation 5' end, which allows a direct ILLUMINA® adapter ligation without end-repair or 3'-A addition. When the product mostly is within appropriate size, the adapter ligation can be applied directly. Adaptors are typically ligated to the ends of the amplicons and used as priming sites and barcodes for sequencing reactions. Multiplexing is also possible. For example, by incorporating different bar codes for different starting material or different assays, large numbers of amplicons from different starting material and/or assays can be amplified and/or sequenced as pool and linked to a specific profile by identifying the bar code during bioinformatics analysis.

In some embodiments, the amplicons are prepared for sequencing with Nextera DNA Sample Prep Kits (ILLUMINA®).

In a specific embodiment, profiles are prepared by a Paired-End Mapping strategy similar to that originally used for CNV detection (Korbel, et al., *Science*, 318:420-426 (2007)). In particular embodiments, DHSR fragments or fragments embedding hyper-methylated DNA stretches are sequenced by paired end sequencing.

Any of the methods disclosed herein can include bioinformatics analysis, computation biology analysis, etc. For example, amplicon sequences identified during microarray analysis or sequencing can be mapped to the test cell type's genome and used to prepare a genomic or reduced representative chromatin or methylation profile. Such analysis can be applied to facilitate pattern recognition, sequence alignment, gene finding, and/or methylome and/or chromatin profile assembly and visualization.

VI. Methods and Fields of Using Chromatin and Methylation Profiles

Chromatin and/or methylation profiles and corresponding sequence information can be used for a variety of applications including diagnostic methods, biomarker analysis, methods of treatment, and research based methods such as drug design and screening, and drug target searching.

Additional assays and analyses can be performed in combination or in parallel with the disclosed methods. Exemplary assays include, but are not limited to open chromatin measured with ATAC-seq, transcriptome analysis by RNA-seq, mutation analysis including SNP analysis, telomere analysis and other functional genomic data and analysis (Buenrostro, et al., *Nature Methods*, 10:1213-1218 (2013), Pan, et al; *PNAS*, 110, 594-599 (2013), Zong, et al., *Science*, 338:1622-6 (2012), Wang, et al., *PNAS*, 110: E1906-1912 (2013), and U.S. Ser. No. 14/139,612, each of which is specifically incorporated by reference herein in its entirety). The combination of such data allows for the identification of the specific elements relevant to the cells and/or disease being investigated.

Profiles can also be used to identify, characterize, or compare between two samples promoters, enhancers, insulators, active and inactive genes, and site of various histone modifications, distribution of DHS, open chromatin, transcribed regions, lamin binding sites, CTCF binding sites etc., as discussed and exemplified in the Examples below.

Profiles also promote an understanding of the nature of reprogramming and/or differentiation, and/or disease development from a new angle and dimension. The profiles can be used to identify new targets, for example S-enhancers for chromatin manipulation, which may be used as the targets for CRISPRi or other methods of gene therapy. In the field of stem cell biology, the manipulations can be used to generate specific long term renewing precursor cells, to quickly identify efficient iPSC clones; etc., which can be used in cell therapies. In disease-related field such as cancer and genetic disease manipulations can be used to convert diseased cells to non-diseased cells, or to convert insensitive cells to cells that are sensitive to conventional therapies.

A. Diagnostic Applications

In some embodiments, profiles are used to diagnose or assist in the diagnosis of a disease or condition. In preferred embodiments test cells obtained from a subject are used to prepare one or more profiles which is compared to a corresponding control or standard profile. For example, the control or standard profile can be prepared from normal control cells (e.g., cells that are known to be non-diseased, and exhibit a normal, healthy, or non-diseased profile). If the profile of the test cells is different from the profile of the control cells, the information can be used to characterize the disease or disorder of the test cells. For example, chromatin architecture and/or methylation status can provide information about gene expression. Therefore, profiles can be used to identify gene that are differentially regulated (up or down) in diseased cells compared to non-diseased cells. Differential chromatin architecture and/or methylation status between test cells and normal control cells can be used to establish markers that are indicative or diagnostic of the disease or condition from which the cell originate.

Accordingly, in some embodiments, the control or standard profile is of cells from a known disease or condition and includes chromatin and/or methylation markers that are indicative of the disease or condition. If the profile of the test cells exhibit one or more of the chromatin and/or methylation markers that are indicative of the disease or condition, the test cells, and therefore the subject from which the cells were obtained, can be determined to have the disease or condition. If the profile of the test cells does not exhibit the chromatin and/or methylation markers that are indicative of the disease or condition, the test cells, and therefore the subject from which the cells were obtained, can be determined to have the disease or condition.

For example, profiles can be used for assessing the fate potential of stem cells, and in other fields of cell biology such as development, differentiation, and aging, for detecting epigenetic defects in cells from amniotic fluid or from dissected preimplantation embryos, for characterizing genetic diseases, or for diagnosing of cancer, example from small numbers of cells such as those that might be obtained from various body fluids.

Large scale screening can be used to investigate the relationship of a test with the control for any particular disease to subtype of disease. For example, screening can provide information about diagnosis for each particular type of diseases or subtypes of diseases. The criteria may be a cause of the disease or just a biomarker or diagnostics marker if the underlying mechanism of the disease is unknown.

The disclosed methods are particularly advantageous because they are very sensitive and can be applied effectively to limited quantities of DNA isolated or accessed from very low quantities or even a single cell. They can detect the differences or characteristic alterations in parameters between health/normal and unhealthy or abnormal phenotypes at a molecular level. Because the methods are compatible with single cell or a very small quantity of cells, they can be used for early detection, diagnosis, prognosis, and/or monitoring of diseases at very early stages (ex. cancer, embryo) using typically non-invasive or minimally invasive technique. In some in some embodiments, only a blood sample is required. For example, the methods can be used to analyze the DNA or cells in the peripheral blood to assist in a cancer diagnosis or to monitor efficacy of treatments such as chemotherapy or isotope therapy. Another preferred application is prenatal detection and/or diagnosis of genetic diseases.

An exemplary method of diagnosing a subject with a cancer can include, for example, (a) preparing a profile of the chromatin architecture of genomic DNA; and/or (b) preparing a profile of the methylation status of genomic DNA; wherein the genomic DNA is isolated from cells obtained from the subject that are suspected of being cancerous; and wherein the subject is diagnosed with cancer if the profile of the chromatin architecture and/or the profile of the methylation status exhibits one or more indicators of cancer.

B. Drug Development and Disease Treatment

Profiles can be used to assist in drug development. For example, chromatin architecture and/or methylation status profiles can be prepared for cells prior to and after treatment with a drug. As discussed above, certain markers with a cell's chromatin architecture and/or methylation status profile can be indicative of a disease or condition. Likewise changes in one or more of the profiles, particular in markers associated with the disease or condition, can be indicative of a drug's efficacy to treat the disease or condition. The methods are conductive to automation and can be utilized in large drug screens. For example, a single drug can be screened over many cell types, many drugs can be screen over a single cell type, or many drugs can be screened over many cell types.

Similarly, analyzing one or more of the profiles prepared from cells obtained from a subject before and again after administration of a drug can be used to determine if the drug is efficacious. For example, in some embodiments a drug is determined to be efficacious when a profile, preferably one or more markers associated with the disease or condition, changes after treatment with the drug. Preferably, the profile (and/or the marker) becomes more closely aligned with a normal or healthy profile and/or less aligned with a diseased profile following treatment with the drug.

Analysis of subject's cells' chromatin architecture and/or methylation status profiles can be used to assist in the selection of drug from treatment. For example, one a subject's chromatin architecture and/or methylation status profile is obtained, a drug can be selected which, following treatment will more closely align the profile with a normal or healthy profile and/or reduce alignment with a diseased profile.

Similar to the diagnostic applications discussed above, the disclosed methods give a very sensitive measurement or detection with a single cell or a very small quantity of cells. This characteristic improves the precision and accuracy of the analysis, particular in cases that the cells of sample are heterogeneous, which is a common case for human cells. Furthermore, the methods have potential applications in research, for example, the identification of new drug targets which may be hidden from discovery using conventionally studies due their heterogeneity in human cells. In addition, the methods offer a way to directly identify DHRS, sites which have not been studied on a genome wide scale due to technical limitations of the conventional technologies.

C. Exemplary Uses

1. Stem Cells

In a particular embodiment, chromatin architecture and/or methylation status profiles can be used to characterize or determine the fate potential of stem cells. Starting with a single stem cell, the progeny cells undergo a series of relatively well defined developmental steps, associated with progressive restriction of the lineage potential of the intermediate precursors. As development proceeds there is a progressive nuclear condensation with appearance of more or less lineage specific patterns of chromatin condensation visible at the light microscopic level. For example, neutrophils develop multi-lobed nuclei with clumps of condensed chromatin in each lobe; erythrocytic nuclei gradually become totally compacted, then expelled; mature lymphocytes show clumps of dark staining chromatin, while retaining round nuclei with open areas; and megakaryocytes develop polyploid nuclei without complete condensation.

In an exemplary assay, chromatin architecture and methylation status profiles of precursor cells are established and compared to differentiating lineages. For example, in a particular embodiment, profiles from myeloid precursors (e.g., CD45RA+ cells) can be compared to erythroid cells (e.g., CD34+ cells differentiated into glycophorin positive erythroblasts by in vitro treatment for 6 days with erythropoietin (EPO)), megakaryocytic cells (e.g., CD34+ cells treated for 6 days with thrombopoietin (TPO)), etc.

2. Tumor Characterization and Cancer Diagnosis

Both heterogeneous somatic mutations and marked changes in the distribution of sites of DNA methylation between normal melanocytes and melanomas are seen and these are functionally significant, reflecting activation and silencing of specific sets of genes. Furthermore, heterogeneity and patterns of evolution of methylation changes in tumor DNA can occur within a single tumor. A large fraction of DNA methylations of regulatory significance tend to occur in clusters along DNA. Therefore, sampling of a fraction of CpG sites across the genome offers an overview of changes in methylation pattern that can be obtained with methods that are less complex than bisulfite sequencing but provide data about CpG island methylation. The disclosed profiling methods can be used for high throughput sequencing and informatics analysis to measure methylation patterns and mutations for single cells as well as for bulk cells in a malignancy and begin to deduce the order in which CpG (de) methylation and mutation changes occurred in the tumors. The methods, particularly the MDA-based MSRE-ligation-WPA methods, are conducive to simultaneously providing DNA for mutation analysis and determination of methylation status of CpG islands from the same single cell.

The mechanisms of cancer evolution and metastatic onset are still largely unknown. Effective characterization of the aggressive potential of tumors at early stages has enormous potential to guide new clinical interventions and translational research. Tumor populations are dynamic aggregates of constantly evolving subclones, each carrying a variety of aberrations including both changes in the primary sequence of DNA and epigenetic changes that alter gene expression. This heterogeneity is often associated with differences in the biological behavior of different cell subpopulations. Some of these subclones are likely to be the primary instigators of invasion, metastasis or relapse following treatment. In certain cancers there is a typical but not obligatory order in which mutations accumulate, and it is conceivable that what matters for progression is the progressive accumulation of changes, rather than their order, as suggested by Fearon and Vogelstein. However, computational approaches indicate a more complex picture that implies that the order may affect the phenotype. Changes in the epigenetic state of cells, and in particular changes in DNA methylation patterns, may also play a role in tumor evolution as important as that of changes in the primary sequence of the tumor DNA.

An evolutionary-based approach may allow inference of a clonal evolutionary tree (rather than a simple linear path) from a single bulk DNA methylation or mutation measurement. Coupling analytical approaches with single cell validation experiments can substantially change the understanding of cancer progression. To evaluate the significance of changes in DNA in tumors it is necessary to consider jointly changes in DNA methylation and DNA sequence (mutation) as these can act jointly to affect the activity of an allelic gene pair or a functional pathway.

There is emerging evidence that mutations occur in a preferential order in some cancers. For example, in a preliminary analysis the BioCarta pathways AGR and ALK, which contain similar numbers of genes, and are co-mutated in many tumors, whereas fewer are mutated in the ALK pathway alone, as opposed to more tumors that are mutated in the AGR pathway. This indicates that the preferred order in which these pathways were mutated in the tumors is that AGR is mutated first, followed by mutations in ALK. Performing single cell experiments of a cell population from a tumor allows for the construction of trees or more complex evolutionary patterns (directed acyclic graphs) which indicate the order in which mutations and methylation modification occur. This type of information can be used to determine the phenotypic consequences of certain mutations and methylation modifications, and can be used to assist in the diagnosis and prognosis of cancer.

The simultaneous analysis of DNA mutation and methylation enables determination if certain pathways or genomic positions of the mutation and methylation interact with each other, and whether the emergence of certain mutations affects the methylation patterns in their neighboring CpG islands. Computationally relevant analysis of public data from the BGI (Xu, et al., *Cell*, 148: 886-895 (2012)) comparing between a bulk measurement and single cell measurements from WES of a kidney tumor (Strino, et al., *Nucleic Acids Research Nucleic Acids Res*, 41(17):e165 (2013)). The data indicates that evolutionary trees inferred from the bulk data identified correctly the majority of co-mutations observed by single cell measurements.

Such analysis can results in the reconstruction of a temporal pattern of emergence of DNA methylation in a cancer, to partially construct the order in which methylated and mutated sites appear in the cell population, and to determine if co-methylations/mutations occur in the same cells.

Because methylation in CGI tends to be associated with gene silencing, if demethylation and pathway activation is selected for in the tumor it might occur at all genes in a pathway and could occur on only one allele of each gene. Silencing of a tumor suppressor gene or pathway by methylation alone or in combination with mutations, might occur in different genes of the same pathway in different cells but would generally affect both alleles. This analysis has the potential to detect new pathways that promote or interfere with tumor progression.

VII. Kits

Kits for use with the methods disclosed herein are also disclosed. The kits for the MDA-based CpG methylation and DHRS methods typically include one or more endonucleases such as DNase I, one or more MSRE, and/or one or more non-MSRE, one or more reagents for lysing cells, optionally intramolecular oligonucleotide ligation, multiple strand displacement amplification, ligation of sequencing adaptors to oligonucleotides, or any combination thereof.

Kits for the PCR-based methods typically include reagents for PCR in addition to or in alternative to reagents for multiple strand displacement amplification.

Reagents can be, for example, buffers, primers, enzymes, dNTPs, carrier RNA, and other active agents and organics that facilitate various steps of the disclosed reactions. The kits can also include instructions for use.

EXAMPLES

Example 1: Analysis of Phi29-Based Amplification Efficiency

Materials and Methods

Escherichia coli K-12 genomic DNA was digested with AseI (ATTAAT), comparing with its intact counterpart genome, subjected to WPA amplification (Pan, et al., *PNAS*, 105(40):15499-504 (2008)), and HiSeq2000 sequencing.

Results

The relative effectiveness of a multiple displacement method of genome amplification referred to as whole-pool amplification (WPA), on DNA of various lengths was determined by quantitation of the sequencing reads of different size fragments from a complete restriction digestion (PsiI, TTATAA (SEQ ID NO:77)), which is indifferent to the methylation status of deoxycytidylic acid) of *E. coli* genomic DNA. The results indicate that overall, when the fragment size is >=4 kb, the amplification efficiency is maximally independent of the size, however, when the fragment is <3.5 kb, the level of amplification is exponentially correlated to the fragment size (FIG. 1A-1D). The amplification efficiencies (basing on RPKM) are correlated to the DNA fragment size defined in the digestion of the *E. coli* genome with AseI (X axis). Y axis: read depth (RPKM); X axis: fragment size. The genome was digested and amplified (cut fragment/AseI digest)) or the corresponding sequences of the intact genome amplified the same way (intact seq./control). The figures illustrate that a sequence (about 1-2 kb) close to an end of a fragment (even if the fragment is very large) will be significantly depleted after multiple displacement amplification.

DNase I digested hypersensitive fragments and methylation sensitive endonucleases (MSRE)-generated fragments in unmethylated CpG islands/shores mostly are <1-2 kb. Furthermore, because the mechanism of amplification requires random primer binding sites upstream of a sequence, there will be a tapering off of the representation of DNA sequences adjacent to the ends of fragments. The precise level of amplification of each fragment could be determined by multiple factors besides fragment size, but no relationship between CG content and WPA efficiency was found.

In the past, problems with amplification of very small amounts of DNA by Phi29 polymerase include the generation of non-specific DNA products in the absence of added template, and the loss of sequence coverage especially when a single cell was used. Such problems were reduced by modifications to discussed in Pan, et al., *PNAS*, 105(40): 15499-504 (2008). One modification is to conduct the amplification in the presence of relatively high concentrations of trehalose. Trehalose also reduces the sequence bias, improving the sequence (locus) coverage. In addition, all reagents can be screened for the presence of traces of potential template DNA before use in the amplification reaction. Nine-mer random primers can used to drive displacement amplification, which may also reduce the bias. The time of amplification can be optimized, since with prolonged amplification times, contaminating products will eventually appear.

Example 2: Whole Genome Scale Blocks of DNA from Condensed Chromatin (DHRS) can be Recovered and Sequenced Materials and Methods DHRS-Based Chromatin Profiling An exemplary DHRS-based method of chromatin profiling is illustrated in FIG. 2. Using the procedure showed in FIG. 2, conditions and methods were originally tested with aliquots of 100 cells each from a single growth of K562 cells in each test, and afterwards it was scaled down to single cells. Aliquots that were snap-frozen and stored at −80 C were also be tested. A procedure that were scaled down directly onto samples of ~100 cells or less included using the nuclei isolated by cell lysis in 0.1% non-ionic detergent IGEPAL CA-630. The nuclei were recovered by centrifugation (Crawford, et al, *PNAS*, 101:992-997 (2004)), and were then directly processed for DHRS. The nuclei were then treated with a freshly diluted pancreatic DNase I (the concentration and reaction duration can be optimized, as can all steps below). The reaction was stopped by the addition of EDTA. After participation, the mixture was treated with NaOH (pH14) to denature DNA and proteins, and to remove associated proteins from DNA, which was followed by neutralization with TrisHCl, pH7.4. Phi29 DNA polymerase with trehalose and other components (pre-mixed) were then added to initiate amplification at 30 C for 12 hours (Pan, et al., *PNAS*, 105(40):15499-504 (2008)). This produces high molecular weight amplified DNA (about 12-kb).

To reduce the complexity of the DNA pool for library construction and sequencing, the amplicons were randomly sheared by sonication and approximately 3-kb products are selected. A Paired-End Mapping strategy similar to that originally used for CNV detection (Korbel, et al., *Science*, 318:420-426 (2007)) was applied. This Paired-End Mapping strategy is an optional step. The complexity is significantly reduced when the genome is treated with DNaseI or other processes that distinguish the highly open chromatins and the highly compact chromatins. Before sonication (after amplification) results were analyzed by qPCR for each of the known hypersensitive sites and DNase I resistant regions. The library was subjected to Illumina sequencing by standard procedures.

Sample Processing and Sequencing $5 \times 10^6$ cells were subjected to a DNase I protocol (Crawford, et al., *Genome Research*, 16:123-131 (2006), Crawford, et al., *PNAS*, 101:992-997 (2004)), followed by protease K digestion, phenol-chloroform purification and ethanol precipitation of DNA. Variants of aliquots corresponding to approximately one hundred cells-equivalent of DNA were used for amplification. The amplicon was treated for reduced representative library construction and sequencing. Each sample from the experiments was sequenced to a depth of >50 million reads per sample.

FIG. 2 is a diagram showing an exemplary assay. A nucleus (chromatin) was digested with DNase I. The short DNA fragments were depleted while the long fragments/sites (DHRS) were selectively amplified with WPA. The amplicon was then treated as bulk genomic DNA with a paired-end mapping protocol (Korbel, et al., *Science*, 318: 420-426 (2007)) to reduce the sequencing depth required for genome-wide coverage/mapping of the DHRS sequences. The read-mapping gaps of high throughput sequencing represent the sequences with frequent and favorable DNase I access while the read-mapping peaks represent DHRS.

Results

A method for recovering and sequencing blocks of DNA from condensed chromatin (DHRS) at a whole genome scale of a small number of cells and single cells was developed, and illustrated in FIG. 2. Nuclei from isolated cells were treated and DNase I which cut the genome at hypersensitive sites to yield small fragments corresponding to DHS and larger fragments corresponding to DHRS. A Phi29-based amplification (WPA) was carried out to selectively amplify the larger fragments. Amplified fragments were sheared and size selected. The ends of the size-selected fragments were biotinylated and subjected to intramolecular ligation leading to circularized fragment joined at the biotinylated ends. Circularized fragments were sheared and biotin-fragments were recovered. The fragments were used to make a library, sequenced (NGX) and mapped, yielding a DHRS profile.

The results show a depletion of reads around transcriptional start sites for actively transcribed genes, but not for silent genes. With 50 thousand fold less cells, a similar enrichment of DNase I resistant site is detected using the DHRS-based method compared to a conventional DHS-based method (FIGS. 3A-3B).

Figure 5:
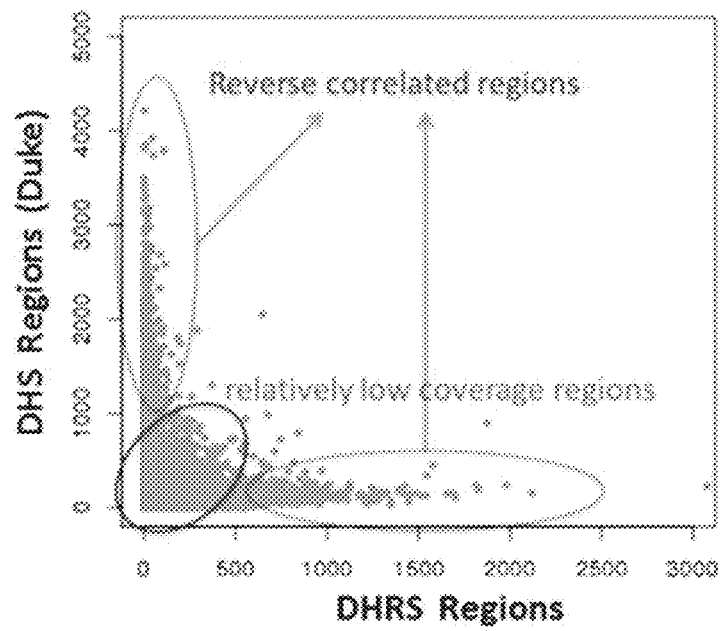
FIG. 5 is a scatter plot showing the distribution of DHS regions versus DHRS regions. The X-axis is experimental DHRS sequencing data, and the Y-axis is DHS data from the UCSC ENCODE database.
Figure 6:
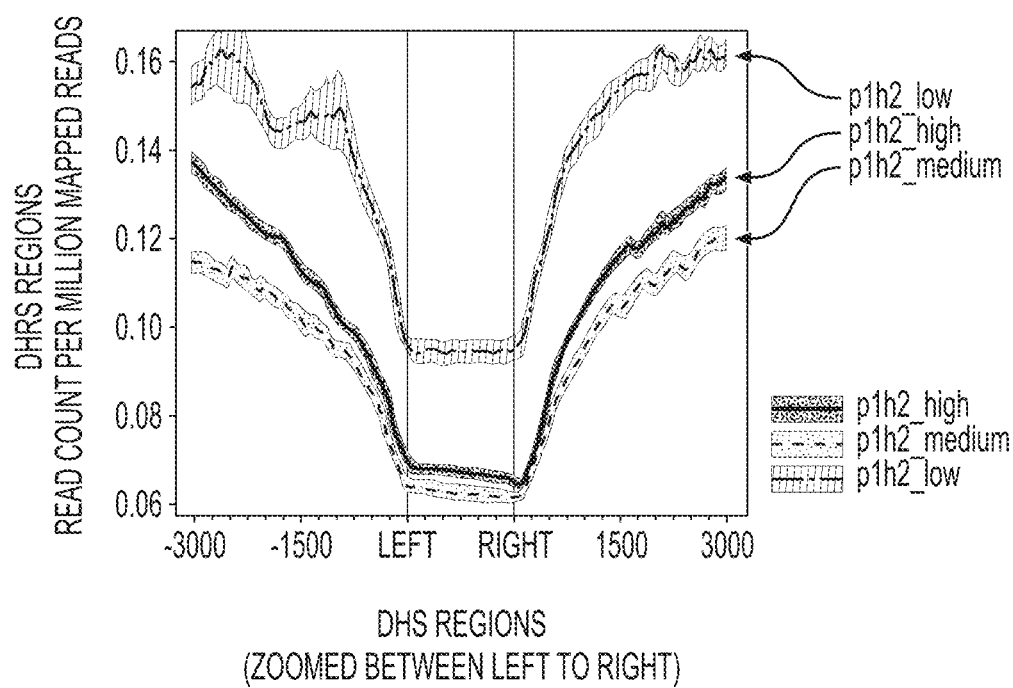
FIG. 6 is a plot showing DHRS regions (read count per million mapped reads) relative to the locations of known DHS regions. The X-axis is DHS data from the UCSC ENCODE database, and the Y-axis is DHRS sequencing data. This is a result derived from a K562 sample with 100-cells (labeled as p1h2). Low, Medium and High represent the relative expression level of the associated genes of the chromatin.

The results obtained by the DHRS-based method showed depletion of active chromatin regions, but the DHS measurements obtained by conventional procedures (ENCODE data) showed incomplete agreement (FIGS. 4-6).

FIG. 5 is a scatter plot showing the distribution of DHS regions versus DHRS regions. The X-axis is the DHRS sequencing data, and the Y-axis is DHS data from the UCSC ENCODE database. The figure shows that indeed a separate group of fragments (DNA sequences) are classified as either DHAS or DHRS, and these 2 groups are fragment are exactly reversed correlated to each other (DHS or DHRS). However, a big part of the chromatins detected as a low signal in bother DHS and DHRS. In other words, only a very small portion of the DHS sequences with very low signal are of DHRS, and only a very small portion of the DHRS sequences with of DHS. Additionally, most sequences (chromatins) are classified by neither DHS nor DHRS site, indicating that it is different to obtain the DHRS message from DHS message—it is not true to assume that the chromatins are either DHS or DHRS. Therefore, one is not necessarily able to extract DHRS sequences from DHS analysis alone. This also indicates that additional biological significance can be obtained by DHRS analysis compared with DHS.

FIG. 6 is a plot showing DHRS regions (read count per million mapped reads) relative to the locations of known DHS regions. The X-axis is DHS data from the UCSC ENCODE database, and the Y-axis is DHRS sequencing data. This is a result derived from a K562 sample with 100-cells (labeled as p1h2). Low, Medium and High represent the relative expression level of the associated genes of the chromatin. The figure demonstrates that the center of the DHS peaks overall are the valley of the DHRS. Collectively, FIG. 5 illustrate that a part of the chromatin are not covered by either DHS or DHRS, and those covered by the detection of DHS and DHRS are reversely correlated. However, a big part of the chromatins were detected as a low signal in both DHS and DHRS. In other words, only a very small portion of the DHS sequences with very low signal are of DHRS, and only a very small portion of the DHRS sequences are of DHS. Therefore DHS analysis alone is not able to extract DHRS sequences. These results also indicate that additional biological significance can be obtained by DHRS analysis compared with DHS.

Figure 9:
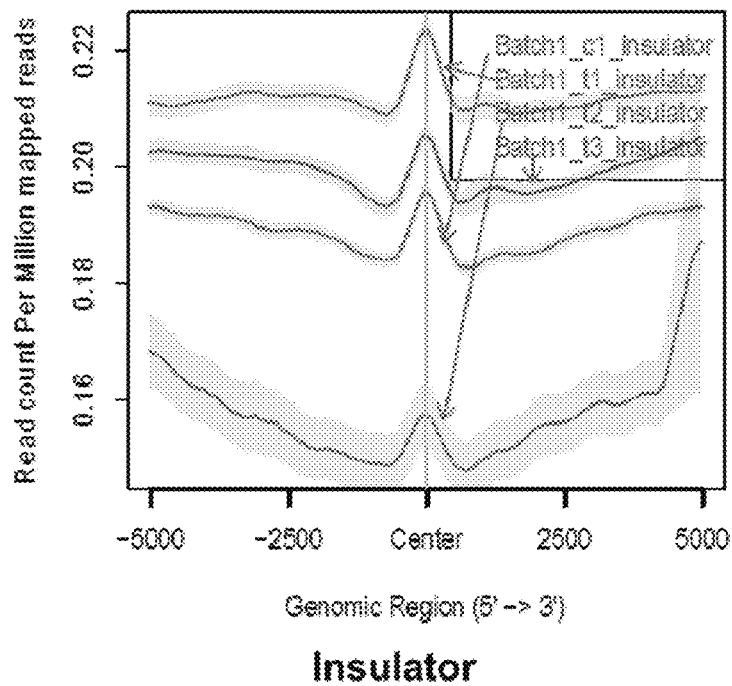
FIG. 9 is a plot showing DHRS regions (read count per million mapped reads) relative to the location of four known insulators. c1, t1, t2, and t3 refer to different samples.
Figure 10:
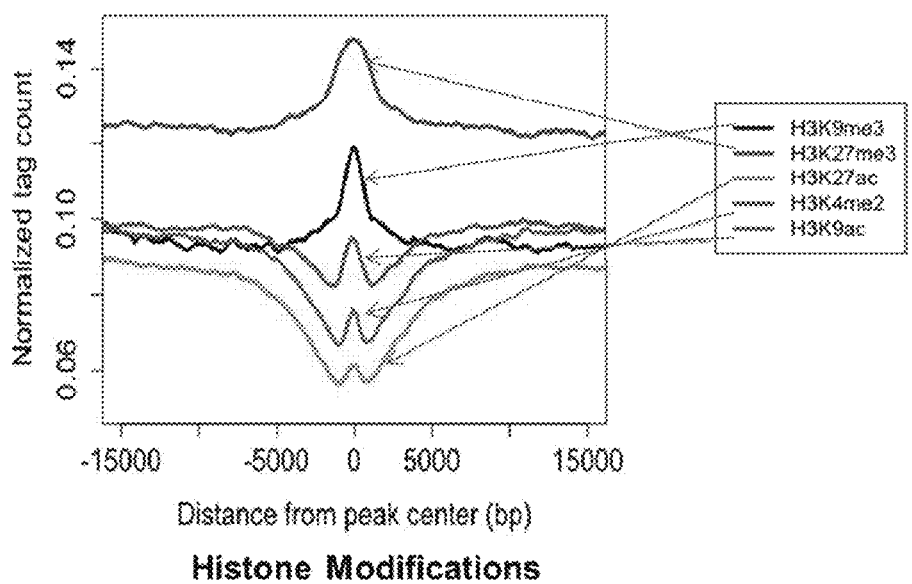
FIG. 10 is a plot showing DHRS regions (read count per million mapped reads) relative to the location of five known histone modifications (H3K9me3, H3K27me3, H3K27ac, H3K27ac, H3K4me2, and H3K9ac).

Additional data correlations between the DHRS-based method and publically chromatin data collected using conventional DHS-based methods are illustrated in FIGS. 7-10. FIG. 7A compared to 7B-7C show DHRS and DHS regions, respectively, mapped to the transcriptional start site of known genes with known expressive levels; FIG. 8A compared to 8B-8C show DHRS and DHS regions, respectively, mapped to known enhancers with known activities; and FIG. 9 shows DHRS regions relative to the location of four known insulators. FIG. 10 shows that DNase I resistant tags were increased over regions with trimethylated lysine 9 of histone 3 (H3K9me3) or H3K27me3, and depleted in regions with acetylation of the same residue (H3K27ac), and also depleted with H3K4me2 (an enhancer mark) and H3K9ac.

Example 3: MDA-Based CpG Methylation Analysis (MSRE-MDA)

Materials and Methods

FIG. 11 is a diagram showing an exemplary method of CpG methylation pattern scanning (CpGMp). The Test DNA (purified or directed extracted from intact cell) was digested, except for MC, with MSRE (1st set of REs). Both were amplified by MDA (e.g., WPA). The amplicon was then digested with the 2nd set of RE (e.g, BstUI) to enrich CpG-rich DNA sequences (CpG islands and shores) for library construction and efficient sequence coverage even with reduced sequencing depth.

MC represents Methylation Control, which is not cut so as to demonstrate all potential DMRs (Differentially Methylated Regions). GUC (General Unmethylated Control) is a control with bulk DNA from the same type of cells to show the unmethylated DMRs in the cell population. Me is methylated DMR; U-Me is unmethylated DMR. The MSRE (1st set of RE) applied to digest the original gDNA is to distinguish Me-DMRs as long and intact fragments, which are amplified efficiently, from Um-DMRs, which are frequently cut to be short fragments, and depleted during MDA (WPA) amplification. The bars represent the original gDNA, and the amplicon.

After sequencing, comparing with MC, the DMR with significant reads in test are called as Me (methylated DMR), and the DMR without reads in the tests are called as U-Me (unmethylated DMR). Overall most U-Me DMRs should be included in the Un-Me list of the GUC.

Restriction digestion was carried out with EagI (CG-GCCG (SEQ ID NO:2))+NaeI (GCCGGC (SEQ ID NO:4))+BssHII (GCGCGC (SEQ ID NO:1))+SacII (CCGCGG (SEQ ID NO:8)), which when combined together cover almost all of the CpG islands plus CpG shores while rarely digesting other CpG-poor sequences. This was used for the $1^{st}$ MSRE cut (FIG. 11).

Results

Figure 12:
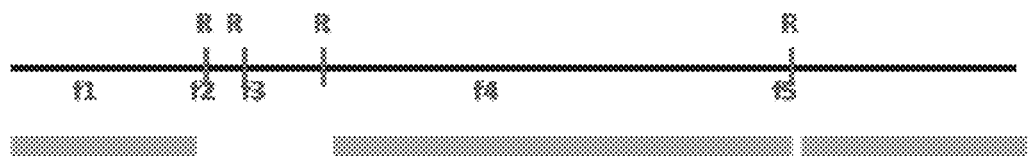
FIG. 12 is a drawing further illustrating the principles of an exemplary MSRE-MDA method. Following restriction digestion with a methylation sensitive restriction endonuclease (MSRE, corresponding to the $1^{st}$ RE cut in FIG. 11), fragments f2 and f3 are too short to be amplified (<2 kb, or <<4 kb) by MDA amplification and form a gap in the signal map during analysis of the resulting amplicon. f1, f4, f5 are long enough to be amplified efficiently.

FIG. 12 is a diagram showing an exemplary method of CpG methylation pattern scanning (CpGMp), adapting a similar WPA selective amplification principle as discussed above for chromatin profiling, for detection of methylation at restriction sites for specific MSREs. The fully methylated DNA stretch will be intact (long) and will be amplified efficiently, while the DNA stretches with nucleotides frequently de-methyated will be cut by one or a combination of a few MSREs (generally the mixture of MSRE cuts every CGI more than 2 times, but rarely in non-CGI sequences), and will be depleted after the WPA step. Generally, in order to process low numbers of cells, complete removal of the DNA-bound proteins is preferred to ensure complete accessibility and digestion of the dsDNA by the MSRE. Generally, for low starting cell numbers, naked DNA should not be conventionally purified to avoid DNA shearing, denaturation or loss. The amplified DNA then can be fragmented and sequenced by paired end sequencing so as to determine the fragments embedding hyper-methylated DNA stretches.

The data presented in FIG. 18A-18B was prepared according the method described in the materials and methods above, and shows that the method detects CpG methylation patterns for low numbers of cells and single cells. Briefly, in a particular protocol (FIG. 11), intact cells with their gDNA in-tube extracted, and digested by the combination of the 4 MSREs, followed by WPA, and the amplicons were then further treated with BstUI for CGI sequenced enrichment and library construction for Illumina sequencing. FIG. 18A is a sequencing signal displayed using IGB (Affymetrix Integrate Genome Browser) and shows methylated (Me) DMR and unmethylated (U-Me) DMR for K562 and Yumac (melanoma) cells. GUC and MC are the same as FIG. 12. Test reads are indicated by starting cell number (e.g., 100-cell, 500-cell, 1-cell). Line on the bottom ("CGI") indicates CpG island. "2nd RE" and "MSRE" are the in-silicon cut sites for BstUI and the 4 REs. The 4 panels from left to right show 4 representative loci. MC for all 4 loci show significant reads, which means that all the 4 loci are experimentally detectable. Taking the 2nd locus from left as an example: it is theoretically covered by this analysis procedure because the MSRE and $2^{nd}$ RE cut the locus/CpG island frequently in-silicon analysis of human genome; it is U-Me locus in the 2 samples (500-cells and 100-cells) of Yumac because these 2 samples do not show reads, which is doubly confirmed in the Yumac-GUC that does show significant reads. The locus for 1-cell K562 is called as Me-DMR because it shows significant signal in the sample FIG. 18B shows an analysis of K562 cells showing the relationship of 1-cell, 10-cell, and 100-cell results. 93.6% of 1-cell Me-DMR calls are shared by both 10-cell and 100-cell samples; 97.0% of 10-cell K562 Me-DMR calls are shared by 100-cell sample; 93.3% of 100-cell Me-DMR calls are shared by the 10-cell sample. This indicates that once a locus is detected as Me-DMR in a lower-number-cell sample, it is also detected as Me-DMR in the higher-number-cell sample of the same type, although some loci may be missed for lower-number-cell-sample.

It was empirically determined that if the DNA is significantly randomly sheared or becomes single stranded, the output sequencing reads will not have satisfactory sequence coverage because short DNA will be lost or depleted, and single strands may not be cut even when the DNA sequence is unmethylated. To avoid a "single tube procedure" and minimized treatment before WPA, can be employed, avoiding conventional purification of naked DNA. Diluted guanidine hydrochloride (GuHCl) from the original 4M can be used to denature the DNA-bound proteins and other proteins of a cell. At an appropriate dilution (20 times to 200-times), the low concentration of GuHCl does not interfere with the complete digestion of the genomic DNA by a high concentration of RE. Alternatively, a protease from Qiagen (QIAGEN PROTEASE) may also be effective to digest the nuclear proteins. This enzyme shows sufficient activity with a low concentration of non-ionic detergents that do not interfere with the downstream enzymatic reactions, and can be efficiently deactivated by moderate heating (70° C. for 15 minutes) without melting DNA.

To reduce the cost of sequencing, the CpG islands (and other CpG-rich DNA stretches or CpG shores) sequences can be enriched by digestion of the amplicons with another restriction enzyme (e.g., BstUI (CGCG)). This digestion product gives a blunt, phosphorylated end, which affords an additional advantage in that an end-blunting step prior to adding sequencing adaptors can be omitted. The end-blunting step could contaminate the analysis with non-specifically sheared short fragments. After A-tailing, the sequencing adapter can be ligated and the shorter DNA fragments (such as 45-400 bp) can be recovered. These will enrich the sequences from CpG islands and CpG shores. Other CG rich 4-nucleotides-recognizing RE may be separately applied with different aliquots of the same amplicon to further improve the coverage of the desired CpG rich sequences. In addition to BstUI, other CG-rich 4-nucleotides REs (such as AciI, HinpiI etc) may also be used separately for different aliquots of the same amplicon. Overall, multiple RE digestions are used in combination for the same sample, the coverage of CGI will be significantly improved.

An optional procedure for better enrichment of HpaII-containing fragments from the amplicon can include use of HpaII methylate to methylate CpG sequences at HpaII sites. The treated amplicon can then be sonicated, and captured with MBD to enrich the fragments containing methylated HpaII sites. The treated amplicon can also be captured with a commercial DNA binding protein (MethylCollector™ Ultra, from Activemotif), which binds to DNA fragments with higher affinity with more methylated CpG sites.

Figure 15:
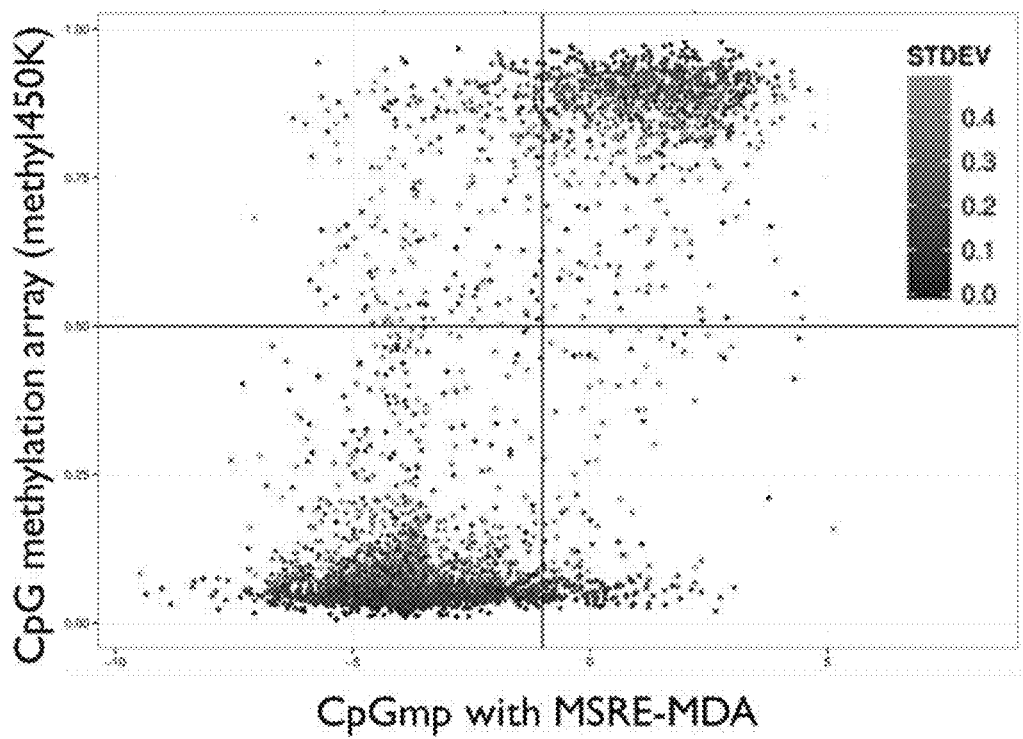
FIG. 15 is a plot showing the correlation of MSRE-MDA with a conventional microarray method Methyl 450K Bead Arrays from ENCODE for cell line K562. Both methods show a high correlation in terms of methylated CpG islands (up-right phase) and un-methylated CpG islands (down-left phase).

FIG. 15 shows the MSRE-MDA result of 100-cells comparison with a conventional result with Methyl 450K Bead Arrays from ENCODE for the same cell line K562. MSRE-MDA result shows a very high correlation with the Methyl 450K data in terms of methylated CpG islands (up-right phase) and un-methylated CpG islands (down-left phase).

Example 4: MDA-Based CpG Methylation Analysis (MSRE-Ligation-MDA or ML-MDA)

Materials and Methods

Figure 14:
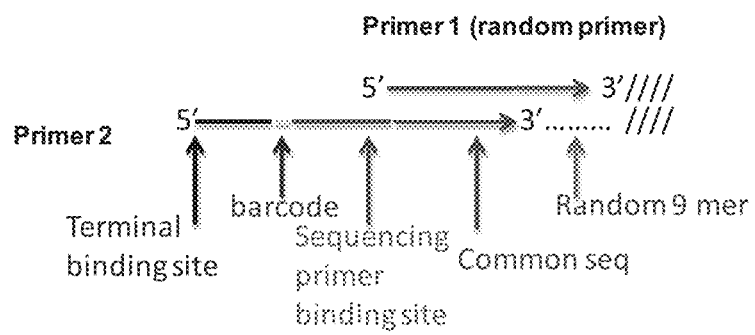
FIG. 14 is a diagram for exemplary primers that can be used to directly, without end repair or ligation, generate a fully-representative library for the whole genome. //// represents the target insert. Primer 1 is used for MDA, and can contain a 3' random 9-mer and a 5' common region that can be used as a binding site for a PCR primer. The PCR primer (primer 2) can include a sequence that binds to the common sequence of MDA primer (primer 1), and optionally a sequencing primer binding site, optionally a bar code, and optionally a terminal binding site. The sequencing primer binding site and terminal binding site are two sequencing tags that can include sequences used as binding sites for sequencing primers. This design allows the amplicon to be used directly as a substrate for high through put sequencing, without an additional library construction step, and to be sequenced in a multiplex fashion, in either direction while "reading" the bar code.

An exemplary ML-MDA method is diagramed in FIG. 13, and an optional smart design of oligonucleotide adapters/primers for multiplex sequencing is further illustrated in FIG. 14. Unmethylated sites and methylated site are distinguished from each other. With MSRE digestion, unmethylated sites are cut and the cut sites are re-ligated from originally non-continuous sequences, which is mostly internal circularization, but some may be ligated to DNA fragment from elsewhere of the genome. With MSRE digestion, methylated sites are retained as their original sequence order as in the gDNA. With sequencing reads, bioinformatics can elucidate if the sites are cut or not cut, i.e. the original sequences are methylated or unmethylated.

Results

The ML-MDA was applied to K562 samples with a low number of cells: each of the four samples composed of approximately 1000-intact cells of K562.

An exemplary PCR result illustrated the strategy of MSRE digestion-ligation-MDA amplification (ML-MDA). ML-MDA was applied to K562 samples with a low number of cells. Each of the four samples is composed of approximately 1000-intact cells of K562. Following the CpGMp strategy above, two test aliquots were digested with MSRE (HpaII), while two control aliquots were not digested with any enzyme, all followed by WPA. Amplicons were about 12 kb. The primer sets CGP4, P7, P8, P9, and P10 derived from previously known methylated sequences each flanking a HpaII site (so MSRE would not cut it off), and primer sets CGN1 and N2 from previously known unmethylated sequences each flanking a HpaII site were used for analysis.

Amplicons were PCR amplified and the results analyzed by gel electrophoresis. The presence of a band indicates that the sequence flanking the HpaII site in the amplicon remains the same as the original order in the gDNA (so the flanking PCR primers amplified it positively), while no-band indicates that the original order in gDNA does not exist anymore, i.e. it was cut off and re-ligated in other direction. CGN1 and N2 in the tests show no band because these 2 sites were unmethylated and cut off with MSRE. All other test and control samples showed bands with one exception. CGP10 in (test sample #2) did not show a significant band.

The advantages of the ML-MDA method include that using these sequencing reads, one can simultaneously analyze any possible mutation with the same set of sequences that is analyzed for CpG methylation pattern. If the mutation occurs in the HapII site (CCGG), the site will not be cut with HpaII even if the C nucleotide in the CpG is not mutated and unmethylated. This can be easily identified by inspection of the reads.

DNA enriched with exome capture from another aliquot of the same amplified DNA can be analyzed for possible nucleotide mutations. Alternatively, after the initial WPA amplification specific primer pairs can be used to further amplify the amplicons using polymerase chain reaction and to analyze them for known or unknown mutations and/or differential CpG methylation status.

Figure 16A:
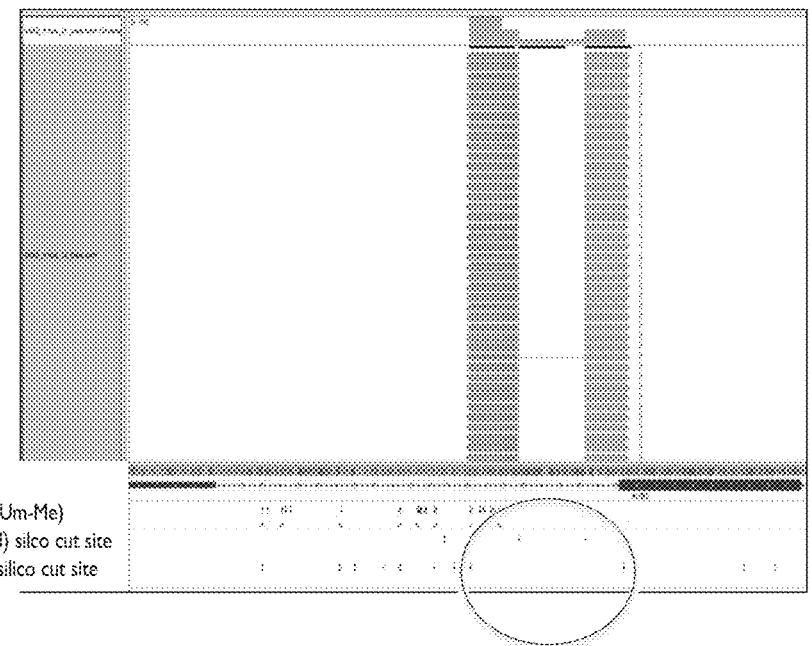
FIG. 16A is a screen shot for a result illustrating a ML-MDA strategy. The circled region indicates that when the DMR is un-methylated (evidenced by the publically available ENCODE data: RRBS data), the $1^{st}$ RE, i.e. MSRE (in this case HpaII) did digest the DNA, and the DNA fragment was circularized, and the two HpaII sites of the fragment were ligated together. After MDA and subsequent BstUI digestion, the HpaII generated and re-circularized fragment was cut off by the 2 BstUI sites. Now with the BstUI fragment, the original HpaII site and its flanking sequences in the fragment are in the reverse of its original direction. The left hand and right hand sequencing reads show the direction and the location of the reads, and shows that the DMR was originally unmethylated. BstUI cuts CGCG sites and will introduce relatively frequent cut sites at DMRs. In this case, two cut sites BstUI sites are flanked by two HpaII sites (CCGG, in the original sequence as shown in the plot). Because HpaII sites were cut, and re-circularized before MDA, the sequence order of the HpaII sites and BstUI sites were reorganized. In addition, the BstUI cut fragment was with an appropriate size range for the sequencing library construction, and so the BstUI fragment flanked by the HpaII sites was sequenced. One HpaII site was within a sequencing read (the read arrows), so the orientation of the religation can be determined. The other original HpaII site was out of the sequencing reads, but the order can be determined and it can be confirmed that the original sequences at the HpaII site was unmethylated, cut and re-circularized.
Figure 16B:
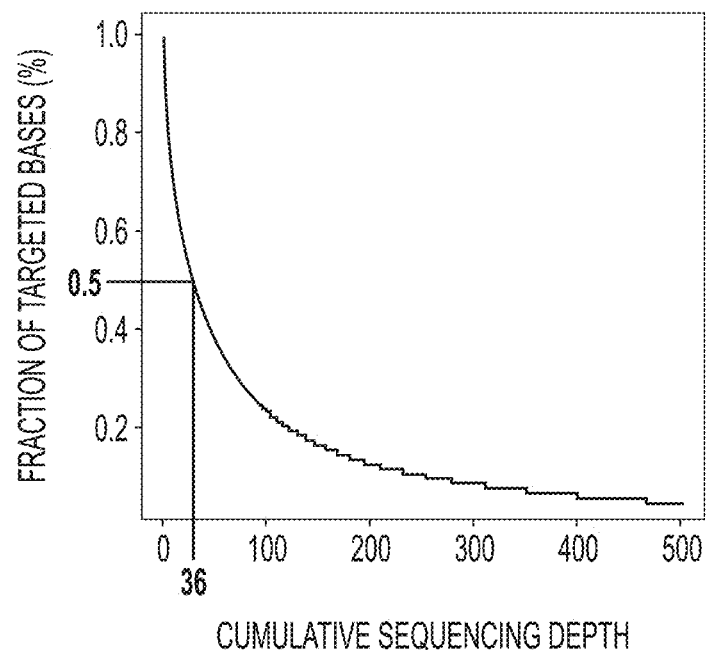
FIG. 16B shows a mapping result of the WES data with an aliquot of the ML-MDA amplicon. An 89% target coverage was obtained with >1× coverage, and a 50% target coverage was obtained with >36× coverage.

One representative sequencing result is shown on FIG. 16A. FIG. 16B shows a mapping result of the WES data with an aliquot of the ML-MDA amplicon. An 89% target coverage was obtained with >1× coverage, and a 50% target coverage was obtained with >36× coverage. These results confirmed that the ML-MDA in principle works well for both CpG methylation and exome-seq with the same sample.

Example 5: PCR-Based CpG Methylation Analysis

Materials and Methods

Figure 17A:
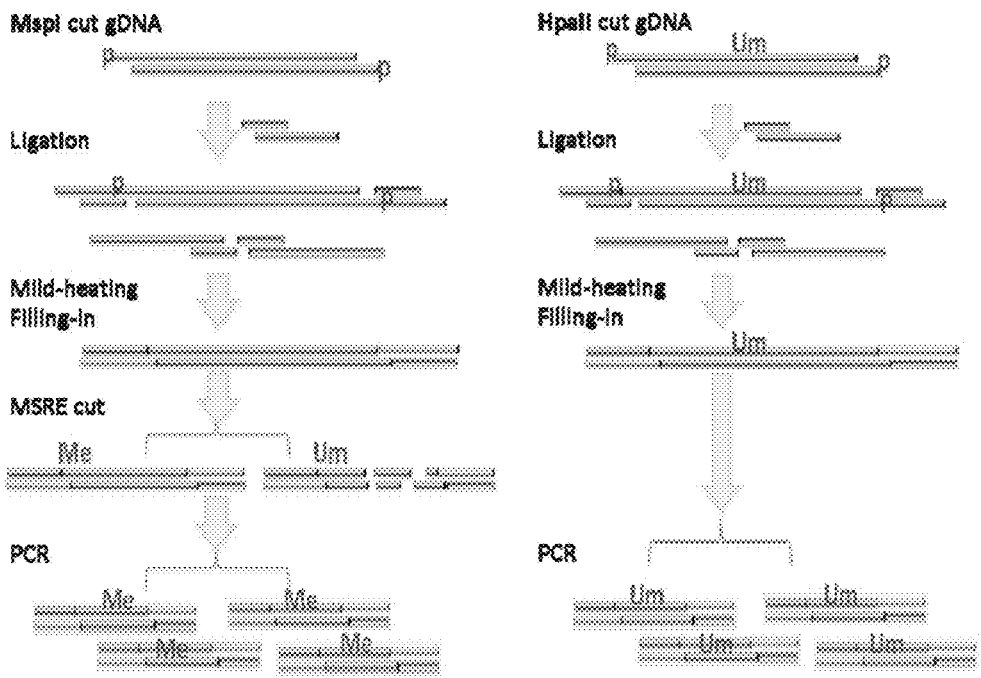
FIG. 17A is a diagram illustrating an exemplary Fragmentation-Adapter/ligation-MSRE/digestion-PCR amplification (FAM-PCR, corresponding to Me-Seq and directly identification of Me-DMRs) method for isolating and amplifying methylated DMRs (left panel), and an exemplary MSRE/digestion-Adapter/ligation-PCR amplification (MA-PCR, corresponding to Um-Seq. and directly identification of Um-DMRs) method for amplifying unmethylated DMRs (right panel).
Figure 20:
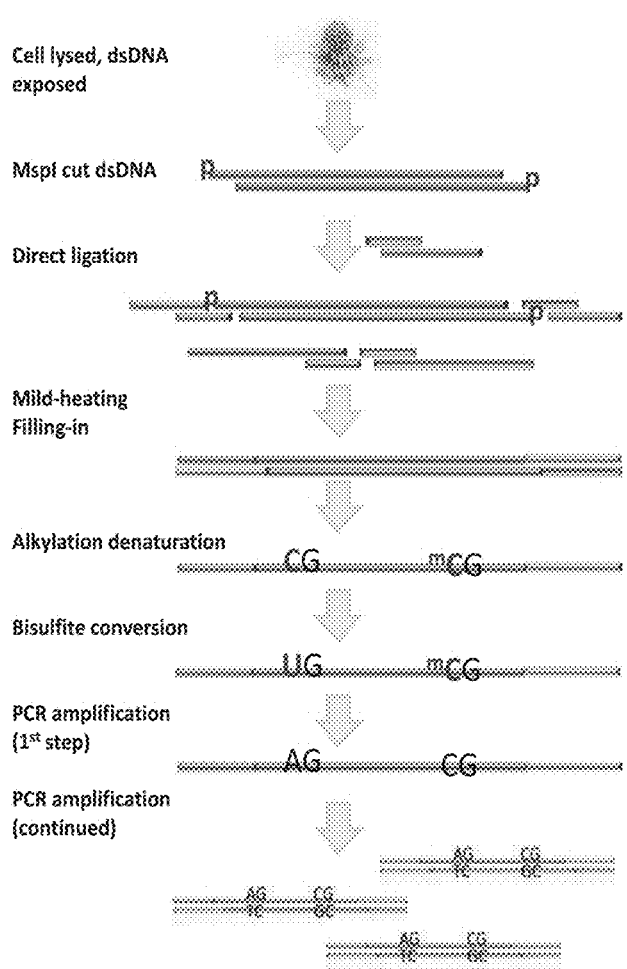
FIG. 20 shows an exemplary method for sensitive, reduced representative bisulfite sequencing (usRRBS). An intact cell pellet or single cell is lysed with a lysis buffer that enables the dsDNA to be efficiently exposed but is mild enough for the subsequent reaction(s). The dsDNA is digested with MspI or another non-MSRE restriction endonuclease (RE) that cuts CpG islands. The resulting fragments can be ligated, without end repair, to an adapter, followed by adapter filing, bisulfite treatment and PCR amplification.
Figure 21:
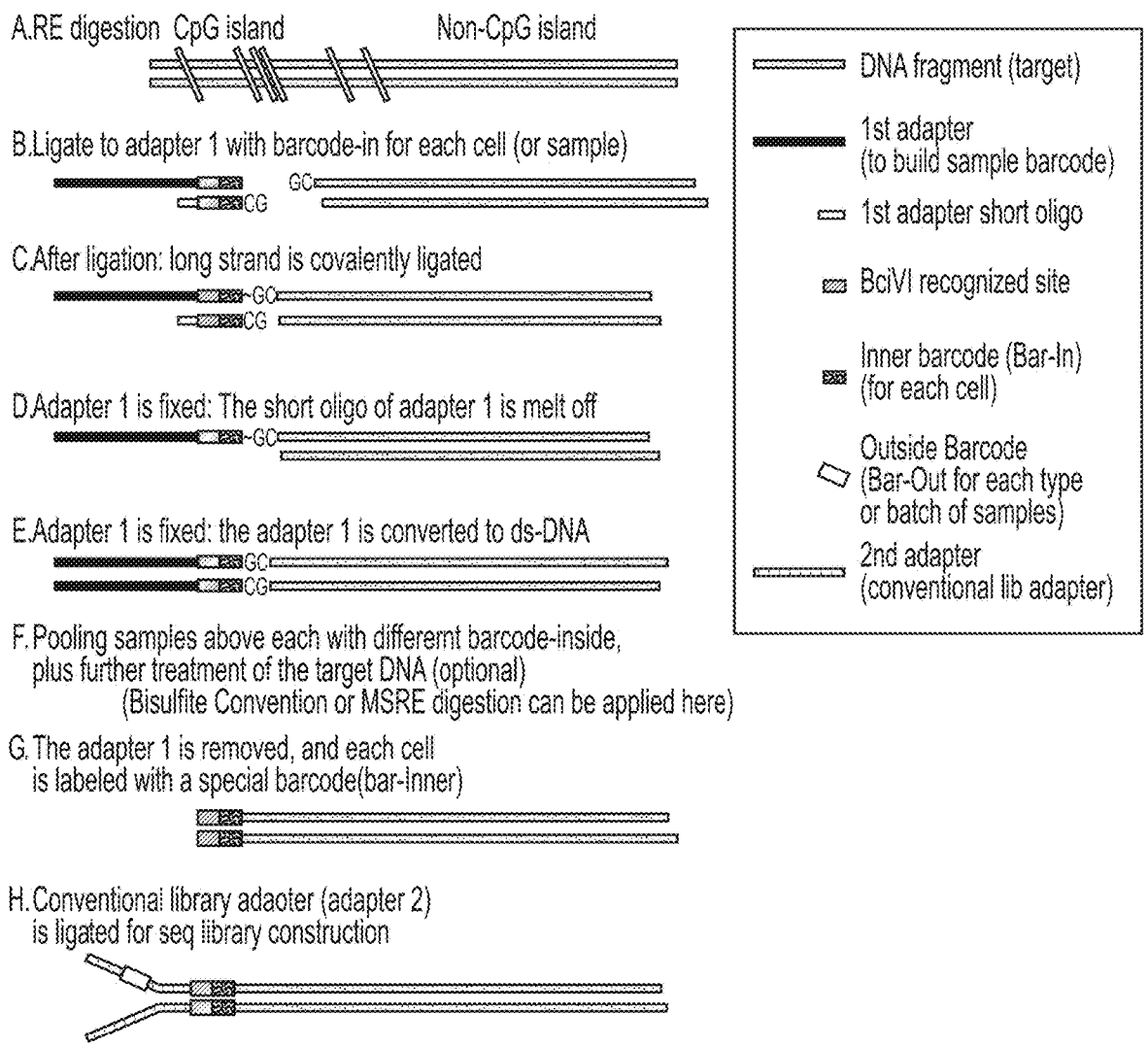
FIG. 21 is a diagram showing the principle of the multiplex adapter design, and the process of using the adapter for high through measurement of multiplex samples. Regarding the adapter E, when FAM-PCR or MA-PCR is applied, a set of conventional (no methylated) or methylated nucleotides (dATP, dTTP, dCTP, dGTP) can be applied for the adapter-filling-in; when usRRBS is applied, a set of methylated nucleotides (dATP, dTTP, d$^m$CTP, dGTP) must be applied for the adapter-filling-in. The step F is an optional process. For the FAM-PCR strategy, an MSRE digestion is applied; for MA-PCR, no process is required; for usRRBS, a bisulfite conversion is applied. After the step F, the samples can be combined/pooled together like one sample for the downstream processes. One set of adapter 1 is given here for their adapter sequences, the bold, underlined nucleotide combination is the barcode (one barcode, b2, is shown as an example). Long-ad1-b2 (with all C methylated as mC): 5'-GAT GCT GTA AAG TTG AAG TAG GTA TCC GTG AGT ACATC\*G-3' (SEQ ID NO:23) (wherein the * is phosphothiate modification for the last nucleotide) Short-ad1-b2 (no mC): 5' CG CGATGTA CTCACGGAT-3' (SEQ ID NO:24). The CG is corresponding to the cohesive end generated with MspI or TaqI or HpaII.

Exemplary methods for PCR-based CpG methylation pattern analysis are diagramed in FIGS. 17A and 17B. A method for identifying methylation loci ("Me-seq") is illustrated in the left panel, and a method for identifying unmethylated loci ("Um-seq") is illustrated in the right panel. For a very small number of cells especially a single cell, the sample can be only analyzed with either Me-seq or Un-Me-Seq. And correspondingly, the Methylated (Me) or Unmethylated (Ume) sequences (both are in form of DMRs) are identified. Combined with separate identification of the total cDMRs with a pool of the same type of samples (in principle the same cell type or of the same genome, but with more cells), the counterpart of CpG methylation DMRs (ex. Um-DMRs vs. Me-DMRs) can be extracted. This system is conductive to a binary (bimodality) analysis. In a population, it is also possible to classify a category as Me/Um (heterogeneity). The assay is preferably carried out in using a single tube procedure before amplification for a good coverage and reproducibility.

Briefly, to collect the data described below, the gDNA was in-tube extracted from intact cells of K562 cell line. For FAM-PCR method, the DNA was digested by MspI, and ligated to the adapter with their cohesive end (only the 3' end of the full length adapter is covalently ligated to the 5' end of the DNA fragment generated with MspI), melted-off the short oligonucleotide, and filled-in the adapters (replacing the melt off short oligonucleotide) to be a double strand. Then the MSREs were applied to cut off the un-methylated DNA constructs. Then the methylated DNA fragment constructs, of which both ends were flanked with adapter sequence, were amplified by PCR. The amplicon were finally size-selected and sequenced.

For MA-PCR method, the procedure is similar except 2 differences. Firstly, the 1$^{st}$ digestion was with HpaII (or other MSRE 4-nucleotides, CG-rich recognizing tag, preferably HinP1I, BstUI, AciI). Secondly, after adapter ligation and filling-in, no MSRE cut was applied by directly subject to PCR.

Results

A set of results are shown in FIG. 19A-19C, shows an analysis of sequencing data with FAM-PCR (Me-Seq) and MA-PCR (for Um-Seq) methods. FIG. 19A shows that the Me-Seq result is consistent with ENCODE RRBS data for the same cell line K562, ex. a higher % of Me-DMR calls is obtained with the RRBS identified Me-DMRs, and it is understandable that inconsistent call are the nature when analyzed the CpG methylation patterns with different methods (conventional RRBS and this FLA-PCR) based on different assumption. FIG. 19B is a summary of Un-Seq (MA-PCR) call, which is consistent with the picture that we know for this type of cells: Um-DMRs occupy a bigger portion of all cDMRs, while Me-DMRs are much less. FIG. 19C, basing on Um-Seq (FAM-PCR), demonstrates the bimodality of the PCR-based CpG methylation pattern analysis.

In summary, the PCR evaluation and sequencing result confirmed that both methods (FAM-PCR or Me-seq, and MA-PCR or Um-seq) work well. In addition, both methods achieved a mapping rate (60-80%) and good coverage. MA-PCR shows better coverage. For example, with 1000-cells, MA-PCR achieved >96% coverage for CpG islands, probably due to its simpler procedure than FAM-PCR method.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 77

<210> SEQ ID NO 1
<211> LENGTH: 6
<212> TYPE: DNA
```

```
<213> ORGANISM: Artificial Sequence
<220> FEATURE:
<223> OTHER INFORMATION: synthetic polynucleotide

<400> SEQUENCE: 1 gcgcgc                                                                     6

<210> SEQ ID NO 2
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 2 cggccg                                                                     6

<210> SEQ ID NO 3
<211> LENGTH: 8
<212> TYPE: DNA
<213> ORGANISM: Artificial Sequence
<220> FEATURE:
<223> OTHER INFORMATION: synthetic polynucleotide

<400> SEQUENCE: 3 ggccggcc                                                                   8

<210> SEQ ID NO 4
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 4 gccggc                                                                     6

<210> SEQ ID NO 5
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 5 ggcgcc                                                                     6

<210> SEQ ID NO 6
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 6 gccggc                                                                     6

<210> SEQ ID NO 7
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 7 gggccc                                                                     6
```

-continued

<210> SEQ ID NO 8
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 8 ccgcgg                                                                        6

<210> SEQ ID NO 9
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 9 ggcgcc                                                                        6

<210> SEQ ID NO 10
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 10 cccggg                                                                        6

<210> SEQ ID NO 11
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 11 cccggg                                                                        6

<210> SEQ ID NO 12
<211> LENGTH: 9
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (6)..(9)
<223> OTHER INFORMATION: each "n" is independently selected from A, T,
      G, and C

<400> SEQUENCE: 12 cccgcnnnn                                                                     9

<210> SEQ ID NO 13
<211> LENGTH: 6
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: wherein "r" is a purine (A or G)
<220> FEATURE:
<221> NAME/KEY: misc_feature

```
<222> LOCATION: (6)..(6)
<223> OTHER INFORMATION: wherein "y" is a pyrimidine (C or T)

<400> SEQUENCE: 13 rgcgcy                                                                     6

<210> SEQ ID NO 14
<211> LENGTH: 6
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: wherein "r" is a purine (A or G)
<220> FEATURE:
<221> NAME/KEY: misc_feature
<222> LOCATION: (6)..(6)
<223> OTHER INFORMATION: wherein "y" is a pyrimidine (C or T)

<400> SEQUENCE: 14 rccggy                                                                     6

<210> SEQ ID NO 15
<211> LENGTH: 6
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: wherein "y" is a pryimidine (C or T)
<220> FEATURE:
<221> NAME/KEY: misc_feature
<222> LOCATION: (6)..(6)
<223> OTHER INFORMATION: wherein "r" is a purine (A or G)

<400> SEQUENCE: 15 yggccr                                                                     6

<210> SEQ ID NO 16
<211> LENGTH: 6
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: wherein "r" is a purine (A or G)
<220> FEATURE:
<221> NAME/KEY: misc_feature
<222> LOCATION: (4)..(4)
<223> OTHER INFORMATION: wherein "y" is a pyrimidine (C or T)

<400> SEQUENCE: 16 cgrycg                                                                     6

<210> SEQ ID NO 17
<211> LENGTH: 5
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: wherein "w" is A or T
```

```
<400> SEQUENCE: 17 ggwcg                                                                  5

<210> SEQ ID NO 18
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (6)..(10)
<223> OTHER INFORMATION: wherein each "n" is independent selected from
      A, T, C, and G

<400> SEQUENCE: 18 gacgcnnnnn                                                            10

<210> SEQ ID NO 19
<211> LENGTH: 12
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (7)..(12)
<223> OTHER INFORMATION: wherein each "n" is independently selected from
      A, T, G, and C.

<400> SEQUENCE: 19
gtatccnnnn nn                                                         12

<210> SEQ ID NO 20
<211> LENGTH: 33
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (32)..(33)
<223> OTHER INFORMATION: a nuclease blocking modification, such as
      phosphorothioate

<400> SEQUENCE: 20
gatgctgtaa agttgaagta ggtatccgtg agt                                  33

<210> SEQ ID NO 21
<211> LENGTH: 12
<212> TYPE: DNA
<213> ORGANISM: Artificial Sequence
<220> FEATURE:
<223> OTHER INFORMATION: synthetic polynucleotide

<400> SEQUENCE: 21
cgactcacgg at                                                         12

<210> SEQ ID NO 22
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 22 ggcgcc                                                                 6
```

<210> SEQ ID NO 23
<211> LENGTH: 39
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (38)..(39)
<223> OTHER INFORMATION: phosphothiate modification for the last
      nucleotide

<400> SEQUENCE: 23
gatgctgtaa agttgaagta ggtatccgtg agtacatcg                              39

<210> SEQ ID NO 24
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 24
cgcgatgtac tcacggat                                                     18

<210> SEQ ID NO 25
<211> LENGTH: 39
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (34)..(39)
<223> OTHER INFORMATION: wherein each "n" is independently selected from
      A, T, G, and C.
<220> FEATURE:
<221> NAME/KEY: misc_feature
<222> LOCATION: (39)..(39)
<223> OTHER INFORMATION: phosphothiate modification for the last
      nucleotide

<400> SEQUENCE: 25
gatgctgtaa agttgaagta ggtatccgtg agtnnnnnn                              39

<210> SEQ ID NO 26
<211> LENGTH: 17
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(2)
<223> OTHER INFORMATION: "mm" can be any combination of 2 nucleotides
      (A, T, G, C) that is a cohesive end that is generated with an RE
      digestion
<220> FEATURE:
<221> NAME/KEY: misc_feature
<222> LOCATION: (3)..(8)
<223> OTHER INFORMATION: "nnnnnn" can be any combination of 6
      nucleotides (A, T, G, C) that is a reverse complementary sequence
      for the 6 "n" nucleotides in SEQ ID NO:25

<400> SEQUENCE: 26
mmnnnnnnct cacggat                                                      17

<210> SEQ ID NO 27
<211> LENGTH: 17
<212> TYPE: DNA

```
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (3)..(8)
<223> OTHER INFORMATION: "nnnnnn" can be any combination of 6
      nucleotides (A, T, G, C) that is a reverse complementary sequence
      for the 6 "n" nucleotides in SEQ ID NO:25

<400> SEQUENCE: 27
cgnnnnnnct cacggat                                                    17

<210> SEQ ID NO 28
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 28 atcacg                                                                 6

<210> SEQ ID NO 29
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 29 cgatgt                                                                 6

<210> SEQ ID NO 30
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 30 ttaggc                                                                 6

<210> SEQ ID NO 31
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 31 tgacca                                                                 6

<210> SEQ ID NO 32
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 32 acagtg                                                                 6

<210> SEQ ID NO 33
<211> LENGTH: 6
<212> TYPE: DNA
<213> ORGANISM: Artificial Sequence
```

```
<220> FEATURE:
<223> OTHER INFORMATION: synthetic polynucleotide

<400> SEQUENCE: 33 gccaat                                                                      6

<210> SEQ ID NO 34
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 34 cagatc                                                                      6

<210> SEQ ID NO 35
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 35 acttga                                                                      6

<210> SEQ ID NO 36
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 36 gatcag                                                                      6

<210> SEQ ID NO 37
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 37 tagctt                                                                      6

<210> SEQ ID NO 38
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 38 ggctac                                                                      6

<210> SEQ ID NO 39
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 39 cttgta                                                                      6
```

```
<210> SEQ ID NO 40
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 40 agtcaa                                                                      6

<210> SEQ ID NO 41
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 41 agttcc                                                                      6

<210> SEQ ID NO 42
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 42 atgtca                                                                      6

<210> SEQ ID NO 43
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 43 ccgtcc                                                                      6

<210> SEQ ID NO 44
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 44 gtagag                                                                      6

<210> SEQ ID NO 45
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 45 gtccgc                                                                      6

<210> SEQ ID NO 46
<211> LENGTH: 6
<212> TYPE: DNA
<213> ORGANISM: Artificial Sequence
<220> FEATURE:
<223> OTHER INFORMATION: synthetic polynucleotide
```

```
<400> SEQUENCE: 46 gtgaaa                                                              6

<210> SEQ ID NO 47
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 47 gtggcc                                                              6

<210> SEQ ID NO 48
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 48 cgaaac                                                              6

<210> SEQ ID NO 49
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 49 cgtacg                                                              6

<210> SEQ ID NO 50
<211> LENGTH: 26
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (18)..(26)
<223> OTHER INFORMATION: wherein each "n" is independently selected from
      A, T, G, and C.

<400> SEQUENCE: 50
gacatgtatc cggatgtnnn nnnnnn                                       26

<210> SEQ ID NO 51
<211> LENGTH: 11
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(6)
<223> OTHER INFORMATION: each "n" is independently selected from A, T,
      G, and C

<400> SEQUENCE: 51
nnnnnngcgg g                                                       11

<210> SEQ ID NO 52
<211> LENGTH: 11
<212> TYPE: DNA
```

```
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(6)
<223> OTHER INFORMATION: wherein each "n" is independently selected from
      A, T, G, and C.

<400> SEQUENCE: 52
nnnnnngcgg g                                                          11

<210> SEQ ID NO 53
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 53 cgtgat                                                                 6

<210> SEQ ID NO 54
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 54 acatcg                                                                 6

<210> SEQ ID NO 55
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 55 gcctaa                                                                 6

<210> SEQ ID NO 56
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 56 tggtca                                                                 6

<210> SEQ ID NO 57
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 57 cactgt                                                                 6

<210> SEQ ID NO 58
<211> LENGTH: 6
<212> TYPE: DNA
<213> ORGANISM: Artificial Sequence
<220> FEATURE:
```

<223> OTHER INFORMATION: synthetic polynucleotide

<400> SEQUENCE: 58 attggc                                                                  6

<210> SEQ ID NO 59
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 59 gatctg                                                                  6

<210> SEQ ID NO 60
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 60 tcaagt                                                                  6

<210> SEQ ID NO 61
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 61 ctgatc                                                                  6

<210> SEQ ID NO 62
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 62 aagcta                                                                  6

<210> SEQ ID NO 63
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 63 gtagcc                                                                  6

<210> SEQ ID NO 64
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 64 tacaag                                                                  6

```
<210> SEQ ID NO 65
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 65 ttgact                                                                    6

<210> SEQ ID NO 66
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 66 ggaact                                                                    6

<210> SEQ ID NO 67
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 67 tgacat                                                                    6

<210> SEQ ID NO 68
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 68 ggacgg                                                                    6

<210> SEQ ID NO 69
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 69 ctctac                                                                    6

<210> SEQ ID NO 70
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 70 gcggac                                                                    6

<210> SEQ ID NO 71
<211> LENGTH: 6
<212> TYPE: DNA
<213> ORGANISM: Artificial Sequence
<220> FEATURE:
<223> OTHER INFORMATION: synthetic polynucleotide
```

```
<400> SEQUENCE: 71 tttcac                                                              6

<210> SEQ ID NO 72
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 72 ggccac                                                              6

<210> SEQ ID NO 73
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 73 gtttcg                                                              6

<210> SEQ ID NO 74
<211> LENGTH: 6
<212> TYPE: DNA
<213> ORGANISM: Artificial Sequence
<220> FEATURE:
<223> OTHER INFORMATION: synthetic polynucleotide

<400> SEQUENCE: 74 cgtacg                                                              6

<210> SEQ ID NO 75
<211> LENGTH: 15
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(10)
<223> OTHER INFORMATION: wherein each "n" is independent selected from
      A, T, C, and G

<400> SEQUENCE: 75
nnnnnnnnnn gcgtc                                                   15

<210> SEQ ID NO 76
<211> LENGTH: 11
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(5)
<223> OTHER INFORMATION: wherein each "n" is independently selected from
      A, T, G, and C.

<400> SEQUENCE: 76
nnnnnggata c                                                       11

<210> SEQ ID NO 77
<211> LENGTH: 6
<212> TYPE: DNA
<213> ORGANISM: Artificial Sequence
```

```
<220> FEATURE:
<223> OTHER INFORMATION: synthetic polynucleotide

<400> SEQUENCE: 77 ttataa                                                                    6
```

We claim:

1. A method of identifying regions of methylated genomic DNA in a double stranded genomic DNA sample, the method comprising sequentially:
 (a) digesting a double stranded genomic DNA sample with one or more methylation sensitive restriction endonucleases (MSREs), thereby forming digested, unligated DNA fragments;
 (b) amplifying the digested, unligated DNA fragments by multiple displacement amplification (MDA), thereby producing a plurality of heterogeneous amplicons, the MDA comprising denaturing the digested, unligated DNA fragments and forming single stranded DNA fragments, annealing random primers to the single stranded DNA fragments, and extending the primers annealed to the single stranded DNA fragments with a polymerase;
 (c) sequencing the amplicons; and
 (d) identifying the regions of methylated genomic DNA in the double stranded genomic DNA sample based on the sequences of the amplicons.

2. The method of claim 1, wherein the one or more MSREs comprise one or more 4 to 6-nucleotide (4-6 Nt) recognizing MSREs.

3. The method of claim 1, further comprising mapping the sequences of the amplicons.

4. The method of claim 1, wherein the MSREs comprise EagI, NaeI, BssHII, SacII, or a combination thereof.

5. The method of claim 1, wherein at least some of the amplicons comprise CpG rich sequences, and wherein the method further comprises enriching for the amplicons comprising the CpG rich sequences prior to step (c).

6. The method of claim 1, further comprising fragmenting the amplicons prior to step (c).

7. The method of claim 6, wherein said fragmenting the amplicons comprises digestion of the amplicons with one or more restriction endonucleases, or sonication of the amplicons.

8. The method of claim 7, wherein the one or more restriction endonucleases cut in CpG islands of the amplicons.

9. The method of claim 8, wherein the one or more restriction endonucleases are MSREs.

10. The method of claim 9, wherein one or more of the MSREs are HpaII, BstUI, AciI, HinP1I, or a combination thereof.

11. The method of claim 1, wherein step (c) comprises high throughput sequencing of the amplicons.

12. The method of claim 1, wherein the amplicons comprise CpG rich amplicons and CpG poor amplicons, and the method further comprises enriching for the CpG rich amplicons between steps (b) and (c), the enriching step comprising
 digesting the amplicons with one or more restriction endonucleases that cut CpG rich sequences of the amplicons into fragments ranging from about 50 bp to about 500 bp and CpG-poor sequences of the amplicons into fragments greater than 500 bp, and
 selecting the fragments ranging from about 50 bp to about 500 bp after said digesting the amplicons.

13. The method of claim 12, wherein the one or more restriction endonucleases is a single 4-nucleotide recognizing restriction endonuclease.

14. The method of claim 13, wherein the 4-nucleotide recognizing restriction endonuclease is selected from the group consisting of HpaII, MspI, BstUI, AciI, HinP1I, HhaI, HpyCH4IV, FauI, and TaqI.

15. The method of claim 12, wherein the one or more restriction endonucleases are multiple 5-nucleotide recognizing restriction endonucleases, multiple 6-nucleotide recognizing restriction endonucleases, or a combination of 5-nucleotide recognizing restriction endonucleases and 6-nucleotide recognizing restriction endonucleases.

16. The method of claim 1, wherein the polymerase is selected from the group consisting of phi29 DNA polymerase, Bst large fragment DNA polymerase (Exo(-), exo (-)Bca DNA polymerase, phage M2 DNA polymerase, phage Bacteriophage PRD1 DNA polymerase, exo(-) VENT® DNA polymerase, Klenow fragment of DNA polymerase I, T5 DNA polymerase, Sequenase, PRD1 DNA polymerase, and T4 DNA polymerase holoenzyme.

17. The method of claim 16, wherein the polymerase is phi29 DNA polymerase.

18. The method of claim 1, wherein the double stranded genomic DNA sample is from a single cell.

19. The method of claim 1, further comprising identifying regions of unmethylated genomic DNA in the double strand genomic DNA sample.

* * * * *